United States Patent
Ran et al.

(10) Patent No.: US 11,370,762 B2
(45) Date of Patent: Jun. 28, 2022

(54) VINYLARENE DERIVATIVE AND APPLICATION

(71) Applicant: SHENYANG RESEARCH INSTITUTE OF CHEMICAL INDUSTRY CO., LTD., Liaoning (CN)

(72) Inventors: Zhaojin Ran, Liaoning (CN); Baoshan Chai, Liaoning (CN); Wanqiu Wang, Liaoning (CN); Haihong Guang, Liaoning (CN); Jiayuan Jiao, Liaoning (CN)

(73) Assignee: SHENYANG RESEARCH INSTITUTE OF CHEMICAL INDUSTRY CO., LTD., Liaoning (CN)

( * ) Notice: Subject to any disclaimer, the term of this patent is extended or adjusted under 35 U.S.C. 154(b) by 0 days.

(21) Appl. No.: 16/489,815

(22) PCT Filed: May 31, 2018

(86) PCT No.: PCT/CN2018/089152
§ 371 (c)(1),
(2) Date: Aug. 29, 2019

(87) PCT Pub. No.: WO2018/219309
PCT Pub. Date: Dec. 6, 2018

(65) Prior Publication Data
US 2019/0382356 A1    Dec. 19, 2019

(30) Foreign Application Priority Data
Jun. 2, 2017    (CN) .......................... 201710407896.9

(51) Int. Cl.
| | | |
|---|---|---|
| *A61P 35/00* | (2006.01) | |
| *C07D 257/04* | (2006.01) | |
| *C07C 233/55* | (2006.01) | |
| *C07C 275/40* | (2006.01) | |
| *C07C 275/42* | (2006.01) | |
| *C07C 335/22* | (2006.01) | |

(52) U.S. Cl.
CPC ............ *C07D 257/04* (2013.01); *A61P 35/00* (2018.01); *C07C 233/55* (2013.01); *C07C 275/40* (2013.01); *C07C 275/42* (2013.01); *C07C 335/22* (2013.01)

(58) Field of Classification Search
CPC ..... A61P 35/00; C07D 257/04; C07C 233/55; C07C 275/40; C07C 275/42; C07C 335/22
See application file for complete search history.

(56) References Cited

U.S. PATENT DOCUMENTS

| | | | |
|---|---|---|---|
| 6,872,729 B2 | 3/2005 | Shibata et al. | |
| 7,781,595 B2* | 8/2010 | Chen ..................... | A61P 33/02 548/304.4 |
| 9,790,169 B2 | 10/2017 | Balog et al. | |
| 2016/0145247 A1 | 5/2016 | Belanger et al. | |

FOREIGN PATENT DOCUMENTS

| | | |
|---|---|---|
| CN | 1333768 A | 1/2002 |
| CN | 105267214 A | 1/2016 |
| CN | 105555766 A | 5/2016 |
| JP | 2016-529238 A | 9/2016 |
| WO | 2016/161269 A1 | 10/2016 |
| WO | 2016/161279 A1 | 10/2016 |
| WO | 2016/161286 A1 | 10/2016 |

OTHER PUBLICATIONS

CAPLUS printout of RN 2171074-33-0 (Year: 2018).*
International Search Report for PCT/CN2018/089152, dated Sep. 12, 2018 (6pgs. with English translation).
Abou-Zied, O. K., et al. Detecting local heterogeneity and ionization ability in the heat group region of different lipidic phases using modified fluorescent probes. Scientific Reports. 2015. vol. 5, No. 8699 (26 Pages).
Attachment 1. Summary of CAPLUS Database Search Results, pp. 10-18. 附件1. 《CAPLUS数据库检索结果汇总》10-18页. Caplus Printout. 2020 ACS on STN (23 Pages).
Written Opinion of the International Search Authority dated Sep. 18, 2018 for International Application No. PCT/CN2018/089152 (4 pages in Chinese with English translation).
International Preliminary Report on Patentability dated Dec. 3, 2019 for International Application No. PCT/CN2018/089152 (5 pages in Chinese with English translation).
Office Action dated Aug. 11, 2020 for Japanese Patent Application No. 2019-565605 (5 pages in Japanese with English translation).
(Continued)

*Primary Examiner* — Brenda L Coleman
(74) *Attorney, Agent, or Firm* — Smith, Gambrell & Russell, LLP.

(57) ABSTRACT

The present invention relates to a vinylarene deriv. which modulates or inhibits the enzymic activity of indoleamine 2,3-dioxygenase 1 (IDO-1), and the use thereof, and further relates to a vinylarene deriv. and the use thereof. The vinylarene deriv. and its stereoisomer, cis- or trans-isomer, or tautomer thereof and pharmaceutically acceptable salt thereof, has an IDO-1 enzyme inhibitory activity, and is expected to provide brand new therapeutic methods and schemes for related diseases caused by IDO enzymes.

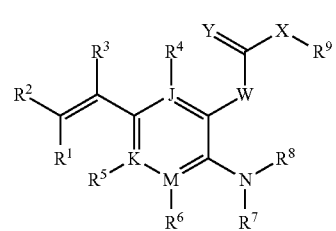

3 Claims, No Drawings

(56) References Cited

OTHER PUBLICATIONS

Decision to Grant dated Feb. 9, 2021 for Japanese Patent Application No. 2019-565605 (4 pages in Japanese with English translation).
Search Report dated Sep. 23, 2020 for Chinese Patent Application No. 2018105503039 (1 page).
First Office Action dated Sep. 29, 2020 for Chinese Patent Application No. 2018105503039 (6 pages in Chinese with English translation).
Notification to Grant dated Feb. 20, 2021 for Chinese Patent Application No. 2018105503039 (1 page in Chinese with English translation).
European Search Opinion dated Oct. 28, 2020 for European Patent Application No. 18809189.6 (7 pages).
Korean Office Action dated May 28, 2021 received in Korean Patent Application No. 10-2019-7025635 (11 pages in Korean, with English translation).

\* cited by examiner

VINYLARENE DERIVATIVE AND APPLICATION

FIELD OF THE INVENTION

The invention relates generally to compounds vinylarene derivative that modulate or inhibit the enzymatic activity of indoleamine 2,3-dioxygenase 1 (IDO-1) and its application, further vinylarene derivative and its application.

BACKGROUND OF THE INVENTION

Indole-2,3-dioxygenase (IDO) is a heme-containing intracellular enzyme that catalyzes the first and rate-determining step in the degradation of amino acid L-tryptophan. IDO catalyzes the essential amino acids L-tryptophan to N-formyl kynurenine and cleans up L-tryptophan in humans. By degrading tryptophan, IDO causes a microenvironment in which tryptophan is absent in the body, which in turn leads to a variety of diseases related to tryptophan deficiency such as cancer, viral infection, depression, organ transplant rejection or autoimmune diseases. Therefore, in recent years, the research of high-efficiency IDO inhibitors has become a hot research in drug development.

There are no IDO-1 inhibitors were approved for listing, and the diseases associated with IDO-1 enzymes still lack treatment methods and treatment options. The development of IDO-1 enzyme inhibitors has a huge potential market.

SUMMARY OF THE INVENTION

The purpose of the invention is to provide a compound which modulates or inhibits the enzymatic activity of IDO and/or a pharmaceutically acceptable salt, its stereoisomer, cis-trans isomer and a tautomer, and a method which modulates or inhibits IDO-1 enzymatic activity, and a application of the compound for the preparation of pharmaceutical.

In order to achieve the above purposes, the technical scheme adopted by the present invention is as follows:

The present invention is a vinylarene derivative as a regulator or inhibitor of indoleamine-2,3-dioxygenase (IDO-1). The aromatic ethylene derivative is a compound shown in formula I, its stereoisomer, cis-trans isomer, tautomer and pharmaceutically acceptable salt thereof.

I wherein
W is selected from $CH_2$, O or NH;
X is selected from $CH_2$, O or NH;
Y is selected from O or S:
J is selected from N or C;
K is selected from N or C;
M is selected from N or C;
$R^1$ and $R^2$ are selected from H, COOH, $CONHR^{10}$, $-CONHSO_2R^{10}$, $COOR^{10}$, $C_1$-$C_{12}$ alkyl, $C_2$-$C_{12}$ alkenyl, the following group which is unsubstituted or substituted by 1-5 $R^{11}$: aryl, heteroaryl;

$R^3$ is selected from H, $C_1$-$C_{12}$ alkyl, halo $C_1$-$C_{12}$ alkyl, $C_2$-$C_2$ alkenyl, halo $C_2$-$C_{12}$ alkenyl, the following group which is unsubstituted or substituted by 1-5 $R^{11}$: aryl, heteroaryl;

$R^4$ is selected from H or halogen;

$R^5$ is selected from H or halogen;

$R^6$ is selected from the group consisting of H, halogen, nitro, cyano, $C_1$-$C_{12}$ alkyl, $C_3$-$C_{12}$ cycloalkyl, $C_3$-$C_{12}$ heterocycloalkyl, halo $C_1$-$C_{12}$ alkyl, $C_1$-$C_{12}$ alkoxy, halo $C_1$-$C_{12}$ alkoxy, $C_1$-$C_{12}$ alkoxy $C_1$-$C_{12}$ alkyl, halo $C_1$-$C_{12}$ alkoxy $C_1$-$C_{12}$ alkyl, $C_2$-$C_{12}$ alkenyl, $C_3$-$C_{12}$ cycloalkenyl, halo $C_2$-$C_{12}$ alkenyl, $C_2$-$C_{12}$ alkynyl, halo $C_2$-$C_{12}$ alkynyl, the following group which is unsubstituted or substituted by 1-5 $R^{11}$: aryl, heteroaryl, aryl $C_1$-$C_{12}$ alkyl, heteroaryl $C_1$-$C_{12}$ alkyl, aryl $C_1$-$C_{12}$ alkoxy, heteroaryl $C_1$-$C_{12}$ alkoxy, aryloxy or heteroaryloxy;

$R^7$ and $R^8$ are the same or different and selected from the group consisting of H, $C_1$-$C_{12}$ alkyl, $C_3$-$C_{12}$ cycloalkyl, $C_3$-$C_{12}$ heterocycloalkyl, halo $C_1$-$C_{12}$ alkyl, $C_1$-$C_{12}$ alkoxy $C_1$-$C_{12}$ alkyl, halo $C_1$-$C_{12}$ alkoxy $C_1$-$C_{12}$ alkyl, $C_2$-$C_{12}$ alkenyl, $C_3$-$C_{12}$ cycloalkenyl, halo $C_2$-$C_{12}$ alkenyl, $C_2$-$C_{12}$ alkynyl, halo $C_2$-$C_{12}$ alkynyl, the following group which is unsubstituted or substituted by 1-5 $R^{11}$: aryl, heteroaryl, aryl $C_1$-$C_{12}$ alkyl, heteroaryl $C_1$-$C_{12}$ alkyl;

$R^9$ is selected from the group consisting of H, $C_1$-$C_{12}$ alkyl, $C_3$-$C_{12}$ cycloalkyl, $C_3$-$C_{12}$ heterocycloalkyl, halo $C_1$-$C_{12}$ alkyl, $C_1$-$C_{12}$ alkoxy, halo $C_1$-$C_{12}$ alkoxy, $C_1$-$C_{12}$ alkoxy $C_1$-$C_{12}$ alkyl, halo $C_2$-$C_{12}$ alkoxy $C_1$-$C_{12}$ alkyl, $C_2$-$C_{12}$ alkenyl, $C_3$-$C_{12}$ cycloalkenyl, halo $C_2$-$C_{12}$ alkenyl, $C_2$-$C_{12}$ alkynyl, halo $C_2$-$C_{12}$ alkynyl, the following group which is unsubstituted or substituted by 1-5 $R^{11}$: aryl, heteroaryl, aryl $C_1$-$C_{12}$ alkyl, heteroaryl $C_1$-$C_{12}$ alkyl;

$R^{10}$ is selected from the group consisting of $C_1$-$C_{12}$ alkyl, $C_3$-$C_{12}$ cycloalkyl, halo $C_1$-$C_{12}$ alkyl, halo $C_3$-$C_{12}$ cycloalkyl, the following group which is unsubstituted or substituted by 1-5 $R^{11}$: aryl, heteroaryl, aryl $C_1$-$C_{12}$ alkyl, heteroaryl $C_1$-$C_{12}$ alkyl;

$R^{11}$ is selected from the group consisting of H, halogen, nitro, cyano, $C_1$-$C_{10}$ alkyl, halo $C_1$-$C_{10}$ alkyl, $C_1$-$C_{10}$ alkoxy, halo $C_1$-$C_{10}$ alkoxy, $C_1$-$C_{10}$ alkylthiol, $C_1$-$C_{10}$ alkylcarbonyl, $C_1$-$C_{10}$ alkoxycarbonyl, $C_2$-$C_{10}$ alkenyl, halo $C_2$-$C_{10}$ alkenyl, $C_3$-$C_{10}$ alkenyloxy, halo $C_3$-$C_{10}$ alkenyloxy, $C_2$-$C_{10}$ alkynyl, halo $C_2$-$C_{10}$ alkynyl, $C_3$-$C_{10}$ alkynyloxy, halo $C_3$-$C_{10}$ alkynyloxy, halo $C_1$-$C_{10}$ alkylthiol, halo $C_1$-$C_{10}$ alkylcarbonyl, $C_1$-$C_{10}$ alkylamino, halo $C_1$-$C_{10}$ alkylamino, $C_2$-$C_{10}$ dialkylamino, $C_1$-$C_{10}$ alkylcarbonylamino, halo $C_1$-$C_{10}$ alkylcarbonylamino, $C_1$-$C_{10}$ alkylaminocarbonyl or halo $C_1$-$C_{10}$ alkylaminocarbonyl.

The compound of the formula I, its stereoisomers, cis-trans isomers, tautomers and pharmaceutically acceptable salts thereof, the more preferred compounds of the formula are:

W is selected from $CH_2$, O or NH;
X is selected from $CH_2$, O or NH;
Y is selected from O or S;
J is selected from N or C;
K is selected from N or C;
M is selected from N or C;

$R^1$ and $R^2$ are selected from the group consisting of COOH, $CONHR^{10}$, $—CONHSO_2R^{10}$, $COOR^{10}$, the following group which is unsubstituted or substituted by 1-5 $R^{11}$: aryl, heteroaryl;

$R^3$ is selected from the group consisting of H, $C_1$-$C_6$ alkyl, halo $C_1$-$C_6$ alkyl, $C_2$-$C_6$ alkenyl, halo $C_2$-$C_6$ alkenyl, the following group which is unsubstituted or substituted by 1-5 $R^{11}$: aryl, heteroaryl;

$R^4$ is selected from H or halogen;

$R^5$ is selected from H or halogen;

$R^6$ is selected from the group consisting of H, halogen, nitro, cyano, $C_1$-$C_6$ alkyl, $C_3$-$C_6$ cycloalkyl, $C_3$-$C_6$ heterocycloalkyl, halo $C_1$-$C_6$ alkyl, $C_1$-$C_6$ alkoxy, halo $C_1$-$C_6$ alkoxy, $C_1$-$C_6$ alkoxy $C_1$-$C_6$ alkyl, halo $C_1$-$C_6$ alkoxy $C_1$-$C_6$ alkyl, $C_2$-$C_6$ alkenyl, $C_3$-$C_6$ cycloalkenyl, halo $C_2$-$C_6$ alkenyl, $C_2$-$C_6$ alkynyl, halo $C_2$-$C_6$ alkynyl, the following group which is unsubstituted or substituted by 1-5 $R^{11}$: aryl, heteroaryl, aryl $C_1$-$C_6$ alkyl, heteroaryl $C_1$-$C_6$ alkyl, aryl $C_1$-$C_6$ alkoxy, heteroaryl $C_2$-$C_6$ alkoxy, aryloxy or heteroaryloxy;

$R^7$ and $R^8$ are the same or different and selected from the group consisting of H, $C_1$-$C_6$ alkyl, $C_3$-$C_6$ cycloalkyl, $C_3$-$C_6$ heterocycloalkyl, halo $C_1$-$C_6$ alkyl, $C_1$-$C_6$ alkoxy $C_1$-$C_6$ alkyl, halo $C_1$-$C_6$ alkoxy $C_1$-$C_6$ alkyl, $C_2$-$C_6$ alkenyl, $C_3$-$C_6$ cycloalkenyl, halo $C_2$-$C_6$ alkenyl, $C_2$-$C_6$ alkynyl, halo $C_2$-$C_6$ alkynyl, the following group which is unsubstituted or substituted by 1-5 $R^{11}$: aryl, heteroaryl, aryl $C_1$-$C_6$ alkyl, heteroaryl $C_1$-$C_6$ alkyl;

$R^9$ is selected from the group consisting of H, $C_1$-$C_6$ alkyl, $C_3$-$C_6$ cycloalkyl, $C_3$-$C_6$ heterocycloalkyl, halo $C_1$-$C_6$ alkyl, $C_1$-$C_6$ alkoxy, halo $C_1$-$C_6$ alkoxy, $C_1$-$C_6$ alkoxy $C_1$-$C_6$ alkyl, halo $C_1$-$C_6$ alkoxy $C_1$-$C_6$ alkyl, $C_2$-$C_6$ alkenyl, $C_3$-$C_6$ cycloalkenyl, halo $C_2$-$C_6$ alkenyl, $C_2$-$C_6$ alkynyl, halo $C_2$-$C_6$ alkynyl, the following group which is unsubstituted or substituted by 1-5 $R^{11}$: aryl, heteroaryl;

$R^{10}$ is selected from the group consisting of $C_1$-$C_6$ alkyl, $C_3$-$C_6$ cycloalkyl, halo $C_1$-$C_6$ alkyl, halo $C_3$-$C_6$ cycloalkyl, unsubstituted or substituted by 1-5 $R^{11}$: aryl, heteroaryl, aryl $C_1$-$C_6$ alkyl, heteroaryl $C_1$-$C_6$ alkyl;

$R^{11}$ is selected from the group consisting of H, halogen, nitro, cyano, $C_1$-$C_6$ alkyl, halo $C_1$-$C_6$ alkyl, $C_1$-$C_6$ alkoxy, halo $C_1$-$C_6$ alkoxy, $C_1$-$C_6$ alkylthiol, $C_1$-$C_6$ alkylcarbonyl, $C_1$-$C_6$ alkoxycarbonyl, $C_2$-$C_6$ alkenyl, halo $C_2$-$C_6$ alkenyl, $C_3$-$C_6$ alkenyloxy, halo $C_3$-$C_6$ alkenyloxy, $C_2$-$C_6$ alkynyl, halo $C_2$-$C_6$ alkynyl, $C_3$-$C_6$ alkynyloxy, halo $C_3$-$C_6$ alkynyloxy, halo $C_1$-$C_6$ alkylthiol, halo $C_1$-$C_6$ alkylcarbonyl, $C_1$-$C_6$ alkylamino, halo $C_1$-$C_6$ alkylamino, $C_2$-$C_6$ dialkylamino, $C_1$-$C_6$ alkylcarbonylamino, halo $C_1$-$C_6$ alkylcarbonylamino, $C_1$-$C_6$ alkylaminocarbonyl or halo $C_1$-$C_6$ alkylaminocarbonyl.

The compound of the formula I, a stereoisomer, a cis-trans isomer, a tautomer thereof and a pharmaceutically acceptable salt thereof, further preferred compounds of the formula:

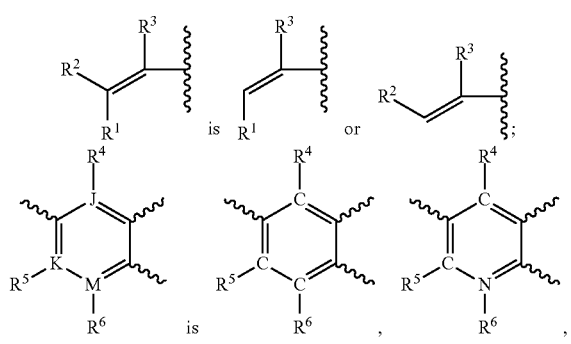

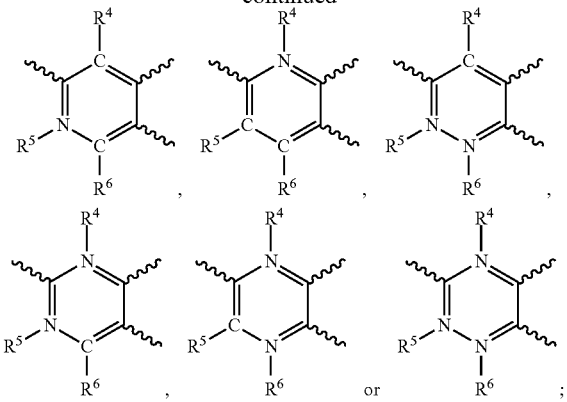

W is selected from NH;
X is selected from $CH_2$, O or NH;
Y is selected from O or S;

$R^1$ and $R^2$ are selected from COOH, $CONHR^{10}$, $—CONHSO_2R^{10}$, $COOR^{10}$,

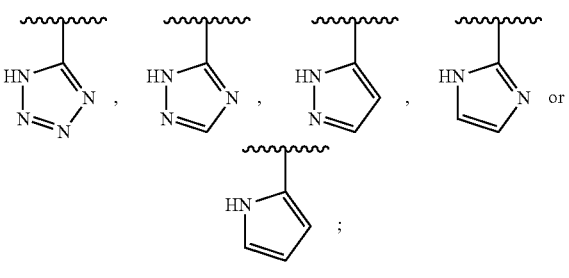

$R^3$ is selected from the group consisting of H, $C_1$-$C_2$ alkyl, halo $C_1$-$C_2$ alkyl, $C_2$-$C_4$ alkenyl, halo $C_2$-$C_4$ alkenyl, the following group which is unsubstituted or substituted by 1-5 $R^{11}$: phenyl, pyridyl;

$R^4$ is selected from H or halogen;

$R^5$ is selected from H or halogen;

$R^6$ is selected from the group consisting of H, halogen, $C_1$-$C_6$ alkyl, $C_3$-$C_6$ cycloalkyl, $C_3$-$C_6$ heterocycloalkyl, $C_1$-$C_6$ alkoxy, $C_1$-$C_6$ alkoxy $C_1$-$C_6$ alkyl, $C_2$-$C_6$ Alkenyl, $C_3$-$C_6$ cycloalkenyl, $C_2$-$C_6$ alkynyl, the following group which is unsubstituted or substituted by 1-5 $R^{11}$: aryl, heteroaryl, aryl $C_1$-$C_6$ alkyl, heteroaryl $C_1$-$C_3$ alkyl, aryl $C_1$-$C_3$ alkoxy, heteroaryl $C_1$-$C_3$ alkoxy, aryloxy or heteroaryloxy;

$R^7$ and $R^8$ are the same or different and selected from the group consisting of H, $C_1$-$C_6$ alkyl, $C_3$-$C_6$ cycloalkyl, $C_3$-$C_6$ heterocycloalkyl, $C_1$-$C_6$ alkoxy $C_1$-$C_6$ alkyl, $C_2$-$C_6$ alkenyl, $C_3$-$C_6$ cycloalkenyl, $C_2$-$C_6$ alkynyl, the following groups which is unsubstituted or substituted by 1-5 $R^{11}$: aryl, heteroaryl, aryl $C_1$-$C_3$: alkyl, heteroaryl $C_1$-$C_3$ alkyl;

$R^9$ is selected from the group consisting of H, $C_1$-$C_6$ alkyl, $C_3$-$C_6$ cycloalkyl, $C_3$-$C_6$ heterocycloalkyl, halo $C_1$-$C_6$ alkyl, $C_1$-$C_6$ alkoxy, halo $C_1$-$C_6$ alkoxy, $C_1$-$C_6$ alkoxy $C_1$-$C_6$ alkyl, halo $C_1$-$C_6$ alkoxy $C_1$-$C_6$ alkyl, $C_2$-$C_6$ alkenyl, $C_3$-$C_6$ cycloalkenyl, halo $C_2$-$C_6$ alkenyl, $C_2$-$C_6$ alkynyl, halo $C_2$-$C_6$ alkynyl, the following group which is unsubstituted or substituted by 1-5 $R^{11}$: aryl, heteroaryl, aryl $C_1$-$C_3$ alkyl, heteroaryl $C_1$-$C_3$ alkyl;

$R^{10}$ is selected from the group consisting of $C_1$-$C_3$ alkyl, $C_3$-$C_6$ cycloalkyl, halo $C_1$-$C_3$ alkyl, halo $C_3$-$C_6$ cycloalkyl, the following group which is unsubstituted or substituted by 1-5 $R^{11}$: aryl, heteroaryl, aryl $C_1$-$C_3$ alkyl, heteroaryl $C_1$-$C_3$ alkyl;

$R^{11}$ is selected from the group consisting of H, halogen, nitro, cyano, $C_1$-$C_6$ alkyl, halo $C_1$-$C_6$ alkyl, $C_1$-$C_6$ alkoxy, halo $C_1$-$C_6$ alkoxy, $C_1$-$C_6$ alkylthiol, $C_1$-$C_6$ alkylcarbonyl, $C_1$-$C_6$ alkoxycarbonyl, $C_2$-$C_6$ alkenyl, halo $C_2$-$C_6$ alkenyl, $C_3$-$C_6$ alkenyloxy, halo $C_3$-$C_6$ alkenyloxy, $C_2$-$C_6$ alkynyl, halo $C_2$-$C_6$ alkynyl, $C_3$-$C_6$ alkynyloxy, halo $C_3$-$C_6$ alkynyloxy, halo $C_1$-$C_6$ alkylthiol, halo $C_1$-$C_6$ alkylcarbonyl, $C_1$-$C_6$ alkylamino, halo $C_1$-$C_6$ alkylamino, $C_2$-$C_6$ dialkylamino, $C_1$-$C_6$ alkylcarbonylamino, halo $C_1$-$C_6$ alkylcarbonylamino, $C_1$-$C_6$ alkylaminocarbonyl or halo $C_1$-$C_6$ alkylaminocarbonyl.

The compound of the formula I, a stereoisomer, a cis-trans isomer, a tautomer thereof and a pharmaceutically acceptable salt thereof, wherein a further preferred compound is:

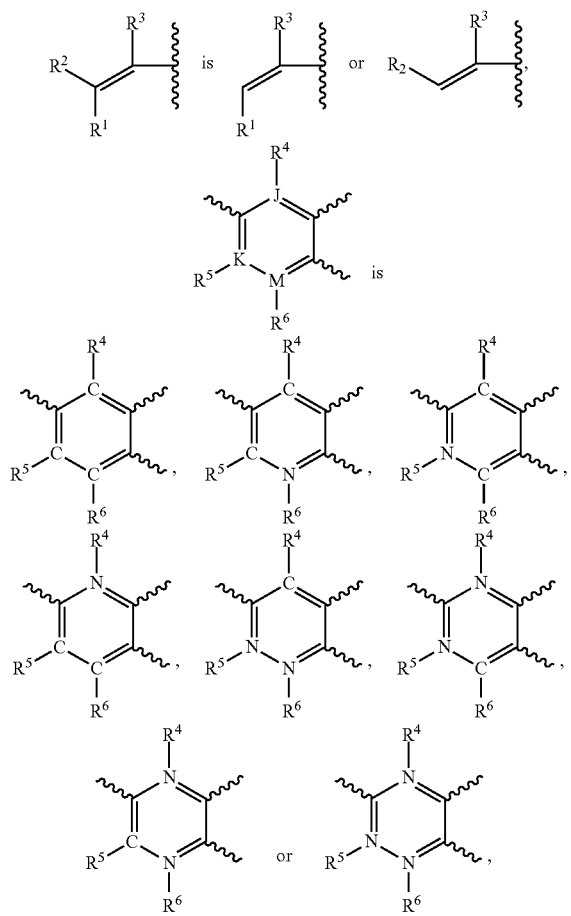

W is selected from NH;
X is selected from $CH_2$, O or NH;
Y is selected from O or S;
$R^1$ and $R^2$ are selected from COOH,

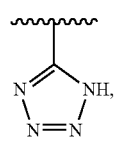

$CONHSO_2CH_3$, $CONHSO_2CF_3$ or $COOCH_2CH_3$;

$R^3$ is selected from H, $CH_3$, $CH_2CH_3$ or $CF_3$;
$R^4$ is selected from H;
$R^5$ is selected from H;
$R^6$ is selected from H;

$R^7$ and $R^8$ are the same or different and selected from the group consisting of H, methyl, ethyl, propyl, isopropyl, n-butyl, isobutyl, cyclopropyl, cyclobutyl, cyclopentyl, cyclohexyl or cycloheptyl;

$R^9$ is selected from the group consisting of H, $C_1$-$C_6$ alkyl, $C_3$-$C_6$ cycloalkyl, $C_{3-6}$ heterocycloalkyl, halo $C_1$-$C_6$ alkyl, $C_1$-$C_6$ alkoxy, halo $C_1$-$C_6$ alkoxy, $C_1$-$C_6$ alkoxy $C_1$-$C_6$ alkyl, halo $C_1$-$C_6$ alkoxy $C_1$-$C_6$ alkyl, $C_2$-$C_6$ alkenyl, $C_3$-$C_6$ cycloalkenyl, halo $C_2$-$C_6$ alkenyl, $C_2$-$C_6$ alkynyl, halo $C_1$-$C_6$ alkynyl, the following group which is unsubstituted or substituted by 1-5 $R^{11}$: aryl, heteroaryl, aryl $C_1$-$C_3$ alkyl, heteroaryl $C_1$-$C_3$ alkyl;

$R^{11}$ is selected from the group consisting of H, halogen, nitro, cyano, $C_1$-$C_3$ alkyl, halo $C_1$-$C_3$ alkyl, $C_1$-$C_3$ alkoxy, halo $C_1$-$C_3$ alkoxy, $C_1$-$C_3$ alkylthiol, $C_1$-$C_3$ alkylcarbonyl, $C_1$-$C_3$ alkoxycarbonyl, $C_2$-$C_3$ alkenyl, halo $C_2$-$C_3$ alkenyl, $C_3$-$C_6$ alkenyloxy, halo $C_3$-$C_6$ alkenyloxy, $C_2$-$C_3$ alkynyl, halo $C_2$-$C_3$ alkynyl, $C_3$-$C_6$ alkynyloxy, halo $C_3$-$C_6$ alkynyloxy, halo $C_1$-$C_3$ alkylthiol, halo $C_1$-$C_3$ alkylcarbonyl, $C_1$-$C_3$ alkylamino, halo $C_1$-$C_3$ alkylamino, $C_2$-$C_3$ dialkylamino, $C_1$-$C_3$ alkylcarbonylamino, halo $C_1$-$C_3$ alkylcarbonylamino, $C_1$-$C_3$ alkylaminocarbonyl or halo $C_1$-$C_3$ alkylaminocarbonyl.

The compound of the formula I, a stereoisomer, a cis-trans isomer, a tautomer thereof and a pharmaceutically acceptable salt thereof, and a still further preferred compound of the formula:

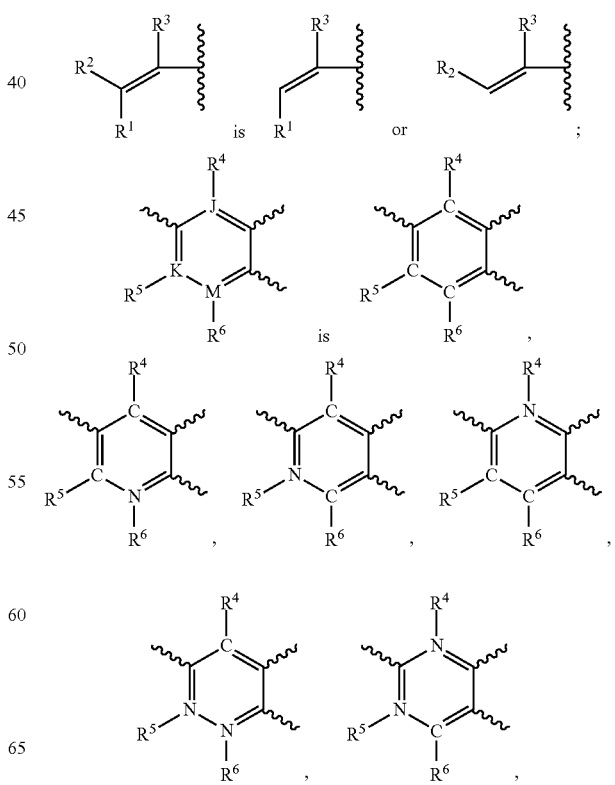

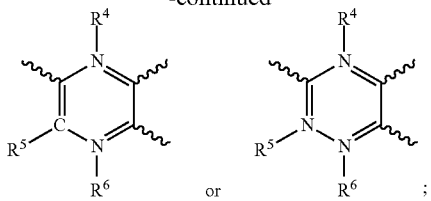

W is selected from NH;
X is selected from CH$_2$, O or NH;
Y is selected from O or S;
R$^1$ and R$^2$ are selected from COOH,

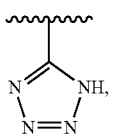

CONHSO$_2$CH$_3$, CONHSO$_2$CF$_3$ or COOCH$_2$CH$_3$;

R$^3$ is selected from H, CH$_3$, CH$_2$CH$_3$ or CF$_3$;
R$^4$ is selected from H;
R$^5$ is selected from H;
R$^6$ is selected from H;
R$^7$ and R$^8$ are the same or different and selected from the group consisting of H, methyl, ethyl, propyl, isopropyl, n-butyl, isobutyl, cyclopropyl, cyclobutyl, cyclopentyl, cyclohexyl or cycloheptyl;
R$^9$ is selected from the group consisting of phenyl, 2-methylphenyl, 3-methylphenyl, 4-methylphenyl, 2,4-dimethylphenyl, 2-fluorophenyl, 3-fluorophenyl, 4-fluorophenyl, 2,4-difluorophenyl, 2-fluoro-4-methylphenyl, 3-trifluoromethyl-4-chlorophenyl, 2-chlorophenyl, 3-chlorophenyl, 4-chlorophenyl, 2,4-dichlorophenyl, 2-trifluoromethylphenyl, 3-trifluoromethylphenyl, 4-trifluoromethylphenyl, 5-methylisoxazolyl.

The compound of the formula I, a stereoisomer, a cis-trans isomer, a tautomer thereof and a pharmaceutically acceptable salt thereof, and a still further preferred compound of the formula:

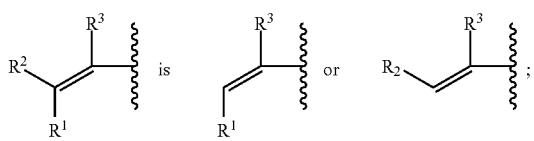

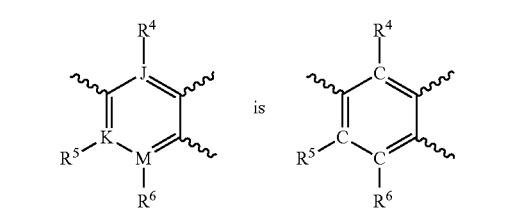

W is NH;
X is NH or CH$_2$;
Y is O;
R$^1$ and R$^2$ is selected from COOH,

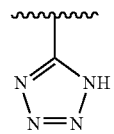

or COOCH$_2$CH$_3$;
R$^3$ is selected from CH$_3$;
R$^4$ is selected from H;
R$^5$ is selected from H;
R$^6$ is selected from H;
R$^7$ and R$^8$ are the same or different and selected from n-butyl or isobutyl;
R$^9$ is selected from the group consisting of 2-methylphenyl, 3-methylphenyl, 4-methylphenyl, 2,4-dimethylphenyl, 2,4-difluorophenyl, 2-fluoro-4-methylphenyl, 3-trifluoromethyl-4-chlorophenyl, phenyl, 2-chlorophenyl, 3-chlorophenyl, 4-chlorophenyl, 2,4-dichlorophenyl, 2-fluorophenyl, 4-fluorophenyl, 3-fluorophenyl or 5-methylisoxazolyl.

The above pharmaceutically acceptable salt prepared by compound and base can be sodium salt, potassium salt, calcium salt, zinc salt, magnesium salt and other metal ion salt. It also can be meglumine salt, aminobutanediol salt, aminoethanol salt, lysine salt, arginine salt and other organic salt. Acid radical salt can be hydrochloride, sulfate, hydrobromate, mesylate, citrate, oxalate, succinate, maleate, citrate, acetate, lactate, phosphate, hydroiodate, nitrate, tartaric acid, p-toluene sulfonic acid, etc.

In the definition of compound of formula I, the terms are generally defined as follows:

Halogen: fluorine, chlorine, bromine or iodine.

Alkyl: straight or branched alkyl, such as methyl, ethyl, propyl, isopropyl, n-butyl, or tert-butyl.

Cycloalkyl: a heterocyclic ring alkyl; such as cyclopropyl, cyclopentyl, or cyclohexyl, which is substituted or unsubstituted. Substituent group such as methyl, halogen, etc.

Heterocyclic alkyl: a ring alkyl substituted or unsubstituted containing one or more N, O, S heteroatoms, such as tetrahydrofuranyl or cyclopentanyl. Substituent group such as methyl, halogen, etc.

Halo alkyl: straight or branched alkyl, in which the hydrogen atoms may be partially or completely replaced by halo atoms, such as chloromethyl, dichloromethyl, trichloromethyl, fluoromethyl, difluoromethyl, trifluoromethyl, etc.

Alkoxy: Straight or branched alkyl groups are linked to the structure by oxygen atom bonds.

Halo alkoxy: Straight or branched alkoxy groups in which the hydrogen atoms may be partially or completely replaced by halogen atoms. For example, chloromethoxy, dichloromethoxy, trichloromethoxy, fluoromethoxy, difluoromethoxy, trifluoromethoxy, chlorofluoromethoxy, trifluoroethoxy, etc.

Alkoxy alkyl: The alkoxy group is linked to the structure by alkyl group. Such as, —CH$_2$OCH$_3$, —CH$_2$OCH$_2$CH$_3$.

Halo alkoxy alkyl: The hydrogen atoms in alkoxyalkyl groups may be partially or completely replaced by halogen atoms. Such as, —CH$_2$OCH$_2$CH$_2$Cl.

Alkylthiol: Straight or branched alkyl groups that is bonded to a structure by an atomic sulfur bond.

Halo alkylthiol: Straight or branched alkylthiol groups in which the hydrogen atoms may be partially or completely replaced by halogen atoms. For example, chloromethane, dichloromethane, trichloromethane, fluoromethane, difluoromethane, trifluoromethane, chlorofluoromethane, etc.

Alkylamino: Straight or branched alkyl groups bonded to a structure by a nitrogen atom.

Halo alkylamino: Straight or branched alkylamino groups in which the hydrogen atoms may be partially or completely replaced by the halogen atoms.

Alkenyl: Straight or branched alkenes groups, such as vinyl, 1-propylene, 2-propylene, and different butylene, pentenyl, and hexenyl isomers. Alkenes also include polyenes, such as 1,2-propylene, and 2,4-hexadienyl.

Halo alkene: Straight or branched alkenes groups in which hydrogen atoms may be partially or completely replaced by halogen atoms.

Alkynyl: Straight or branched alkynes groups, such as acetylenyl, 1-propargynyl, 2-propargynyl, and different butynyl, pentynyl, and hexynyl isomers. Alkynyl also includes groups consisting of multiple triple bonds, such as 2,5-hexylenyl.

Halo alkynyl: Straight or branched alkynes groups in which hydrogen atoms may be partially or completely replaced by halogen atoms.

Alkenyloxy: Straight or branched alkenyl groups bonded to a structure by an oxygen bond.

Halo alkenyloxy: Straight or branched alkenyl groups in which the hydrogen atoms may be partially or completely replaced by halogen atoms.

Alkynyloxy: Straight or branched alkynyl groups bonded to a structure by an oxygen atom.

Halo alkynyloxy: Straight or branched alkynyl groups in which the hydrogen atoms may be partially or completely replaced by halogen atoms.

Alkyl carbonyl: Straight or branched alkyl groups bonded to a structure by a carbonyl group (—CO—), such as an acetyl group.

Halo alkyl carbonyl: Straight or branched Alkyl carbonyl groups in which the hydrogen atoms may be partially or completely replaced by halogen atoms.

Alkoxy carbonyl: Straight or branched alkoxy groups bonded to a structure by a carbonyl group (—CO—). Such as —COOCH$_3$, —COOCH$_2$CH$_3$.

Halo alkoxyl carbonyl: Straight or branched alkoxyl carbonyl groups in which the hydrogen atoms may be partially or completely replaced by halogen atoms. Such as —COOCH$_2$CF$_3$, —COOCH$_2$CH$_2$Cl etc.

Alkyl carbonyl amino: Such as —NHCOCH$_3$, —NHCOC(CH$_3$)$_3$

Alkyl aminocarbonyl: Such as —C(=O)NHCH$_3$, —C(=O)N(CH$_3$)$_2$

The aromatic parts of aryl, aryl alkyl, aryloxy, aryl aryloxy and aryl amino include phenyl or naphthalene group, etc.

Hetero aryl groups are five-membered rings or six-membered rings containing one or more N, O, S hetero atoms. For example, furanyl, pyrazolyl, thiazolyl, pyridyl, pyrimidyl, pyrazinyl, pyridazinyl, triazinyl, quinolyl, etc.

Heteroaryl part of heteroaryl alkyl, heteroaryloxy and heteroaryl alkoxy groups refers to a five or a six-membered ring containing one or more N, O, S heteroatoms. For example, furyl, pyrazolyl, thiazolyl, pyridyl, pyrimidyl, pyrazinyl, pyridazinyl, triazinyl, quinolyl, benzoxazolyl, indolyl, etc.

The application of a vinylarene derivative, the compound shown in formula I, its stereoisomer, cis-trans isomer, tautomer and pharmaceutically acceptable salt thereof, or a combination thereof, in the preparation of an inhibitor for inhibiting the activity of IDO-1 enzyme.

The application of a vinylarene derivative, the compound shown in formula I, its stereoisomer, cis-trans isomer, tautomer and pharmaceutically acceptable salt thereof, or a combination thereof, in the preparation of an anti-cancer drug, a viral infectious agent, a depressant, an organ transplant rejection agent or an autoimmune enhancer.

The cancer is colon cancer, pancreatic cancer, breast cancer, prostate cancer, lung cancer, ovarian cancer, cervical cancer, kidney cancer, head and neck cancer, lymphoma, leukemia or melanoma.

A pharmaceutical composition comprising any one or more compounds shown in formula I, its stereoisomer, cis-trans isomer, tautomer, pharmaceutically acceptable salt thereof and pharmaceutically acceptable carriers or diluents.

The compounds in the present invention, stereoisomer can be formed by connecting different substituents with carbon-carbon double bond (Z and E are used to represent different configurations, respectively). The present invention includes Z-type isomer and E-type isomer and their mixtures in any proportion.

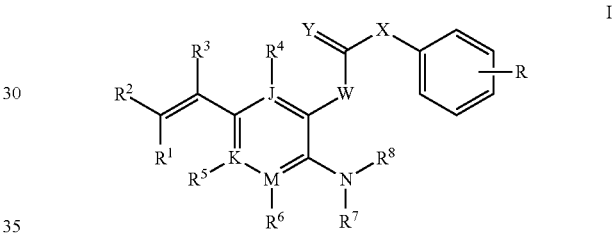

In formula I

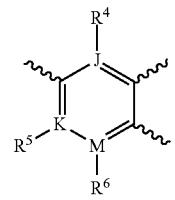

the specific substituent is:

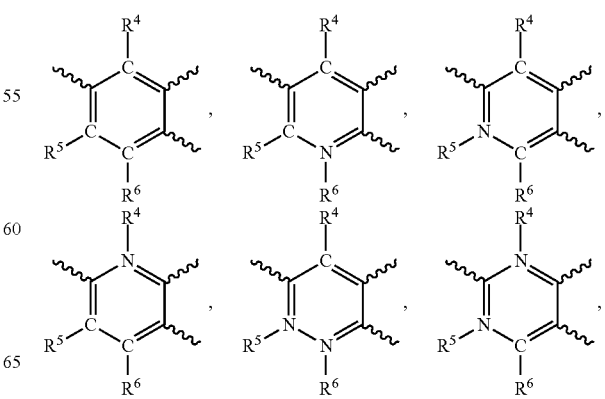

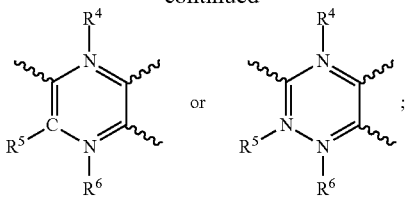

In formula I, the specific substituent of W is $CH_2$, O or NH;

In formula I, the specific substituent of X is $CH_2$, O or NH;

In formula I, the specific substituent of Y is O or S;

In formula I, the specific substituents in $R^3$ are H, $CH_3$, $CH_2CH_3$, $CH_2CH_2CH_3$ and $CF_3$.

In formula I, the specific substituents of $R^4$ are H, Cl, Br and I.

In formula I, the specific substituents of $R^5$ are H, Cl, Br and I.

The specific substituents of $R^6$ in formula I are shown in table 1,

TABLE I

H
Cl
Br
I
$NO_2$
CN
$CH_3$
$CH_2CH_3$
$CH_2CH_2CH_3$
$CH_2CH_2CH_2CH_3$
$CH_2(CH_2)_3CH_3$

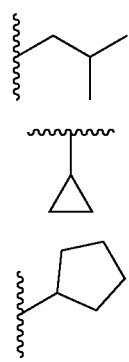

TABLE I-continued

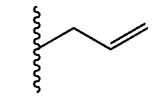

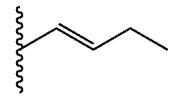

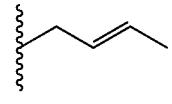

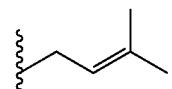

In formula I, $R^1$ and $R^2$ are the same or different, and the specific substituents are shown in table 2. The definitions of other substituents in formula I, such as $R^3$, $R^4$ and $R^5$, are the same as above.

TABLE 2

H
COOH
$COOCH_2CH_3$
$CONHSO_2CH_3$
$CONHSO_2CF_3$

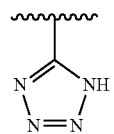

In formula I, $R^7$ and $R^8$ are the same or different, and the specific substituents are shown in table 3. The definitions of other substituents in formula I, such as $R^3$, $R^4$ and $R^5$, are the same as above.

TABLE 3

H
$CH_3$
$CH_2CH_3$
$CH_2CH_2CH_3$

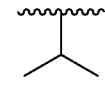

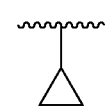

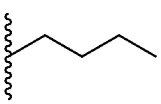 [SMILES: *CCCC]

TABLE 3-continued
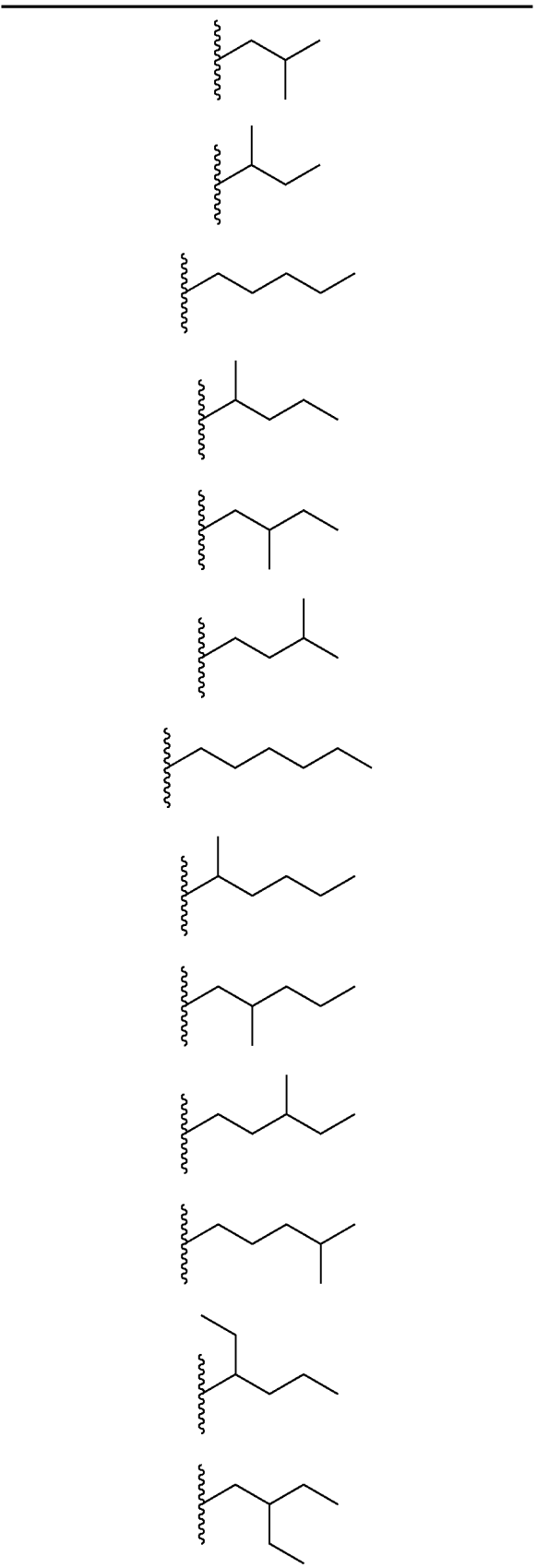
TABLE 3-continued
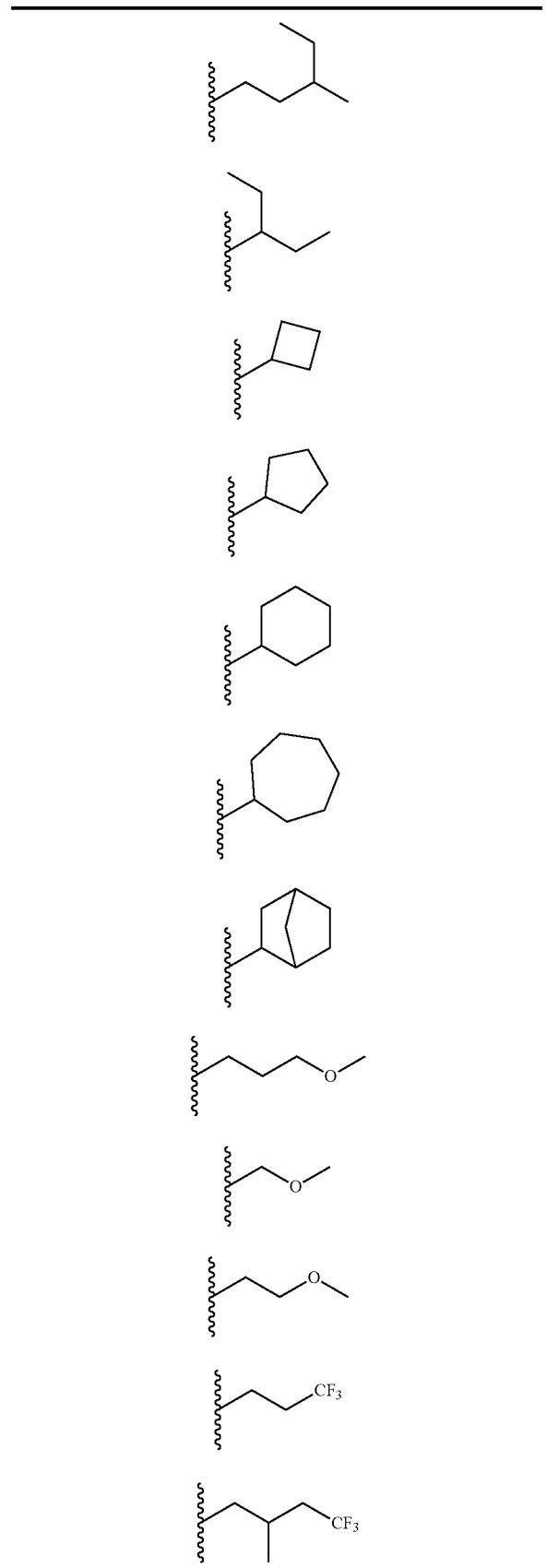

TABLE 3-continued
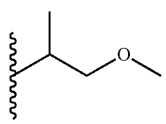 [SMILES: *C(C)COC]
5
The specific substituents of $R^9$ in formula I, are shown in table 4. The definitions of other substituents in formula I, such as $R^3$, $R^4$ and $R^5$, are the same as above.
TABLE 4
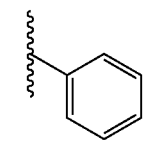 [SMILES: *c1ccccc1]
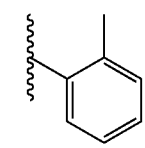 [SMILES: *c1ccccc1C]
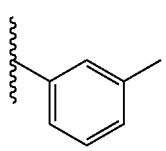
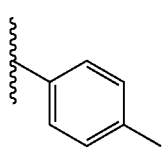 [SMILES: *c1ccc(C)cc1]
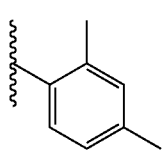 [SMILES: *c1ccc(C)cc1C]
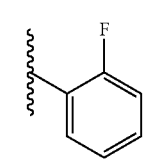
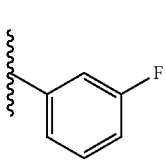
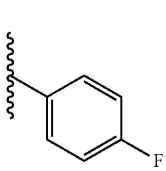 [SMILES: *c1ccc(F)cc1]
TABLE 4-continued
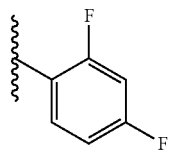 [SMILES: *c1ccc(F)cc1F]
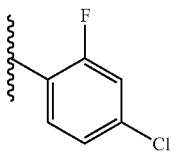
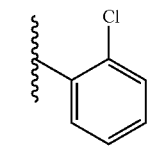 [SMILES: *c1ccccc1Cl]
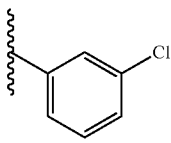 [SMILES: *c1cccc(Cl)c1]
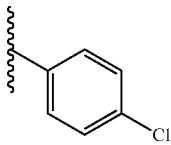 [SMILES: *c1ccc(Cl)cc1]
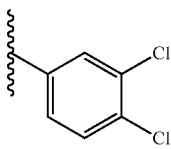 [SMILES: *c1ccc(Cl)c(Cl)c1]
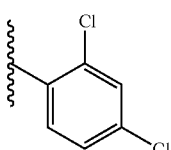
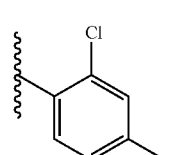
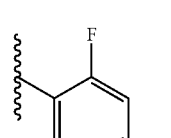
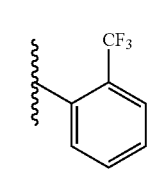

TABLE 4-continued

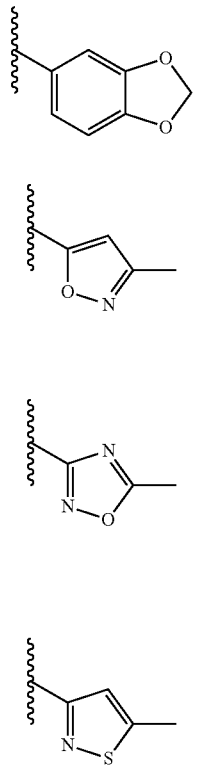

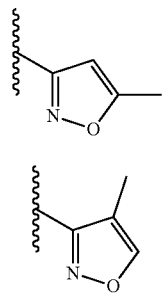

In the present invention, the specific compound in formula I which inhibits the activity of the IDO enzyme is shown as formula II, The specific compound listed in table 5, but the present invention is not limited by these compounds

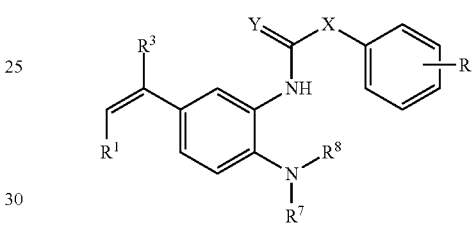

Formula II

TABLE 5

| Compound Number | R¹ | R³ | R⁷ | R⁸ | R | Y | X |
|---|---|---|---|---|---|---|---|
| 1 | COOCH$_2$CH$_3$ | CH$_3$ | n-butyl | n-butyl | 2-CH$_3$ | O | NH |
| 2 | COOCH$_2$CH$_3$ | CH$_3$ | n-butyl | n-butyl | 4-CH$_3$ | O | NH |
| 3 | COOCH$_2$CH$_3$ | CH$_3$ | n-butyl | n-butyl | 2,4-2CH$_3$ | O | NH |
| 4 | COOCH$_2$CH$_3$ | CH$_3$ | n-butyl | n-butyl | 2-F | O | NH |
| 5 | COOCH$_2$CH$_3$ | CH$_3$ | n-butyl | n-butyl | 4-F | O | NH |
| 6 | COOCH$_2$CH$_3$ | CH$_3$ | n-butyl | n-butyl | 2,4-2F | O | NH |
| 7 | COOCH$_2$CH$_3$ | CH$_3$ | n-butyl | n-butyl | 2-F-4-CH$_3$ | O | NH |
| 8 | COOH | CH$_3$ | n-butyl | n-butyl | 2-CH$_3$ | O | NH |
| 9 | COOH | CH$_3$ | n-butyl | n-butyl | 4-CH$_3$ | O | NH |
| 10 | COOH | CH$_3$ | n-butyl | n-butyl | 2,4-2CH$_3$ | O | NH |
| 11 | COOH | CH$_3$ | n-butyl | n-butyl | 2-F | O | NH |
| 12 | COOH | CH$_3$ | n-butyl | n-butyl | 4-F | O | NH |
| 13 | COOH | CH$_3$ | n-butyl | n-butyl | 2,4-2F | O | NH |
| 14 | COOH | CH$_3$ | n-butyl | n-butyl | 2-F-4-CH$_3$ | O | NH |
| 15 | CONHSO$_2$CH$_3$ | CH$_3$ | n-butyl | n-butyl | 2-CH$_3$ | O | NH |
| 16 | CONHSO$_2$CH$_3$ | CH$_3$ | n-butyl | n-butyl | 4-CH$_3$ | O | NH |
| 17 | CONHSO$_2$CH$_3$ | CH$_3$ | n-butyl | n-butyl | 2,4-2CH$_3$ | O | NH |
| 18 | CONHSO$_2$CH$_3$ | CH$_3$ | n-butyl | n-butyl | 2-F | O | NH |
| 19 | CONHSO$_2$CH$_3$ | CH$_3$ | n-butyl | n-butyl | 4-F | O | NH |
| 20 | CONHSO$_2$CH$_3$ | CH$_3$ | n-butyl | n-butyl | 2,4-2F | O | NH |
| 21 | CONHSO$_2$CH$_3$ | CH$_3$ | n-butyl | n-butyl | 2-F-4-CH$_3$ | O | NH |
| 22 | CONHSO$_2$CF$_3$ | CH$_3$ | n-butyl | n-butyl | 2-CH$_3$ | O | NH |
| 23 | CONHSO$_2$CF$_3$ | CH$_3$ | n-butyl | n-butyl | 4-CH$_3$ | O | NH |
| 24 | CONHSO$_2$CF$_3$ | CH$_3$ | n-butyl | n-butyl | 2,4-2CH$_3$ | O | NH |
| 25 | CONHSO$_2$CF$_3$ | CH$_3$ | n-butyl | n-butyl | 2-F | O | NH |
| 26 | CONHSO$_2$CF$_3$ | CH$_3$ | n-butyl | n-butyl | 4-F | O | NH |
| 27 | CONHSO$_2$CF$_3$ | CH$_3$ | n-butyl | n-butyl | 2,4-2F | O | NH |
| 28 | CONHSO$_2$CF$_3$ | CH$_3$ | n-butyl | n-butyl | 2-F-4-CH$_3$ | O | NH |
| 29 | 5-tetrazolyl | CH$_3$ | n-butyl | n-butyl | 2-CH$_3$ | O | NH |
| 30 | 5-tetrazolyl | CH$_3$ | n-butyl | n-butyl | 4-CH$_3$ | O | NH |
| 31 | 5-tetrazolyl | CH$_3$ | n-butyl | n-butyl | 2,4-2CH$_3$ | O | NH |
| 32 | 5-tetrazolyl | CH$_3$ | n-butyl | n-butyl | 2-F | O | NH |
| 33 | 5-tetrazolyl | CH$_3$ | n-butyl | n-butyl | 4-F | O | NH |
| 34 | 5-tetrazolyl | CH$_3$ | n-butyl | n-butyl | 2,4-2F | O | NH |
| 35 | 5-tetrazolyl | CH$_3$ | n-butyl | n-butyl | 2-F-4-CH$_3$ | O | NH |
| 36 | 5-tetrazolyl | CH$_3$ | n-butyl | n-butyl | 2-CH$_3$ | O | NH |

TABLE 5-continued

| Compound Number | R¹ | R³ | R⁷ | R⁸ | R | Y | X |
|---|---|---|---|---|---|---|---|
| 37 | 5-tetrazolyl | CH₃ | n-butyl | n-butyl | 4-CH₃ | O | NH |
| 38 | 5-tetrazolyl | CH₃ | n-butyl | n-butyl | 2,4-2CH₃ | O | NH |
| 39 | 5-tetrazolyl | CH₃ | n-butyl | n-butyl | 2-F | O | NH |
| 40 | 5-tetrazolyl | CH₃ | n-butyl | n-butyl | 4-F | O | NH |
| 41 | 5-tetrazolyl | CH₃ | n-butyl | n-butyl | 2,4-2F | O | NH |
| 42 | 5-tetrazolyl | CH₃ | n-butyl | n-butyl | 2-F-4-CH₃ | O | NH |
| 43 | COOCH₂CH₃ | CH₃ | isobutyl | isobutyl | 2-CH₃ | O | NH |
| 44 | COOCH₂CH₃ | CH₃ | isobutyl | isobutyl | 4-CH₃ | O | NH |
| 45 | COOCH₂CH₃ | CH₃ | isobutyl | isobutyl | 2,4-2CH₃ | O | NH |
| 46 | COOCH₂CH₃ | CH₃ | isobutyl | isobutyl | 2-F | O | NH |
| 47 | COOCH₂CH₃ | CH₃ | isobutyl | isobutyl | 4-F | O | NH |
| 48 | COOCH₂CH₃ | CH₃ | isobutyl | isobutyl | 2,4-2F | O | NH |
| 49 | COOCH₂CH₃ | CH₃ | isobutyl | isobutyl | 2-F-4-CH₃ | O | NH |
| 50 | COOH | CH₃ | isobutyl | isobutyl | 2-CH₃ | O | NH |
| 51 | COOH | CH₃ | isobutyl | isobutyl | 4-CH₃ | O | NH |
| 52 | COOH | CH₃ | isobutyl | isobutyl | 2,4-2CH₃ | O | NH |
| 53 | COOH | CH₃ | isobutyl | isobutyl | 2-F | O | NH |
| 54 | COOH | CH₃ | isobutyl | isobutyl | 4-F | O | NH |
| 55 | COOH | CH₃ | isobutyl | isobutyl | 2,4-2F | O | NH |
| 56 | COOH | CH₃ | isobutyl | isobutyl | 2-F-4-CH₃ | O | NH |
| 57 | CONHSO₂CH₃ | CH₃ | isobutyl | isobutyl | 2-CH₃ | O | NH |
| 58 | CONHSO₂CH₃ | CH₃ | isobutyl | isobutyl | 4-CH₃ | O | NH |
| 59 | CONHSO₂CH₃ | CH₃ | isobutyl | isobutyl | 2,4-2CH₃ | O | NH |
| 60 | CONHSO₂CH₃ | CH₃ | isobutyl | isobutyl | 2-F | O | NH |
| 61 | CONHSO₂CH₃ | CH₃ | isobutyl | isobutyl | 4-F | O | NH |
| 62 | CONHSO₂CH₃ | CH₃ | isobutyl | isobutyl | 2,4-2F | O | NH |
| 63 | CONHSO₂CH₃ | CH₃ | isobutyl | isobutyl | 2-F-4-CH₃ | O | NH |
| 64 | CONHSO₂CF₃ | CH₃ | isobutyl | isobutyl | 2-CH₃ | O | NH |
| 65 | CONHSO₂CF₃ | CH₃ | isobutyl | isobutyl | 4-CH₃ | O | NH |
| 66 | CONHSO₂CF₃ | CH₃ | isobutyl | isobutyl | 2,4-2CH₃ | O | NH |
| 67 | CONHSO₂CF₃ | CH₃ | isobutyl | isobutyl | 2-F | O | NH |
| 68 | CONHSO₂CF₃ | CH₃ | isobutyl | isobutyl | 4-F | O | NH |
| 69 | CONHSO₂CF₃ | CH₃ | isobutyl | isobutyl | 2,4-2F | O | NH |
| 70 | CONHSO₂CF₃ | CH₃ | isobutyl | isobutyl | 2-F-4-CH₃ | O | NH |
| 71 | 5-tetrazolyl | CH₃ | isobutyl | isobutyl | 2-CH₃ | O | NH |
| 72 | 5-tetrazolyl | CH₃ | isobutyl | isobutyl | 4-CH₃ | O | NH |
| 73 | 5-tetrazolyl | CH₃ | isobutyl | isobutyl | 2,4-2CH₃ | O | NH |
| 74 | 5-tetrazolyl | CH₃ | isobutyl | isobutyl | 2-F | O | NH |
| 75 | 5-tetrazolyl | CH₃ | isobutyl | isobutyl | 4-F | O | NH |
| 76 | 5-tetrazolyl | CH₃ | isobutyl | isobutyl | 2,4-2F | O | NH |
| 77 | 5-tetrazolyl | CH₃ | isobutyl | isobutyl | 2-F-4-CH₃ | O | NH |
| 78 | 5-tetrazolyl | CH₃ | isobutyl | isobutyl | 2-CH₃ | O | NH |
| 79 | 5-tetrazolyl | CH₃ | isobutyl | isobutyl | 4-CH₃ | O | NH |
| 80 | 5-tetrazolyl | CH₃ | isobutyl | isobutyl | 2,4-2CH₃ | O | NH |
| 81 | 5-tetrazolyl | CH₃ | isobutyl | isobutyl | 2-F | O | NH |
| 82 | 5-tetrazolyl | CH₃ | isobutyl | isobutyl | 4-F | O | NH |
| 83 | 5-tetrazolyl | CH₃ | isobutyl | isobutyl | 2,4-2F | O | NH |
| 84 | 5-tetrazolyl | CH₃ | isobutyl | isobutyl | 2-F-4-CH₃ | O | NH |
| 85 | COOCH₂CH₃ | CH₃ | cyclohexyl | isobutyl | 2-CH₃ | O | NH |
| 86 | COOCH₂CH₃ | CH₃ | cyclohexyl | isobutyl | 4-CH₃ | O | NH |
| 87 | COOCH₂CH₃ | CH₃ | cyclohexyl | isobutyl | 2,4-2CH₃ | O | NH |
| 88 | COOCH₂CH₃ | CH₃ | cyclohexyl | isobutyl | 2-F | O | NH |
| 89 | COOCH₂CH₃ | CH₃ | cyclohexyl | isobutyl | 4-F | O | NH |
| 90 | COOCH₂CH₃ | CH₃ | cyclohexyl | isobutyl | 2,4-2F | O | NH |
| 91 | COOCH₂CH₃ | CH₃ | cyclohexyl | isobutyl | 2-F-4-CH₃ | O | NH |
| 92 | COOH | CH₃ | cyclohexyl | isobutyl | 2-CH₃ | O | NH |
| 93 | COOH | CH₃ | cyclohexyl | isobutyl | 4-CH₃ | O | NH |
| 94 | COOH | CH₃ | cyclohexyl | isobutyl | 2,4-2CH₃ | O | NH |
| 95 | COOH | CH₃ | cyclohexyl | isobutyl | 2-F | O | NH |
| 96 | COOH | CH₃ | cyclohexyl | isobutyl | 4-F | O | NH |
| 97 | COOH | CH₃ | cyclohexyl | isobutyl | 2,4-2F | O | NH |
| 98 | COOH | CH₃ | cyclohexyl | isobutyl | 2-F-4-CH₃ | O | NH |
| 99 | CONHSO₂CH₃ | CH₃ | cyclohexyl | isobutyl | 2-CH₃ | O | NH |
| 100 | CONHSO₂CH₃ | CH₃ | cyclohexyl | isobutyl | 4-CH₃ | O | NH |
| 101 | CONHSO₂CH₃ | CH₃ | cyclohexyl | isobutyl | 2,4-2CH₃ | O | NH |
| 102 | CONHSO₂CH₃ | CH₃ | cyclohexyl | isobutyl | 2-F | O | NH |
| 103 | CONHSO₂CH₃ | CH₃ | cyclohexyl | isobutyl | 4-F | O | NH |
| 104 | CONHSO₂CH₃ | CH₃ | cyclohexyl | isobutyl | 2,4-2F | O | NH |
| 105 | CONHSO₂CH₃ | CH₃ | cyclohexyl | isobutyl | 2-F-4-CH₃ | O | NH |
| 106 | CONHSO₂CF₃ | CH₃ | cyclohexyl | isobutyl | 2-CH₃ | O | NH |
| 107 | CONHSO₂CF₃ | CH₃ | cyclohexyl | isobutyl | 4-CH₃ | O | NH |
| 108 | CONHSO₂CF₃ | CH₃ | cyclohexyl | isobutyl | 2,4-2CH₃ | O | NH |
| 109 | CONHSO₂CF₃ | CH₃ | cyclohexyl | isobutyl | 2-F | O | NH |
| 110 | CONHSO₂CF₃ | CH₃ | cyclohexyl | isobutyl | 4-F | O | NH |
| 111 | CONHSO₂CF₃ | CH₃ | cyclohexyl | isobutyl | 2,4-2F | O | NH |
| 112 | CONHSO₂CF₃ | CH₃ | cyclohexyl | isobutyl | 2-F-4-CH₃ | O | NH |
| 113 | 5-tetrazolyl | CH₃ | cyclohexyl | isobutyl | 2-CH₃ | O | NH |

TABLE 5-continued

| Compound Number | R¹ | R³ | R⁷ | R⁸ | R | Y | X |
|---|---|---|---|---|---|---|---|
| 114 | 5-tetrazolyl | $CH_3$ | cyclohexyl | isobutyl | 4-$CH_3$ | O | NH |
| 115 | 5-tetrazolyl | $CH_3$ | cyclohexyl | isobutyl | 2,4-2$CH_3$ | O | NH |
| 116 | 5-tetrazolyl | $CH_3$ | cyclohexyl | isobutyl | 2-F | O | NH |
| 117 | 5-tetrazolyl | $CH_3$ | cyclohexyl | isobutyl | 4-F | O | NH |
| 118 | 5-tetrazolyl | $CH_3$ | cyclohexyl | isobutyl | 2,4-2F | O | NH |
| 119 | 5-tetrazolyl | $CH_3$ | cyclohexyl | isobutyl | 2-F-4-$CH_3$ | O | NH |
| 120 | 5-tetrazolyl | $CH_3$ | cyclohexyl | isobutyl | 2-$CH_3$ | O | NH |
| 121 | 5-tetrazolyl | $CH_3$ | cyclohexyl | isobutyl | 4-$CH_3$ | O | NH |
| 122 | 5-tetrazolyl | $CH_3$ | cyclohexyl | isobutyl | 2,4-2$CH_3$ | O | NH |
| 123 | 5-tetrazolyl | $CH_3$ | cyclohexyl | isobutyl | 2-F | O | NH |
| 124 | 5-tetrazolyl | $CH_3$ | cyclohexyl | isobutyl | 4-F | O | NH |
| 125 | 5-tetrazolyl | $CH_3$ | cyclohexyl | isobutyl | 2,4-2F | O | NH |
| 126 | 5-tetrazolyl | $CH_3$ | cyclohexyl | isobutyl | 2-F-4-$CH_3$ | O | NH |
| 127 | $COOCH_2CH_3$ | $CF_3$ | n-butyl | n-butyl | 2-$CH_3$ | O | NH |
| 128 | $COOCH_2CH_3$ | $CF_3$ | n-butyl | n-butyl | 4-$CH_3$ | O | NH |
| 129 | $COOCH_2CH_3$ | $CF_3$ | n-butyl | n-butyl | 2,4-2$CH_3$ | O | NH |
| 130 | $COOCH_2CH_3$ | $CF_3$ | n-butyl | n-butyl | 2-F | O | NH |
| 131 | $COOCH_2CH_3$ | $CF_3$ | n-butyl | n-butyl | 4-F | O | NH |
| 132 | $COOCH_2CH_3$ | $CF_3$ | n-butyl | n-butyl | 2,4-2F | O | NH |
| 133 | $COOCH_2CH_3$ | $CF_3$ | n-butyl | n-butyl | 2-F-4-$CH_3$ | O | NH |
| 134 | COOH | $CF_3$ | n-butyl | n-butyl | 2-$CH_3$ | O | NH |
| 135 | COOH | $CF_3$ | n-butyl | n-butyl | 4-$CH_3$ | O | NH |
| 136 | COOH | $CF_3$ | n-butyl | n-butyl | 2,4-2$CH_3$ | O | NH |
| 137 | COOH | $CF_3$ | n-butyl | n-butyl | 2-F | O | NH |
| 138 | COOH | $CF_3$ | n-butyl | n-butyl | 4-F | O | NH |
| 139 | COOH | $CF_3$ | n-butyl | n-butyl | 2,4-2F | O | NH |
| 140 | COOH | $CF_3$ | n-butyl | n-butyl | 2-F-4-$CH_3$ | O | NH |
| 141 | $CONHSO_2CH_3$ | $CF_3$ | n-butyl | n-butyl | 2-$CH_3$ | O | NH |
| 142 | $CONHSO_2CH_3$ | $CF_3$ | n-butyl | n-butyl | 4-$CH_3$ | O | NH |
| 143 | $CONHSO_2CH_3$ | $CF_3$ | n-butyl | n-butyl | 2,4-2$CH_3$ | O | NH |
| 144 | $CONHSO_2CH_3$ | $CF_3$ | n-butyl | n-butyl | 2-F | O | NH |
| 145 | $CONHSO_2CH_3$ | $CF_3$ | n-butyl | n-butyl | 4-F | O | NH |
| 146 | $CONHSO_2CH_3$ | $CF_3$ | n-butyl | n-butyl | 2,4-2F | O | NH |
| 147 | $CONHSO_2CH_3$ | $CF_3$ | n-butyl | n-butyl | 2-F-4-$CH_3$ | O | NH |
| 148 | $CONHSO_2CF_3$ | $CF_3$ | n-butyl | n-butyl | 2-$CH_3$ | O | NH |
| 149 | $CONHSO_2CF_3$ | $CF_3$ | n-butyl | n-butyl | 4-$CH_3$ | O | NH |
| 150 | $CONHSO_2CF_3$ | $CF_3$ | n-butyl | n-butyl | 2,4-2$CH_3$ | O | NH |
| 151 | $CONHSO_2CF_3$ | $CF_3$ | n-butyl | n-butyl | 2-F | O | NH |
| 152 | $CONHSO_2CF_3$ | $CF_3$ | n-butyl | n-butyl | 4-F | O | NH |
| 153 | $CONHSO_2CF_3$ | $CF_3$ | n-butyl | n-butyl | 2,4-2F | O | NH |
| 154 | $CONHSO_2CF_3$ | $CF_3$ | n-butyl | n-butyl | 2-F-4-$CH_3$ | O | NH |
| 155 | 5-tetrazolyl | $CF_3$ | n-butyl | n-butyl | 2-$CH_3$ | O | NH |
| 156 | 5-tetrazolyl | $CF_3$ | n-butyl | n-butyl | 4-$CH_3$ | O | NH |
| 157 | 5-tetrazolyl | $CF_3$ | n-butyl | n-butyl | 2,4-2$CH_3$ | O | NH |
| 158 | 5-tetrazolyl | $CF_3$ | n-butyl | n-butyl | 2-F | O | NH |
| 159 | 5-tetrazolyl | $CF_3$ | n-butyl | n-butyl | 4-F | O | NH |
| 160 | 5-tetrazolyl | $CF_3$ | n-butyl | n-butyl | 2,4-2F | O | NH |
| 161 | 5-tetrazolyl | $CF_3$ | n-butyl | n-butyl | 2-F-4-$CH_3$ | O | NH |
| 162 | 5-tetrazolyl | $CF_3$ | n-butyl | n-butyl | 2-$CH_3$ | O | NH |
| 163 | 5-tetrazolyl | $CF_3$ | n-butyl | n-butyl | 4-$CH_3$ | O | NH |
| 164 | 5-tetrazolyl | $CF_3$ | n-butyl | n-butyl | 2,4-2$CH_3$ | O | NH |
| 165 | 5-tetrazolyl | $CF_3$ | n-butyl | n-butyl | 2-F | O | NH |
| 166 | 5-tetrazolyl | $CF_3$ | n-butyl | n-butyl | 4-F | O | NH |
| 167 | 5-tetrazolyl | $CF_3$ | n-butyl | n-butyl | 2,4-2F | O | NH |
| 168 | 5-tetrazolyl | $CF_3$ | n-butyl | n-butyl | 2-F-4-$CH_3$ | O | NH |
| 169 | $COOCH_2CH_3$ | $CF_3$ | isobutyl | isobutyl | 2-$CH_3$ | O | NH |
| 170 | $COOCH_2CH_3$ | $CF_3$ | isobutyl | isobutyl | 4-$CH_3$ | O | NH |
| 171 | $COOCH_2CH_3$ | $CF_3$ | isobutyl | isobutyl | 2,4-2$CH_3$ | O | NH |
| 172 | $COOCH_2CH_3$ | $CF_3$ | isobutyl | isobutyl | 2-F | O | NH |
| 173 | $COOCH_2CH_3$ | $CF_3$ | isobutyl | isobutyl | 4-F | O | NH |
| 174 | $COOCH_2CH_3$ | $CF_3$ | isobutyl | isobutyl | 2,4-2F | O | NH |
| 175 | $COOCH_2CH_3$ | $CF_3$ | isobutyl | isobutyl | 2-F-4-$CH_3$ | O | NH |
| 176 | COOH | $CF_3$ | isobutyl | isobutyl | 2-$CH_3$ | O | NH |
| 177 | COOH | $CF_3$ | isobutyl | isobutyl | 4-$CH_3$ | O | NH |
| 178 | COOH | $CF_3$ | isobutyl | isobutyl | 2,4-2$CH_3$ | O | NH |
| 179 | COOH | $CF_3$ | isobutyl | isobutyl | 2-F | O | NH |
| 180 | COOH | $CF_3$ | isobutyl | isobutyl | 4-F | O | NH |
| 181 | COOH | $CF_3$ | isobutyl | isobutyl | 2,4-2F | O | NH |
| 182 | COOH | $CF_3$ | isobutyl | isobutyl | 2-F-4-$CH_3$ | O | NH |
| 183 | $CONHSO_2CH_3$ | $CF_3$ | isobutyl | isobutyl | 2-$CH_3$ | O | NH |
| 184 | $CONHSO_2CH_3$ | $CF_3$ | isobutyl | isobutyl | 4-$CH_3$ | O | NH |
| 185 | $CONHSO_2CH_3$ | $CF_3$ | isobutyl | isobutyl | 2,4-2$CH_3$ | O | NH |
| 186 | $CONHSO_2CH_3$ | $CF_3$ | isobutyl | isobutyl | 2-F | O | NH |
| 187 | $CONHSO_2CH_3$ | $CF_3$ | isobutyl | isobutyl | 4-F | O | NH |
| 188 | $CONHSO_2CH_3$ | $CF_3$ | isobutyl | isobutyl | 2,4-2F | O | NH |
| 189 | $CONHSO_2CH_3$ | $CF_3$ | isobutyl | isobutyl | 2-F-4-$CH_3$ | O | NH |
| 190 | $CONHSO_2CF_3$ | $CF_3$ | isobutyl | isobutyl | 2-$CH_3$ | O | NH |

TABLE 5-continued

| Compound Number | R¹ | R³ | R⁷ | R⁸ | R | Y | X |
|---|---|---|---|---|---|---|---|
| 191 | CONHSO₂CF₃ | CF₃ | isobutyl | isobutyl | 4-CH₃ | O | NH |
| 192 | CONHSO₂CF₃ | CF₃ | isobutyl | isobutyl | 2,4-2CH₃ | O | NH |
| 193 | CONHSO₂CF₃ | CF₃ | isobutyl | isobutyl | 2-F | O | NH |
| 194 | CONHSO₂CF₃ | CF₃ | isobutyl | isobutyl | 4-F | O | NH |
| 195 | CONHSO₂CF₃ | CF₃ | isobutyl | isobutyl | 2,4-2F | O | NH |
| 196 | CONHSO₂CF₃ | CF₃ | isobutyl | isobutyl | 2-F-4-CH₃ | O | NH |
| 197 | 5-tetrazolyl | CF₃ | isobutyl | isobutyl | 2-CH₃ | O | NH |
| 198 | 5-tetrazolyl | CF₃ | isobutyl | isobutyl | 4-CH₃ | O | NH |
| 199 | 5-tetrazolyl | CF₃ | isobutyl | isobutyl | 2,4-2CH₃ | O | NH |
| 200 | 5-tetrazolyl | CF₃ | isobutyl | isobutyl | 2-F | O | NH |
| 201 | 5-tetrazolyl | CF₃ | isobutyl | isobutyl | 4-F | O | NH |
| 202 | 5-tetrazolyl | CF₃ | isobutyl | isobutyl | 2,4-2F | O | NH |
| 203 | 5-tetrazolyl | CF₃ | isobutyl | isobutyl | 2-F-4-CH₃ | O | NH |
| 204 | 5-tetrazolyl | CF₃ | isobutyl | isobutyl | 2-CH₃ | O | NH |
| 205 | 5-tetrazolyl | CF₃ | isobutyl | isobutyl | 4-CH₃ | O | NH |
| 206 | 5-tetrazolyl | CF₃ | isobutyl | isobutyl | 2,4-2CH₃ | O | NH |
| 207 | 5-tetrazolyl | CF₃ | isobutyl | isobutyl | 2-F | O | NH |
| 208 | 5-tetrazolyl | CF₃ | isobutyl | isobutyl | 4-F | O | NH |
| 209 | 5-tetrazolyl | CF₃ | isobutyl | isobutyl | 2,4-2F | O | NH |
| 210 | 5-tetrazolyl | CF₃ | isobutyl | isobutyl | 2-F-4-CH₃ | O | NH |
| 211 | COOCH₂CH₃ | CF₃ | cyclohexyl | isobutyl | 2-CH₃ | O | NH |
| 212 | COOCH₂CH₃ | CF₃ | cyclohexyl | isobutyl | 4-CH₃ | O | NH |
| 213 | COOCH₂CH₃ | CF₃ | cyclohexyl | isobutyl | 2,4-2CH₃ | O | NH |
| 214 | COOCH₂CH₃ | CF₃ | cyclohexyl | isobutyl | 2-F | O | NH |
| 215 | COOCH₂CH₃ | CF₃ | cyclohexyl | isobutyl | 4-F | O | NH |
| 216 | COOCH₂CH₃ | CF₃ | cyclohexyl | isobutyl | 2,4-2F | O | NH |
| 217 | COOCH₂CH₃ | CF₃ | cyclohexyl | isobutyl | 2-F-4-CH₃ | O | NH |
| 218 | COOH | CF₃ | cyclohexyl | isobutyl | 2-CH₃ | O | NH |
| 219 | COOH | CF₃ | cyclohexyl | isobutyl | 4-CH₃ | O | NH |
| 220 | COOH | CF₃ | cyclohexyl | isobutyl | 2,4-2CH₃ | O | NH |
| 221 | COOH | CF₃ | cyclohexyl | isobutyl | 2-F | O | NH |
| 222 | COOH | CF₃ | cyclohexyl | isobutyl | 4-F | O | NH |
| 223 | COOH | CF₃ | cyclohexyl | isobutyl | 2,4-2F | O | NH |
| 224 | COOH | CF₃ | cyclohexyl | isobutyl | 2-F-4-CH₃ | O | NH |
| 225 | CONHSO₂CH₃ | CF₃ | cyclohexyl | isobutyl | 2-CH₃ | O | NH |
| 226 | CONHSO₂CH₃ | CF₃ | cyclohexyl | isobutyl | 4-CH₃ | O | NH |
| 227 | CONHSO₂CH₃ | CF₃ | cyclohexyl | isobutyl | 2,4-2CH₃ | O | NH |
| 228 | CONHSO₂CH₃ | CF₃ | cyclohexyl | isobutyl | 2-F | O | NH |
| 229 | CONHSO₂CH₃ | CF₃ | cyclohexyl | isobutyl | 4-F | O | NH |
| 230 | CONHSO₂CH₃ | CF₃ | cyclohexyl | isobutyl | 2,4-2F | O | NH |
| 231 | CONHSO₂CH₃ | CF₃ | cyclohexyl | isobutyl | 2-F-4-CH₃ | O | NH |
| 232 | CONHSO₂CF₃ | CF₃ | cyclohexyl | isobutyl | 2-CH₃ | O | NH |
| 233 | CONHSO₂CF₃ | CF₃ | cyclohexyl | isobutyl | 4-CH₃ | O | NH |
| 234 | CONHSO₂CF₃ | CF₃ | cyclohexyl | isobutyl | 2,4-2CH₃ | O | NH |
| 235 | CONHSO₂CF₃ | CF₃ | cyclohexyl | isobutyl | 2-F | O | NH |
| 236 | CONHSO₂CF₃ | CF₃ | cyclohexyl | isobutyl | 4-F | O | NH |
| 237 | CONHSO₂CF₃ | CF₃ | cyclohexyl | isobutyl | 2,4-2F | O | NH |
| 238 | CONHSO₂CF₃ | CF₃ | cyclohexyl | isobutyl | 2-F-4-CH₃ | O | NH |
| 239 | 5-tetrazolyl | CF₃ | cyclohexyl | isobutyl | 2-CH₃ | O | NH |
| 240 | 5-tetrazolyl | CF₃ | cyclohexyl | isobutyl | 4-CH₃ | O | NH |
| 241 | 5-tetrazolyl | CF₃ | cyclohexyl | isobutyl | 2,4-2CH₃ | O | NH |
| 242 | 5-tetrazolyl | CF₃ | cyclohexyl | isobutyl | 2-F | O | NH |
| 243 | 5-tetrazolyl | CF₃ | cyclohexyl | isobutyl | 4-F | O | NH |
| 244 | 5-tetrazolyl | CF₃ | cyclohexyl | isobutyl | 2,4-2F | O | NH |
| 245 | 5-tetrazolyl | CF₃ | cyclohexyl | isobutyl | 2-F-4-CH₃ | O | NH |
| 246 | 5-tetrazolyl | CF₃ | cyclohexyl | isobutyl | 2-CH₃ | O | NH |
| 247 | 5-tetrazolyl | CF₃ | cyclohexyl | isobutyl | 4-CH₃ | O | NH |
| 248 | 5-tetrazolyl | CF₃ | cyclohexyl | isobutyl | 2,4-2CH₃ | O | NH |
| 249 | 5-tetrazolyl | CF₃ | cyclohexyl | isobutyl | 2-F | O | NH |
| 250 | 5-tetrazolyl | CF₃ | cyclohexyl | isobutyl | 4-F | O | NH |
| 251 | 5-tetrazolyl | CF₃ | cyclohexyl | isobutyl | 2,4-2F | O | NH |
| 252 | 5-tetrazolyl | CF₃ | cyclohexyl | isobutyl | 2-F-4-CH₃ | O | NH |
| 253 | COOCH₂CH₃ | CH₃ | n-butyl | n-butyl | 2-CH₃ | O | CH₂ |
| 254 | COOCH₂CH₃ | CH₃ | n-butyl | n-butyl | 4-CH₃ | O | CH₂ |
| 255 | COOCH₂CH₃ | CH₃ | n-butyl | n-butyl | 2,4-2CH₃ | O | CH₂ |
| 256 | COOCH₂CH₃ | CH₃ | n-butyl | n-butyl | 2-F | O | CH₂ |
| 257 | COOCH₂CH₃ | CH₃ | n-butyl | n-butyl | 4-F | O | CH₂ |
| 258 | COOCH₂CH₃ | CH₃ | n-butyl | n-butyl | 2,4-2F | O | CH₂ |
| 259 | COOCH₂CH₃ | CH₃ | n-butyl | n-butyl | 2-F-4-CH₃ | O | CH₂ |
| 260 | COOH | CH₃ | n-butyl | n-butyl | 2-CH₃ | O | CH₂ |
| 261 | COOH | CH₃ | n-butyl | n-butyl | 4-CH₃ | O | CH₂ |
| 262 | COOH | CH₃ | n-butyl | n-butyl | 2,4-2CH₃ | O | CH₂ |
| 263 | COOH | CH₃ | n-butyl | n-butyl | 2-F | O | CH₂ |
| 264 | COOH | CH₃ | n-butyl | n-butyl | 4-F | O | CH₂ |
| 265 | COOH | CH₃ | n-butyl | n-butyl | 2,4-2F | O | CH₂ |
| 266 | COOH | CH₃ | n-butyl | n-butyl | 2-F-4-CH₃ | O | CH₂ |
| 267 | CONHSO₂CH₃ | CH₃ | n-butyl | n-butyl | 2-CH₃ | O | CH₂ |

TABLE 5-continued

| Compound Number | R¹ | R³ | R⁷ | R⁸ | R | Y | X |
|---|---|---|---|---|---|---|---|
| 268 | CONHSO₂CH₃ | CH₃ | n-butyl | n-butyl | 4-CH₃ | O | CH₂ |
| 269 | CONHSO₂CH₃ | CH₃ | n-butyl | n-butyl | 2,4-2CH₃ | O | CH₂ |
| 270 | CONHSO₂CH₃ | CH₃ | n-butyl | n-butyl | 2-F | O | CH₂ |
| 271 | CONHSO₂CH₃ | CH₃ | n-butyl | n-butyl | 4-F | O | CH₂ |
| 272 | CONHSO₂CH₃ | CH₃ | n-butyl | n-butyl | 2,4-2F | O | CH₂ |
| 273 | CONHSO₂CH₃ | CH₃ | n-butyl | n-butyl | 2-F-4-CH₃ | O | CH₂ |
| 274 | CONHSO₂CF₃ | CH₃ | n-butyl | n-butyl | 2-CH₃ | O | CH₂ |
| 275 | CONHSO₂CF₃ | CH₃ | n-butyl | n-butyl | 4-CH₃ | O | CH₂ |
| 276 | CONHSO₂CF₃ | CH₃ | n-butyl | n-butyl | 2,4-2CH3 | O | CH₂ |
| 277 | CONHSO₂CF₃ | CH₃ | n-butyl | n-butyl | 2-F | O | CH₂ |
| 278 | CONHSO₂CF₃ | CH₃ | n-butyl | n-butyl | 4-F | O | CH₂ |
| 279 | CONHSO₂CF₃ | CH₃ | n-butyl | n-butyl | 2,4-2F | O | CH₂ |
| 280 | CONHSO₂CF₃ | CH₃ | n-butyl | n-butyl | 2-F-4-CH₃ | O | CH₂ |
| 281 | 5-tetrazolyl | CH₃ | n-butyl | n-butyl | 2-CH₃ | O | CH₂ |
| 282 | 5-tetrazolyl | CH₃ | n-butyl | n-butyl | 4-CH₃ | O | CH₂ |
| 283 | 5-tetrazolyl | CH₃ | n-butyl | n-butyl | 2,4-2CH₃ | O | CH₂ |
| 284 | 5-tetrazolyl | CH₃ | n-butyl | n-butyl | 2-F | O | CH₂ |
| 285 | 5-tetrazolyl | CH₃ | n-butyl | n-butyl | 4-F | O | CH₂ |
| 286 | 5-tetrazolyl | CH₃ | n-butyl | n-butyl | 2,4-2F | O | CH₂ |
| 287 | 5-tetrazolyl | CH₃ | n-butyl | n-butyl | 2-F-4-CH₃ | O | CH₂ |
| 288 | 5-tetrazolyl | CH₃ | n-butyl | n-butyl | 2-CH₃ | O | CH₂ |
| 289 | 5-tetrazolyl | CH₃ | n-butyl | n-butyl | 4-CH₃ | O | CH₂ |
| 290 | 5-tetrazolyl | CH₃ | n-butyl | n-butyl | 2,4-2CH₃ | O | CH₂ |
| 291 | 5-tetrazolyl | CH₃ | n-butyl | n-butyl | 2-F | O | CH₂ |
| 292 | 5-tetrazolyl | CH₃ | n-butyl | n-butyl | 4-F | O | CH₂ |
| 293 | 5-tetrazolyl | CH₃ | n-butyl | n-butyl | 2,4-2F | O | CH₂ |
| 294 | 5-tetrazolyl | CH₃ | n-butyl | n-butyl | 2-F-4-CH₃ | O | CH₂ |
| 295 | COOCH₂CH₃ | CH₃ | isobutyl | isobutyl | 2-CH₃ | O | CH₂ |
| 296 | COOCH₂CH₃ | CH₃ | isobutyl | isobutyl | 4-CH₃ | O | CH₂ |
| 297 | COOCH₂CH₃ | CH₃ | isobutyl | isobutyl | 2,4-2CH₃ | O | CH₂ |
| 298 | COOCH₂CH₃ | CH₃ | isobutyl | isobutyl | 2-F | O | CH₂ |
| 299 | COOCH₂CH₃ | CH₃ | isobutyl | isobutyl | 4-F | O | CH₂ |
| 300 | COOCH₂CH₃ | CH₃ | isobutyl | isobutyl | 2,4-2F | O | CH₂ |
| 301 | COOCH₂CH₃ | CH₃ | isobutyl | isobutyl | 2-F-4-CH₃ | O | CH₂ |
| 302 | COOH | CH₃ | isobutyl | isobutyl | 2-CH₃ | O | CH₂ |
| 303 | COOH | CH₃ | isobutyl | isobutyl | 4-CH₃ | O | CH₂ |
| 304 | COOH | CH₃ | isobutyl | isobutyl | 2,4-2CH₃ | O | CH₂ |
| 305 | COOH | CH₃ | isobutyl | isobutyl | 2-F | O | CH₂ |
| 306 | COOH | CH₃ | isobutyl | isobutyl | 4-F | O | CH₂ |
| 307 | COOH | CH₃ | isobutyl | isobutyl | 2,4-2F | O | CH₂ |
| 308 | COOH | CH₃ | isobutyl | isobutyl | 2-F-4-CH₃ | O | CH₂ |
| 309 | CONHSO₂CH₃ | CH₃ | isobutyl | isobutyl | 2-CH₃ | O | CH₂ |
| 310 | CONHSO₂CH₃ | CH₃ | isobutyl | isobutyl | 4-CH₃ | O | CH₂ |
| 311 | CONHSO₂CH₃ | CH₃ | isobutyl | isobutyl | 2,4-2CH₃ | O | CH₂ |
| 312 | CONHSO₂CH₃ | CH₃ | isobutyl | isobutyl | 2-F | O | CH₂ |
| 313 | CONHSO₂CH₃ | CH₃ | isobutyl | isobutyl | 4-F | O | CH₂ |
| 314 | CONHSO₂CH₃ | CH₃ | isobutyl | isobutyl | 2,4-2F | O | CH₂ |
| 315 | CONHSO₂CH₃ | CH₃ | isobutyl | isobutyl | 2-F-4-CH₃ | O | CH₂ |
| 316 | CONHSO₂CF₃ | CH₃ | isobutyl | isobutyl | 2-CH₃ | O | CH₂ |
| 317 | CONHSO₂CF₃ | CH₃ | isobutyl | isobutyl | 4-CH₃ | O | CH₂ |
| 318 | CONHSO₂CF₃ | CH₃ | isobutyl | isobutyl | 2,4-2CH₃ | O | CH₂ |
| 319 | CONHSO₂CF₃ | CH₃ | isobutyl | isobutyl | 2-F | O | CH₂ |
| 320 | CONHSO₂CF₃ | CH₃ | isobutyl | isobutyl | 4-F | O | CH₂ |
| 321 | CONHSO₂CF₃ | CH₃ | isobutyl | isobutyl | 2,4-2F | O | CH₂ |
| 322 | CONHSO₂CF₃ | CH₃ | isobutyl | isobutyl | 2-F-4-CH₃ | O | CH₂ |
| 323 | 5-tetrazolyl | CH₃ | isobutyl | isobutyl | 2-CH₃ | O | CH₂ |
| 324 | 5-tetrazolyl | CH₃ | isobutyl | isobutyl | 4-CH₃ | O | CH₂ |
| 325 | 5-tetrazolyl | CH₃ | isobutyl | isobutyl | 2,4-2CH₃ | O | CH₂ |
| 326 | 5-tetrazolyl | CH₃ | isobutyl | isobutyl | 2-F | O | CH₂ |
| 327 | 5-tetrazolyl | CH₃ | isobutyl | isobutyl | 4-F | O | CH₂ |
| 328 | 5-tetrazolyl | CH₃ | isobutyl | isobutyl | 2,4-2F | O | CH₂ |
| 329 | 5-tetrazolyl | CH₃ | isobutyl | isobutyl | 2-F-4-CH₃ | O | CH₂ |
| 330 | 5-tetrazolyl | CH₃ | isobutyl | isobutyl | 2-CH₃ | O | CH₂ |
| 331 | 5-tetrazolyl | CH₃ | isobutyl | isobutyl | 4-CH₃ | O | CH₂ |
| 332 | 5-tetrazolyl | CH₃ | isobutyl | isobutyl | 2,4-2CH₃ | O | CH₂ |
| 333 | 5-tetrazolyl | CH₃ | isobutyl | isobutyl | 2-F | O | CH₂ |
| 334 | 5-tetrazolyl | CH₃ | isobutyl | isobutyl | 4-F | O | CH₂ |
| 335 | 5-tetrazolyl | CH₃ | isobutyl | isobutyl | 2,4-2F | O | CH₂ |
| 336 | 5-tetrazolyl | CH₃ | isobutyl | isobutyl | 2-F-4-CH₃ | O | CH₂ |
| 337 | COOCH₂CH₃ | CH₃ | cyclohexyl | isobutyl | 2-CH₃ | O | CH₂ |
| 338 | COOCH₂CH₃ | CH₃ | cyclohexyl | isobutyl | 4-CH₃ | O | CH₂ |
| 339 | COOCH₂CH₃ | CH₃ | cyclohexyl | isobutyl | 2,4-2CH₃ | O | CH₂ |
| 340 | COOCH₂CH₃ | CH₃ | cyclohexyl | isobutyl | 2-F | O | CH₂ |
| 341 | COOCH₂CH₃ | CH₃ | cyclohexyl | isobutyl | 4-F | O | CH₂ |
| 342 | COOCH₂CH₃ | CH₃ | cyclohexyl | isobutyl | 2,4-2F | O | CH₂ |
| 343 | COOCH₂CH₃ | CH₃ | cyclohexyl | isobutyl | 2-F-4-CH₃ | O | CH₂ |
| 344 | COOH | CH₃ | cyclohexyl | isobutyl | 2-CH₃ | O | CH₂ |

TABLE 5-continued

| Compound Number | $R^1$ | $R^3$ | $R^7$ | $R^8$ | R | Y | X |
|---|---|---|---|---|---|---|---|
| 345 | COOH | $CH_3$ | cyclohexyl | isobutyl | 4-$CH_3$ | O | $CH_2$ |
| 346 | COOH | $CH_3$ | cyclohexyl | isobutyl | 2,4-2$CH_3$ | O | $CH_2$ |
| 347 | COOH | $CH_3$ | cyclohexyl | isobutyl | 2-F | O | $CH_2$ |
| 348 | COOH | $CH_3$ | cyclohexyl | isobutyl | 4-F | O | $CH_2$ |
| 349 | COOH | $CH_3$ | cyclohexyl | isobutyl | 2,4-2F | O | $CH_2$ |
| 350 | COOH | $CH_3$ | cyclohexyl | isobutyl | 2-F-4-$CH_3$ | O | $CH_2$ |
| 351 | $CONHSO_2CH_3$ | $CH_3$ | cyclohexyl | isobutyl | 2-$CH_3$ | O | $CH_2$ |
| 352 | $CONHSO_2CH_3$ | $CH_3$ | cyclohexyl | isobutyl | 4-$CH_3$ | O | $CH_2$ |
| 353 | $CONHSO_2CH_3$ | $CH_3$ | cyclohexyl | isobutyl | 2,4-2$CH_3$ | O | $CH_2$ |
| 354 | $CONHSO_2CH_3$ | $CH_3$ | cyclohexyl | isobutyl | 2-F | O | $CH_2$ |
| 355 | $CONHSO_2CH_3$ | $CH_3$ | cyclohexyl | isobutyl | 4-F | O | $CH_2$ |
| 356 | $CONHSO_2CH_3$ | $CH_3$ | cyclohexyl | isobutyl | 2,4-2F | O | $CH_2$ |
| 357 | $CONHSO_2CH_3$ | $CH_3$ | cyclohexyl | isobutyl | 2-F-4-$CH_3$ | O | $CH_2$ |
| 358 | $CONHSO_2CF_3$ | $CH_3$ | cyclohexyl | isobutyl | 2-$CH_3$ | O | $CH_2$ |
| 359 | $CONHSO_2CF_3$ | $CH_3$ | cyclohexyl | isobutyl | 4-$CH_3$ | O | $CH_2$ |
| 360 | $CONHSO_2CF_3$ | $CH_3$ | cyclohexyl | isobutyl | 2,4-2$CH_3$ | O | $CH_2$ |
| 361 | $CONHSO_2CF_3$ | $CH_3$ | cyclohexyl | isobutyl | 2-F | O | $CH_2$ |
| 362 | $CONHSO_2CF_3$ | $CH_3$ | cyclohexyl | isobutyl | 4-F | O | $CH_2$ |
| 363 | $CONHSO_2CF_3$ | $CH_3$ | cyclohexyl | isobutyl | 2,4-2F | O | $CH_2$ |
| 364 | $CONHSO_2CF_3$ | $CH_3$ | cyclohexyl | isobutyl | 2-F-4-$CH_3$ | O | $CH_2$ |
| 365 | 5-tetrazolyl | $CH_3$ | cyclohexyl | isobutyl | 2-$CH_3$ | O | $CH_2$ |
| 366 | 5-tetrazolyl | $CH_3$ | cyclohexyl | isobutyl | 4-$CH_3$ | O | $CH_2$ |
| 367 | 5-tetrazolyl | $CH_3$ | cyclohexyl | isobutyl | 2,4-2$CH_3$ | O | $CH_2$ |
| 368 | 5-tetrazolyl | $CH_3$ | cyclohexyl | isobutyl | 2-F | O | $CH_2$ |
| 369 | 5-tetrazolyl | $CH_3$ | cyclohexyl | isobutyl | 4-F | O | $CH_2$ |
| 370 | 5-tetrazolyl | $CH_3$ | cyclohexyl | isobutyl | 2,4-2F | O | $CH_2$ |
| 371 | 5-tetrazolyl | $CH_3$ | cyclohexyl | isobutyl | 2-F-4-$CH_3$ | O | $CH_2$ |
| 372 | 5-tetrazolyl | $CH_3$ | cyclohexyl | isobutyl | 2-$CH_3$ | O | $CH_2$ |
| 373 | 5-tetrazolyl | $CH_3$ | cyclohexyl | isobutyl | 4-$CH_3$ | O | $CH_2$ |
| 374 | 5-tetrazolyl | $CH_3$ | cyclohexyl | isobutyl | 2,4-2$CH_3$ | O | $CH_2$ |
| 375 | 5-tetrazolyl | $CH_3$ | cyclohexyl | isobutyl | 2-F | O | $CH_2$ |
| 376 | 5-tetrazolyl | $CH_3$ | cyclohexyl | isobutyl | 4-F | O | $CH_2$ |
| 377 | 5-tetrazolyl | $CH_3$ | cyclohexyl | isobutyl | 2,4-2F | O | $CH_2$ |
| 378 | 5-tetrazolyl | $CH_3$ | cyclohexyl | isobutyl | 2-F-4-$CH_3$ | O | $CH_2$ |
| 379 | $COOCH_2CH_3$ | $CF_3$ | n-butyl | n-butyl | 2-$CH_3$ | O | $CH_2$ |
| 380 | $COOCH_2CH_3$ | $CF_3$ | n-butyl | n-butyl | 4-$CH_3$ | O | $CH_2$ |
| 381 | $COOCH_2CH_3$ | $CF_3$ | n-butyl | n-butyl | 2,4-2$CH_3$ | O | $CH_2$ |
| 382 | $COOCH_2CH_3$ | $CF_3$ | n-butyl | n-butyl | 2-F | O | $CH_2$ |
| 383 | $COOCH_2CH_3$ | $CF_3$ | n-butyl | n-butyl | 4-F | O | $CH_2$ |
| 384 | $COOCH_2CH_3$ | $CF_3$ | n-butyl | n-butyl | 2,4-2F | O | $CH_2$ |
| 385 | $COOCH_2CH_3$ | $CF_3$ | n-butyl | n-butyl | 2-F-4-$CH_3$ | O | $CH_2$ |
| 386 | COOH | $CF_3$ | n-butyl | n-butyl | 2-$CH_3$ | O | $CH_2$ |
| 387 | COOH | $CF_3$ | n-butyl | n-butyl | 4-$CH_3$ | O | $CH_2$ |
| 388 | COOH | $CF_3$ | n-butyl | n-butyl | 2,4-2$CH_3$ | O | $CH_2$ |
| 389 | COOH | $CF_3$ | n-butyl | n-butyl | 2-F | O | $CH_2$ |
| 390 | COOH | $CF_3$ | n-butyl | n-butyl | 4-F | O | $CH_2$ |
| 391 | COOH | $CF_3$ | n-butyl | n-butyl | 2,4-2F | O | $CH_2$ |
| 392 | COOH | $CF_3$ | n-butyl | n-butyl | 2-F-4-$CH_3$ | O | $CH_2$ |
| 393 | $CONHSO_2CH_3$ | $CF_3$ | n-butyl | n-butyl | 2-$CH_3$ | O | $CH_2$ |
| 394 | $CONHSO_2CH_3$ | $CF_3$ | n-butyl | n-butyl | 4-$CH_3$ | O | $CH_2$ |
| 395 | $CONHSO_2CH_3$ | $CF_3$ | n-butyl | n-butyl | 2,4-2$CH_3$ | O | $CH_2$ |
| 396 | $CONHSO_2CH_3$ | $CF_3$ | n-butyl | n-butyl | 2-F | O | $CH_2$ |
| 397 | $CONHSO_2CH_3$ | $CF_3$ | n-butyl | n-butyl | 4-F | O | $CH_2$ |
| 398 | $CONHSO_2CH_3$ | $CF_3$ | n-butyl | n-butyl | 2,4-2F | O | $CH_2$ |
| 399 | $CONHSO_2CH_3$ | $CF_3$ | n-butyl | n-butyl | 2-F-4-$CH_3$ | O | $CH_2$ |
| 400 | $CONHSO_2CF_3$ | $CF_3$ | n-butyl | n-butyl | 2-$CH_3$ | O | $CH_2$ |
| 401 | $CONHSO_2CF_3$ | $CF_3$ | n-butyl | n-butyl | 4-$CH_3$ | O | $CH_2$ |
| 402 | $CONHSO_2CF_3$ | $CF_3$ | n-butyl | n-butyl | 2,4-2CH3 | O | $CH_2$ |
| 403 | $CONHSO_2CF_3$ | $CF_3$ | n-butyl | n-butyl | 2-F | O | $CH_2$ |
| 404 | $CONHSO_2CF_3$ | $CF_3$ | n-butyl | n-butyl | 4-F | O | $CH_2$ |
| 405 | $CONHSO_2CF_3$ | $CF_3$ | n-butyl | n-butyl | 2,4-2F | O | $CH_2$ |
| 406 | $CONHSO_2CF_3$ | $CF_3$ | n-butyl | n-butyl | 2-F-4-$CH_3$ | O | $CH_2$ |
| 407 | 5-tetrazolyl | $CF_3$ | n-butyl | n-butyl | 2-$CH_3$ | O | $CH_2$ |
| 408 | 5-tetrazolyl | $CF_3$ | n-butyl | n-butyl | 4-$CH_3$ | O | $CH_2$ |
| 409 | 5-tetrazolyl | $CF_3$ | n-butyl | n-butyl | 2,4-2$CH_3$ | O | $CH_2$ |
| 410 | 5-tetrazolyl | $CF_3$ | n-butyl | n-butyl | 2-F | O | $CH_2$ |
| 411 | 5-tetrazolyl | $CF_3$ | n-butyl | n-butyl | 4-F | O | $CH_2$ |
| 412 | 5-tetrazolyl | $CF_3$ | n-butyl | n-butyl | 2,4-2F | O | $CH_2$ |
| 413 | 5-tetrazolyl | $CF_3$ | n-butyl | n-butyl | 2-F-4-$CH_3$ | O | $CH_2$ |
| 414 | 5-tetrazolyl | $CF_3$ | n-butyl | n-butyl | 2-$CH_3$ | O | $CH_2$ |
| 415 | 5-tetrazolyl | $CF_3$ | n-butyl | n-butyl | 4-$CH_3$ | O | $CH_2$ |
| 416 | 5-tetrazolyl | $CF_3$ | n-butyl | n-butyl | 2,4-2$CH_3$ | O | $CH_2$ |
| 417 | 5-tetrazolyl | $CF_3$ | n-butyl | n-butyl | 2-F | O | $CH_2$ |
| 418 | 5-tetrazolyl | $CF_3$ | n-butyl | n-butyl | 4-F | O | $CH_2$ |
| 419 | 5-tetrazolyl | $CF_3$ | n-butyl | n-butyl | 2,4-2F | O | $CH_2$ |
| 420 | 5-tetrazolyl | $CF_3$ | n-butyl | n-butyl | 2-F-4-$CH_3$ | O | $CH_2$ |
| 421 | $COOCH_2CH_3$ | $CF_3$ | isobutyl | isobutyl | 2-$CH_3$ | O | $CH_2$ |

TABLE 5-continued

| Compound Number | $R^1$ | $R^3$ | $R^7$ | $R^8$ | R | Y | X |
|---|---|---|---|---|---|---|---|
| 422 | COOCH$_2$CH$_3$ | CF$_3$ | isobutyl | isobutyl | 4-CH$_3$ | O | CH$_2$ |
| 423 | COOCH$_2$CH$_3$ | CF$_3$ | isobutyl | isobutyl | 2,4-2CH$_3$ | O | CH$_2$ |
| 424 | COOCH$_2$CH$_3$ | CF$_3$ | isobutyl | isobutyl | 2-F | O | CH$_2$ |
| 425 | COOCH$_2$CH$_3$ | CF$_3$ | isobutyl | isobutyl | 4-F | O | CH$_2$ |
| 426 | COOCH$_2$CH$_3$ | CF$_3$ | isobutyl | isobutyl | 2,4-2F | O | CH$_2$ |
| 427 | COOCH$_2$CH$_3$ | CF$_3$ | isobutyl | isobutyl | 2-F-4-CH$_3$ | O | CH$_2$ |
| 428 | COOH | CF$_3$ | isobutyl | isobutyl | 2-CH$_3$ | O | CH$_2$ |
| 429 | COOH | CF$_3$ | isobutyl | isobutyl | 4-CH$_3$ | O | CH$_2$ |
| 430 | COOH | CF$_3$ | isobutyl | isobutyl | 2,4-2CH$_3$ | O | CH$_2$ |
| 431 | COOH | CF$_3$ | isobutyl | isobutyl | 2-F | O | CH$_2$ |
| 432 | COOH | CF$_3$ | isobutyl | isobutyl | 4-F | O | CH$_2$ |
| 433 | COOH | CF$_3$ | isobutyl | isobutyl | 2,4-2F | O | CH$_2$ |
| 434 | COOH | CF$_3$ | isobutyl | isobutyl | 2-F-4-CH$_3$ | O | CH$_2$ |
| 435 | CONHSO$_2$CH$_3$ | CF$_3$ | isobutyl | isobutyl | 2-CH$_3$ | O | CH$_2$ |
| 436 | CONHSO$_2$CH$_3$ | CF$_3$ | isobutyl | isobutyl | 4-CH$_3$ | O | CH$_2$ |
| 437 | CONHSO$_2$CH$_3$ | CF$_3$ | isobutyl | isobutyl | 2,4-2CH$_3$ | O | CH$_2$ |
| 438 | CONHSO$_2$CH$_3$ | CF$_3$ | isobutyl | isobutyl | 2-F | O | CH$_2$ |
| 439 | CONHSO$_2$CH$_3$ | CF$_3$ | isobutyl | isobutyl | 4-F | O | CH$_2$ |
| 440 | CONHSO$_2$CH$_3$ | CF$_3$ | isobutyl | isobutyl | 2,4-2F | O | CH$_2$ |
| 441 | CONHSO$_2$CH$_3$ | CF$_3$ | isobutyl | isobutyl | 2-F-4-CH$_3$ | O | CH$_2$ |
| 442 | CONHSO$_2$CF$_3$ | CF$_3$ | isobutyl | isobutyl | 2-CH$_3$ | O | CH$_2$ |
| 443 | CONHSO$_2$CF$_3$ | CF$_3$ | isobutyl | isobutyl | 4-CH$_3$ | O | CH$_2$ |
| 444 | CONHSO$_2$CF$_3$ | CF$_3$ | isobutyl | isobutyl | 2,4-2CH$_3$ | O | CH$_2$ |
| 445 | CONHSO$_2$CF$_3$ | CF$_3$ | isobutyl | isobutyl | 2-F | O | CH$_2$ |
| 446 | CONHSO$_2$CF$_3$ | CF$_3$ | isobutyl | isobutyl | 4-F | O | CH$_2$ |
| 447 | CONHSO$_2$CF$_3$ | CF$_3$ | isobutyl | isobutyl | 2,4-2F | O | CH$_2$ |
| 448 | CONHSO$_2$CF$_3$ | CF$_3$ | isobutyl | isobutyl | 2-F-4-CH$_3$ | O | CH$_2$ |
| 449 | 5-tetrazolyl | CF$_3$ | isobutyl | isobutyl | 2-CH$_3$ | O | CH$_2$ |
| 450 | 5-tetrazolyl | CF$_3$ | isobutyl | isobutyl | 4-CH$_3$ | O | CH$_2$ |
| 451 | 5-tetrazolyl | CF$_3$ | isobutyl | isobutyl | 2,4-2CH$_3$ | O | CH$_2$ |
| 452 | 5-tetrazolyl | CF$_3$ | isobutyl | isobutyl | 2-F | O | CH$_2$ |
| 453 | 5-tetrazolyl | CF$_3$ | isobutyl | isobutyl | 4-F | O | CH$_2$ |
| 454 | 5-tetrazolyl | CF$_3$ | isobutyl | isobutyl | 2,4-2F | O | CH$_2$ |
| 455 | 5-tetrazolyl | CF$_3$ | isobutyl | isobutyl | 2-F-4-CH$_3$ | O | CH$_2$ |
| 456 | 5-tetrazolyl | CF$_3$ | isobutyl | isobutyl | 2-CH$_3$ | O | CH$_2$ |
| 457 | 5-tetrazolyl | CF$_3$ | isobutyl | isobutyl | 4-CH$_3$ | O | CH$_2$ |
| 458 | 5-tetrazolyl | CF$_3$ | isobutyl | isobutyl | 2,4-2CH$_3$ | O | CH$_2$ |
| 459 | 5-tetrazolyl | CF$_3$ | isobutyl | isobutyl | 2-F | O | CH$_2$ |
| 460 | 5-tetrazolyl | CF$_3$ | isobutyl | isobutyl | 4-F | O | CH$_2$ |
| 461 | 5-tetrazolyl | CF$_3$ | isobutyl | isobutyl | 2,4-2F | O | CH$_2$ |
| 462 | 5-tetrazolyl | CF$_3$ | isobutyl | isobutyl | 2-F-4-CH$_3$ | O | CH$_2$ |
| 463 | COOCH$_2$CH$_3$ | CF$_3$ | isobutyl | isobutyl | 2-CH$_3$ | O | CH$_2$ |
| 464 | COOCH$_2$CH$_3$ | CF$_3$ | cyclohexyl | isobutyl | 4-CH$_3$ | O | CH$_2$ |
| 465 | COOCH$_2$CH$_3$ | CF$_3$ | cyclohexyl | isobutyl | 2,4-2CH$_3$ | O | CH$_2$ |
| 466 | COOCH$_2$CH$_3$ | CF$_3$ | cyclohexyl | isobutyl | 2-F | O | CH$_2$ |
| 467 | COOCH$_2$CH$_3$ | CF$_3$ | cyclohexyl | isobutyl | 4-F | O | CH$_2$ |
| 468 | COOCH$_2$CH$_3$ | CF$_3$ | cyclohexyl | isobutyl | 2,4-2F | O | CH$_2$ |
| 469 | COOCH$_2$CH$_3$ | CF$_3$ | cyclohexyl | isobutyl | 2-F-4-CH$_3$ | O | CH$_2$ |
| 470 | COOH | CF$_3$ | cyclohexyl | isobutyl | 2-CH$_3$ | O | CH$_2$ |
| 471 | COOH | CF$_3$ | cyclohexyl | isobutyl | 4-CH$_3$ | O | CH$_2$ |
| 472 | COOH | CF$_3$ | cyclohexyl | isobutyl | 2,4-2CH$_3$ | O | CH$_2$ |
| 473 | COOH | CF$_3$ | cyclohexyl | isobutyl | 2-F | O | CH$_2$ |
| 474 | COOH | CF$_3$ | cyclohexyl | isobutyl | 4-F | O | CH$_2$ |
| 475 | COOH | CF$_3$ | cyclohexyl | isobutyl | 2,4-2F | O | CH$_2$ |
| 476 | COOH | CF$_3$ | cyclohexyl | isobutyl | 2-F-4-CH$_3$ | O | CH$_2$ |
| 477 | CONHSO$_2$CH$_3$ | CF$_3$ | cyclohexyl | isobutyl | 2-CH$_3$ | O | CH$_2$ |
| 478 | CONHSO$_2$CH$_3$ | CF$_3$ | cyclohexyl | isobutyl | 4-CH$_3$ | O | CH$_2$ |
| 479 | CONHSO$_2$CH$_3$ | CF$_3$ | cyclohexyl | isobutyl | 2,4-2CH$_3$ | O | CH$_2$ |
| 480 | CONHSO$_2$CH$_3$ | CF$_3$ | cyclohexyl | isobutyl | 2-F | O | CH$_2$ |
| 481 | CONHSO$_2$CH$_3$ | CF$_3$ | cyclohexyl | isobutyl | 4-F | O | CH$_2$ |
| 482 | CONHSO$_2$CH$_3$ | CF$_3$ | cyclohexyl | isobutyl | 2,4-2F | O | CH$_2$ |
| 483 | CONHSO$_2$CH$_3$ | CF$_3$ | cyclohexyl | isobutyl | 2-F-4-CH$_3$ | O | CH$_2$ |
| 484 | CONHSO$_2$CF$_3$ | CF$_3$ | cyclohexyl | isobutyl | 2-CH$_3$ | O | CH$_2$ |
| 485 | CONHSO$_2$CF$_3$ | CF$_3$ | cyclohexyl | isobutyl | 2-CH$_3$ | O | CH$_2$ |
| 486 | CONHSO$_2$CF$_3$ | CF$_3$ | cyclohexyl | isobutyl | 2,4-2CH$_3$ | O | CH$_2$ |
| 487 | CONHSO$_2$CF$_3$ | CF$_3$ | cyclohexyl | isobutyl | 2-F | O | CH$_2$ |
| 488 | CONHSO$_2$CF$_3$ | CF$_3$ | cyclohexyl | isobutyl | 4-F | O | CH$_2$ |
| 489 | CONHSO$_2$CF$_3$ | CF$_3$ | cyclohexyl | isobutyl | 2,4-2F | O | CH$_2$ |
| 490 | CONHSO$_2$CF$_3$ | CF$_3$ | cyclohexyl | isobutyl | 2-F-4-CH$_3$ | O | CH$_2$ |
| 491 | 5-tetrazolyl | CF$_3$ | cyclohexyl | isobutyl | 2-CH$_3$ | O | CH$_2$ |
| 492 | 5-tetrazolyl | CF$_3$ | cyclohexyl | isobutyl | 4-CH$_3$ | O | CH$_2$ |
| 493 | 5-tetrazolyl | CF$_3$ | cyclohexyl | isobutyl | 2,4-2CH$_3$ | O | CH$_2$ |
| 494 | 5-tetrazolyl | CF$_3$ | cyclohexyl | isobutyl | 2-F | O | CH$_2$ |
| 495 | 5-tetrazolyl | CF$_3$ | cyclohexyl | isobutyl | 4-F | O | CH$_2$ |
| 496 | 5-tetrazolyl | CF$_3$ | cyclohexyl | isobutyl | 2,4-2F | O | CH$_2$ |
| 497 | 5-tetrazolyl | CF$_3$ | cyclohexyl | isobutyl | 2-F-4-CH$_3$ | O | CH$_2$ |
| 498 | 5-tetrazolyl | CF$_3$ | cyclohexyl | isobutyl | 2-CH$_3$ | O | CH$_2$ |

TABLE 5-continued

| Compound Number | R¹ | R³ | R⁷ | R⁸ | R | Y | X |
|---|---|---|---|---|---|---|---|
| 499 | 5-tetrazolyl | $CF_3$ | cyclohexyl | isobutyl | 4-$CH_3$ | O | $CH_2$ |
| 500 | 5-tetrazolyl | $CF_3$ | cyclohexyl | isobutyl | 2,4-2$CH_3$ | O | $CH_2$ |
| 501 | 5-tetrazolyl | $CF_3$ | cyclohexyl | isobutyl | 2-F | O | $CH_2$ |
| 502 | 5-tetrazolyl | $CF_3$ | cyclohexyl | isobutyl | 4-F | O | $CH_2$ |
| 503 | 5-tetrazolyl | $CF_3$ | cyclohexyl | isobutyl | 2,4-2F | O | $CH_2$ |
| 504 | 5-tetrazolyl | $CF_3$ | cyclohexyl | isobutyl | 2-F-4-$CH_3$ | O | $CH_2$ |
| 505 | $COOCH_2CH_3$ | $CH_3$ | n-butyl | n-butyl | 2-Cl | O | NH |
| 506 | $COOCH_2CH_3$ | $CH_3$ | n-butyl | n-butyl | 3-Cl | O | NH |
| 507 | $COOCH_2CH_3$ | $CH_3$ | n-butyl | n-butyl | 4-Cl | O | NH |
| 508 | $COOCH_2CH_3$ | $CH_3$ | n-butyl | n-butyl | 3-$CF_3$-4-Cl | O | NH |
| 509 | $COOCH_2CH_3$ | $CH_3$ | n-butyl | n-butyl | H | S | NH |
| 510 | $COOCH_2CH_3$ | $CH_3$ | n-butyl | n-butyl | 3-$CH_3$ | O | NH |
| 511 | COOH | $CH_3$ | n-butyl | n-butyl | 2-Cl | O | NH |
| 512 | COOH | $CH_3$ | n-butyl | n-butyl | 3-Cl | O | NH |
| 513 | COOH | $CH_3$ | n-butyl | n-butyl | 4-Cl | O | NH |
| 514 | COOH | $CH_3$ | n-butyl | n-butyl | 3-$CF_3$-4-Cl | O | NH |
| 515 | COOH | $CH_3$ | n-butyl | n-butyl | H | S | NH |
| 516 | COOH | $CH_3$ | n-butyl | n-butyl | 3-$CH_3$ | O | NH |

In the present invention, the specific compound in formula I which inhibits the activity of the IDO enzyme is shown as formula III, The specific compound listed in table 6, but the present invention is not limited by these compounds.

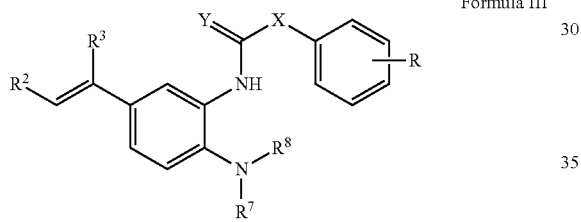

Formula III

TABLE 6

| Compound Number | R² | R¹ | R⁷ | R⁸ | R | Y | X |
|---|---|---|---|---|---|---|---|
| 517 | $COOCH_2CH_3$ | $CH_3$ | n-butyl | n-butyl | 2-$CH_3$ | O | NH |
| 518 | $COOCH_2CH_3$ | $CH_3$ | n-butyl | n-butyl | 4-$CH_3$ | O | NH |
| 519 | $COOCH_2CH_3$ | $CH_3$ | n-butyl | n-butyl | 2,4-2$CH_3$ | O | NH |
| 520 | $COOCH_2CH_3$ | $CH_3$ | n-butyl | n-butyl | 2-F | O | NH |
| 521 | $COOCH_2CH_3$ | $CH_3$ | n-butyl | n-butyl | 4-F | O | NH |
| 522 | $COOCH_2CH_3$ | $CH_3$ | n-butyl | n-butyl | 2,4-2F | O | NH |
| 523 | $COOCH_2CH_3$ | $CH_3$ | n-butyl | n-butyl | 2-F-4-$CH_3$ | O | NH |
| 524 | COOH | $CH_3$ | n-butyl | n-butyl | 2-$CH_3$ | O | NH |
| 525 | COOH | $CH_3$ | n-butyl | n-butyl | 4-$CH_3$ | O | NH |
| 526 | COOH | $CH_3$ | n-butyl | n-butyl | 2,4-2$CH_3$ | O | NH |
| 527 | COOH | $CH_3$ | n-butyl | n-butyl | 2-F | O | NH |
| 528 | COOH | $CH_3$ | n-butyl | n-butyl | 4-F | O | NH |
| 529 | COOH | $CH_3$ | n-butyl | n-butyl | 2,4-2F | O | NH |
| 530 | COOH | $CH_3$ | n-butyl | n-butyl | 2-F-4-$CH_3$ | O | NH |
| 531 | $CONHSO_2CH_3$ | $CH_3$ | n-butyl | n-butyl | 2-$CH_3$ | O | NH |
| 532 | $CONHSO_2CH_3$ | $CH_3$ | n-butyl | n-butyl | 4-$CH_3$ | O | NH |
| 533 | $CONHSO_2CH_3$ | $CH_3$ | n-butyl | n-butyl | 2,4-2$CH_3$ | O | NH |
| 534 | $CONHSO_2CH_3$ | $CH_3$ | n-butyl | n-butyl | 2-F | O | NH |
| 535 | $CONHSO_2CH_3$ | $CH_3$ | n-butyl | n-butyl | 4-F | O | NH |
| 536 | $CONHSO_2CH_3$ | $CH_3$ | n-butyl | n-butyl | 2,4-2F | O | NH |
| 537 | $CONHSO_2CH_3$ | $CH_3$ | n-butyl | n-butyl | 2-F-4-$CH_3$ | O | NH |
| 538 | $CONHSO_2CF_3$ | $CH_3$ | n-butyl | n-butyl | 2-$CH_3$ | O | NH |
| 539 | $CONHSO_2CF_3$ | $CH_3$ | n-butyl | n-butyl | 4-$CH_3$ | O | NH |
| 540 | $CONHSO_2CF_3$ | $CH_3$ | n-butyl | n-butyl | 2,4-2$CH_3$ | O | NH |
| 541 | $CONHSO_2CF_3$ | $CH_3$ | n-butyl | n-butyl | 2-F | O | NH |
| 542 | $CONHSO_2CF_3$ | $CH_3$ | n-butyl | n-butyl | 4-F | O | NH |
| 543 | $CONHSO_2CF_3$ | $CH_3$ | n-butyl | n-butyl | 2,4-2F | O | NH |
| 544 | $CONHSO_2CF_3$ | $CH_3$ | n-butyl | n-butyl | 2-F-4-$CH_3$ | O | NH |
| 545 | 5-tetrazolyl | $CH_3$ | n-butyl | n-butyl | 2-$CH_3$ | O | NH |

TABLE 6-continued

| Compound Number | R² | R¹ | R⁷ | R⁸ | R | Y | X |
|---|---|---|---|---|---|---|---|
| 546 | 5-tetrazolyl | CH₃ | n-butyl | n-butyl | 4-CH₃ | O | NH |
| 547 | 5-tetrazolyl | CH₃ | n-butyl | n-butyl | 2,4-2CH₃ | O | NH |
| 548 | 5-tetrazolyl | CH₃ | n-butyl | n-butyl | 2-F | O | NH |
| 549 | 5-tetrazolyl | CH₃ | n-butyl | n-butyl | 4-F | O | NH |
| 550 | 5-tetrazolyl | CH₃ | n-butyl | n-butyl | 2,4-2F | O | NH |
| 551 | 5-tetrazolyl | CH₃ | n-butyl | n-butyl | 2-F-4-CH₃ | O | NH |
| 552 | 5-tetrazolyl | CH₃ | n-butyl | n-butyl | 2-CH₃ | O | NH |
| 553 | 5-tetrazolyl | CH₃ | n-butyl | n-butyl | 4-CH₃ | O | NH |
| 554 | 5-tetrazolyl | CH₃ | n-butyl | n-butyl | 2,4-2CH₃ | O | NH |
| 555 | 5-tetrazolyl | CH₃ | n-butyl | n-butyl | 2-F | O | NH |
| 556 | 5-tetrazolyl | CH₃ | n-butyl | n-butyl | 4-F | O | NH |
| 557 | 5-tetrazolyl | CH₃ | n-butyl | n-butyl | 2,4-2F | O | NH |
| 558 | 5-tetrazolyl | CH₃ | n-butyl | n-butyl | 2-F-4-CH₃ | O | NH |
| 559 | COOCH₂CH₃ | CH₃ | isobutyl | isobutyl | 2-CH₃ | O | NH |
| 560 | COOCH₂CH₃ | CH₃ | isobutyl | isobutyl | 4-CH₃ | O | NH |
| 561 | COOCH₂CH₃ | CH₃ | isobutyl | isobutyl | 2,4-2CH₃ | O | NH |
| 562 | COOCH₂CH₃ | CH₃ | isobutyl | isobutyl | 2-F | O | NH |
| 563 | COOCH₂CH₃ | CH₃ | isobutyl | isobutyl | 4-F | O | NH |
| 564 | COOCH₂CH₃ | CH₃ | isobutyl | isobutyl | 2,4-2F | O | NH |
| 565 | COOCH₂CH₃ | CH₃ | isobutyl | isobutyl | 2-F-4-CH₃ | O | NH |
| 566 | COOH | CH₃ | isobutyl | isobutyl | 2-CH₃ | O | NH |
| 567 | COOH | CH₃ | isobutyl | isobutyl | 4-CH₃ | O | NH |
| 568 | COOH | CH₃ | isobutyl | isobutyl | 2,4-2CH₃ | O | NH |
| 569 | COOH | CH₃ | isobutyl | isobutyl | 2-F | O | NH |
| 570 | COOH | CH₃ | isobutyl | isobutyl | 4-F | O | NH |
| 571 | COOH | CH₃ | isobutyl | isobutyl | 2,4-2F | O | NH |
| 572 | COOH | CH₃ | isobutyl | isobutyl | 2-F-4-CH₃ | O | NH |
| 573 | CONHSO₂CH₃ | CH₃ | isobutyl | isobutyl | 2-CH₃ | O | NH |
| 574 | CONHSO₂CH₃ | CH₃ | isobutyl | isobutyl | 4-CH₃ | O | NH |
| 575 | CONHSO₂CH₃ | CH₃ | isobutyl | isobutyl | 2,4-2CH₃ | O | NH |
| 576 | CONHSO₂CH₃ | CH₃ | isobutyl | isobutyl | 2-F | O | NH |
| 577 | CONHSO₂CH₃ | CH₃ | isobutyl | isobutyl | 4-F | O | NH |
| 578 | CONHSO₂CH₃ | CH₃ | isobutyl | isobutyl | 2,4-2F | O | NH |
| 579 | CONHSO₂CH₃ | CH₃ | isobutyl | isobutyl | 2-F-4-CH₃ | O | NH |
| 580 | CONHSO₂CF₃ | CH₃ | isobutyl | isobutyl | 2-CH₃ | O | NH |
| 581 | CONHSO₂CF₃ | CH₃ | isobutyl | isobutyl | 4-CH₃ | O | NH |
| 582 | CONHSO₂CF₃ | CH₃ | isobutyl | isobutyl | 2,4-2CH₃ | O | NH |
| 583 | CONHSO₂CF₃ | CH₃ | isobutyl | isobutyl | 2-F | O | NH |
| 584 | CONHSO₂CF₃ | CH₃ | isobutyl | isobutyl | 4-F | O | NH |
| 585 | CONHSO₂CF₃ | CH₃ | isobutyl | isobutyl | 2,4-2F | O | NH |
| 586 | CONHSO₂CF₃ | CH₃ | isobutyl | isobutyl | 2-F-4-CH₃ | O | NH |
| 587 | 5-tetrazolyl | CH₃ | isobutyl | isobutyl | 2-CH₃ | O | NH |
| 588 | 5-tetrazolyl | CH₃ | isobutyl | isobutyl | 4-CH₃ | O | NH |
| 589 | 5-tetrazolyl | CH₃ | isobutyl | isobutyl | 2,4-2CH₃ | O | NH |
| 590 | 5-tetrazolyl | CH₃ | isobutyl | isobutyl | 2-F | O | NH |
| 591 | 5-tetrazolyl | CH₃ | isobutyl | isobutyl | 4-F | O | NH |
| 592 | 5-tetrazolyl | CH₃ | isobutyl | isobutyl | 2,4-2F | O | NH |
| 593 | 5-tetrazolyl | CH₃ | isobutyl | isobutyl | 2-F-4-CH₃ | O | NH |
| 594 | 5-tetrazolyl | CH₃ | isobutyl | isobutyl | 2-CH₃ | O | NH |
| 595 | 5-tetrazolyl | CH₃ | isobutyl | isobutyl | 4-CH₃ | O | NH |
| 596 | 5-tetrazolyl | CH₃ | isobutyl | isobutyl | 2,4-2CH₃ | O | NH |
| 597 | 5-tetrazolyl | CH₃ | isobutyl | isobutyl | 2-F | O | NH |
| 598 | 5-tetrazolyl | CH₃ | isobutyl | isobutyl | 4-F | O | NH |
| 599 | 5-tetrazolyl | CH₃ | isobutyl | isobutyl | 2,4-2F | O | NH |
| 600 | 5-tetrazolyl | CH₃ | isobutyl | isobutyl | 2-F-4-CH₃ | O | NH |
| 601 | COOCH₂CH₃ | CH₃ | cyclohexyl | isobutyl | 2-CH₃ | O | NH |
| 602 | COOCH₂CH₃ | CH₃ | cyclohexyl | isobutyl | 4-CH₃ | O | NH |
| 603 | COOCH₂CH₃ | CH₃ | cyclohexyl | isobutyl | 2,4-2CH₃ | O | NH |
| 604 | COOCH₂CH₃ | CH₃ | cyclohexyl | isobutyl | 2-F | O | NH |
| 605 | COOCH₂CH₃ | CH₃ | cyclohexyl | isobutyl | 4-F | O | NH |
| 606 | COOCH₂CH₃ | CH₃ | cyclohexyl | isobutyl | 2,4-2F | O | NH |
| 607 | COOCH₂CH₃ | CH₃ | cyclohexyl | isobutyl | 2-F-4-CH₃ | O | NH |
| 608 | COOH | CH₃ | cyclohexyl | isobutyl | 2-CH₃ | O | NH |
| 609 | COOH | CH₃ | cyclohexyl | isobutyl | 4-CH₃ | O | NH |
| 610 | COOH | CH₃ | cyclohexyl | isobutyl | 2,4-2CH₃ | O | NH |
| 611 | COOH | CH₃ | cyclohexyl | isobutyl | 2-F | O | NH |
| 612 | COOH | CH₃ | cyclohexyl | isobutyl | 4-F | O | NH |
| 613 | COOH | CH₃ | cyclohexyl | isobutyl | 2,4-2F | O | NH |
| 614 | COOH | CH₃ | cyclohexyl | isobutyl | 2-F-4-CH₃ | O | NH |
| 615 | CONHSO₂CH₃ | CH₃ | cyclohexyl | isobutyl | 2-CH₃ | O | NH |
| 616 | CONHSO₂CH₃ | CH₃ | cyclohexyl | isobutyl | 4-CH₃ | O | NH |
| 617 | CONHSO₂CH₃ | CH₃ | cyclohexyl | isobutyl | 2,4-2CH₃ | O | NH |
| 618 | CONHSO₂CH₃ | CH₃ | cyclohexyl | isobutyl | 2-F | O | NH |
| 619 | CONHSO₂CH₃ | CH₃ | cyclohexyl | isobutyl | 4-F | O | NH |
| 620 | CONHSO₂CH₃ | CH₃ | cyclohexyl | isobutyl | 2,4-2F | O | NH |
| 621 | CONHSO₂CH₃ | CH₃ | cyclohexyl | isobutyl | 2-F-4-CH₃ | O | NH |
| 622 | CONHSO₂CF₃ | CH₃ | cyclohexyl | isobutyl | 2-CH₃ | O | NH |
| 623 | CONHSO₂CF₃ | CH₃ | cyclohexyl | isobutyl | 4-CH₃ | O | NH |

TABLE 6-continued

| Compound Number | R² | R¹ | R⁷ | R⁸ | R | Y | X |
|---|---|---|---|---|---|---|---|
| 624 | CONHSO₂CF₃ | CH₃ | cyclohexyl | isobutyl | 2,4-2CH₃ | O | NH |
| 625 | CONHSO₂CF₃ | CH₃ | cyclohexyl | isobutyl | 2-F | O | NH |
| 626 | CONHSO₂CF₃ | CH₃ | cyclohexyl | isobutyl | 4-F | O | NH |
| 627 | CONHSO₂CF₃ | CH₃ | cyclohexyl | isobutyl | 2,4-2F | O | NH |
| 628 | CONHSO₂CF₃ | CH₃ | cyclohexyl | isobutyl | 2-F-4-CH₃ | O | NH |
| 629 | 5-tetrazolyl | CH₃ | cyclohexyl | isobutyl | 2-CH₃ | O | NH |
| 630 | 5-tetrazolyl | CH₃ | cyclohexyl | isobutyl | 4-CH₃ | O | NH |
| 631 | 5-tetrazolyl | CH₃ | cyclohexyl | isobutyl | 2,4-2CH₃ | O | NH |
| 632 | 5-tetrazolyl | CH₃ | cyclohexyl | isobutyl | 2-F | O | NH |
| 633 | 5-tetrazolyl | CH₃ | cyclohexyl | isobutyl | 4-F | O | NH |
| 634 | 5-tetrazolyl | CH₃ | cyclohexyl | isobutyl | 2,4-2F | O | NH |
| 635 | 5-tetrazolyl | CH₃ | cyclohexyl | isobutyl | 2-F-4-CH₃ | O | NH |
| 636 | 5-tetrazolyl | CH₃ | cyclohexyl | isobutyl | 2-CH₃ | O | NH |
| 637 | 5-tetrazolyl | CH₃ | cyclohexyl | isobutyl | 4-CH₃ | O | NH |
| 638 | 5-tetrazolyl | CH₃ | cyclohexyl | isobutyl | 2,4-2CH₃ | O | NH |
| 639 | 5-tetrazolyl | CH₃ | cyclohexyl | isobutyl | 2-F | O | NH |
| 640 | 5-tetrazolyl | CH₃ | cyclohexyl | isobutyl | 4-F | O | NH |
| 641 | 5-tetrazolyl | CH₃ | cyclohexyl | isobutyl | 2,4-2F | O | NH |
| 642 | 5-tetrazolyl | CH₃ | cyclohexyl | isobutyl | 2-F-4-CH₃ | O | NH |
| 643 | COOCH₂CH₃ | CF₃ | n-butyl | n-butyl | 2-CH₃ | O | NH |
| 644 | COOCH₂CH₃ | CF₃ | n-butyl | n-butyl | 4-CH₃ | O | NH |
| 645 | COOCH₂CH₃ | CF₃ | n-butyl | n-butyl | 2,4-2CH₃ | O | NH |
| 646 | COOCH₂CH₃ | CF₃ | n-butyl | n-butyl | 2-F | O | NH |
| 647 | COOCH₂CH₃ | CF₃ | n-butyl | n-butyl | 4-F | O | NH |
| 648 | COOCH₂CH₃ | CF₃ | n-butyl | n-butyl | 2,4-2F | O | NH |
| 649 | COOCH₂CH₃ | CF₃ | n-butyl | n-butyl | 2-F-4-CH₃ | O | NH |
| 650 | COOH | CF₃ | n-butyl | n-butyl | 2-CH₃ | O | NH |
| 651 | COOH | CF₃ | n-butyl | n-butyl | 4-CH₃ | O | NH |
| 652 | COOH | CF₃ | n-butyl | n-butyl | 2,4-2CH₃ | O | NH |
| 653 | COOH | CF₃ | n-butyl | n-butyl | 2-F | O | NH |
| 654 | COOH | CF₃ | n-butyl | n-butyl | 4-F | O | NH |
| 655 | COOH | CF₃ | n-butyl | n-butyl | 2,4-2F | O | NH |
| 656 | COOH | CF₃ | n-butyl | n-butyl | 2-F-4-CH₃ | O | NH |
| 657 | CONHSO₂CH₃ | CF₃ | n-butyl | n-butyl | 2-CH₃ | O | NH |
| 658 | CONHSO₂CH₃ | CF₃ | n-butyl | n-butyl | 4-CH₃ | O | NH |
| 659 | CONHSO₂CH₃ | CF₃ | n-butyl | n-butyl | 2,4-2CH₃ | O | NH |
| 660 | CONHSO₂CH₃ | CF₃ | n-butyl | n-butyl | 2-F | O | NH |
| 661 | CONHSO₂CH₃ | CF₃ | n-butyl | n-butyl | 4-F | O | NH |
| 662 | CONHSO₂CH₃ | CF₃ | n-butyl | n-butyl | 2,4-2F | O | NH |
| 663 | CONHSO₂CH₃ | CF₃ | n-butyl | n-butyl | 2-F-4-CH₃ | O | NH |
| 664 | CONHSO₂CF₃ | CF₃ | n-butyl | n-butyl | 2-CH₃ | O | NH |
| 665 | CONHSO₂CF₃ | CF₃ | n-butyl | n-butyl | 4-CH₃ | O | NH |
| 666 | CONHSO₂CF₃ | CF₃ | n-butyl | n-butyl | 2,4-2CH₃ | O | NH |
| 667 | CONHSO₂CF₃ | CF₃ | n-butyl | n-butyl | 2-F | O | NH |
| 668 | CONHSO₂CF₃ | CF₃ | n-butyl | n-butyl | 4-F | O | NH |
| 669 | CONHSO₂CF₃ | CF₃ | n-butyl | n-butyl | 2,4-2F | O | NH |
| 670 | CONHSO₂CF₃ | CF₃ | n-butyl | n-butyl | 2-F-4-CH₃ | O | NH |
| 671 | 5-tetrazolyl | CF₃ | n-butyl | n-butyl | 2-CH₃ | O | NH |
| 672 | 5-tetrazolyl | CF₃ | n-butyl | n-butyl | 4-CH₃ | O | NH |
| 673 | 5-tetrazolyl | CF₃ | n-butyl | n-butyl | 2,4-2CH₃ | O | NH |
| 674 | 5-tetrazolyl | CF₃ | n-butyl | n-butyl | 2-F | O | NH |
| 675 | 5-tetrazolyl | CF₃ | n-butyl | n-butyl | 4-F | O | NH |
| 676 | 5-tetrazolyl | CF₃ | n-butyl | n-butyl | 2,4-2F | O | NH |
| 677 | 5-tetrazolyl | CF₃ | n-butyl | n-butyl | 2-F-4-CH₃ | O | NH |
| 678 | 5-tetrazolyl | CF₃ | n-butyl | n-butyl | 2-CH₃ | O | NH |
| 679 | 5-tetrazolyl | CF₃ | n-butyl | n-butyl | 4-CH₃ | O | NH |
| 680 | 5-tetrazolyl | CF₃ | n-butyl | n-butyl | 2,4-2CH₃ | O | NH |
| 681 | 5-tetrazolyl | CF₃ | n-butyl | n-butyl | 2-F | O | NH |
| 682 | 5-tetrazolyl | CF₃ | n-butyl | n-butyl | 4-F | O | NH |
| 683 | 5-tetrazolyl | CF₃ | n-butyl | n-butyl | 2,4-2F | O | NH |
| 684 | 5-tetrazolyl | CF₃ | n-butyl | n-butyl | 2-F-4-CH₃ | O | NH |
| 685 | COOCH₂CH₃ | CF₃ | isobutyl | isobutyl | 2-CH₃ | O | NH |
| 686 | COOCH₂CH₃ | CF₃ | isobutyl | isobutyl | 4-CH₃ | O | NH |
| 687 | COOCH₂CH₃ | CF₃ | isobutyl | isobutyl | 2,4-2CH₃ | O | NH |
| 688 | COOCH₂CH₃ | CF₃ | isobutyl | isobutyl | 2-F | O | NH |
| 689 | COOCH₂CH₃ | CF₃ | isobutyl | isobutyl | 4-F | O | NH |
| 690 | COOCH₂CH₃ | CF₃ | isobutyl | isobutyl | 2,4-2F | O | NH |
| 691 | COOCH₂CH₃ | CF₃ | isobutyl | isobutyl | 2-F-4-CH₃ | O | NH |
| 692 | COOH | CF₃ | isobutyl | isobutyl | 2-CH₃ | O | NH |
| 693 | COOH | CF₃ | isobutyl | isobutyl | 4-CH₃ | O | NH |
| 694 | COOH | CF₃ | isobutyl | isobutyl | 2,4-2CH₃ | O | NH |
| 695 | COOH | CF₃ | isobutyl | isobutyl | 2-F | O | NH |
| 696 | COOH | CF₃ | isobutyl | isobutyl | 4-F | O | NH |
| 697 | COOH | CF₃ | isobutyl | isobutyl | 2,4-2F | O | NH |
| 698 | COOH | CF₃ | isobutyl | isobutyl | 2-F-4-CH₃ | O | NH |
| 699 | CONHSO₂CH₃ | CF₃ | isobutyl | isobutyl | 2-CH₃ | O | NH |
| 700 | CONHSO₂CH₃ | CF₃ | isobutyl | isobutyl | 4-CH₃ | O | NH |
| 701 | CONHSO₂CH₃ | CF₃ | isobutyl | isobutyl | 2,4-2CH₃ | O | NH |

TABLE 6-continued

| Compound Number | R² | R¹ | R⁷ | R⁸ | R | Y | X |
|---|---|---|---|---|---|---|---|
| 702 | CONHSO₂CH₃ | CF₃ | isobutyl | isobutyl | 2-F | O | NH |
| 703 | CONHSO₂CH₃ | CF₃ | isobutyl | isobutyl | 4-F | O | NH |
| 704 | CONHSO₂CH₃ | CF₃ | isobutyl | isobutyl | 2,4-2F | O | NH |
| 705 | CONHSO₂CH₃ | CF₃ | isobutyl | isobutyl | 2-F-4-CH₃ | O | NH |
| 706 | CONHSO₂CF₃ | CF₃ | isobutyl | isobutyl | 2-CH₃ | O | NH |
| 707 | CONHSO₂CF₃ | CF₃ | isobutyl | isobutyl | 4-CH₃ | O | NH |
| 708 | CONHSO₂CF₃ | CF₃ | isobutyl | isobutyl | 2,4-2CH₃ | O | NH |
| 709 | CONHSO₂CF₃ | CF₃ | isobutyl | isobutyl | 2-F | O | NH |
| 710 | CONHSO₂CF₃ | CF₃ | isobutyl | isobutyl | 4-F | O | NH |
| 711 | CONHSO₂CF₃ | CF₃ | isobutyl | isobutyl | 2,4-2F | O | NH |
| 712 | CONHSO₂CF₃ | CF₃ | isobutyl | isobutyl | 2-F-4-CH₃ | O | NH |
| 713 | 5-tetrazolyl | CF₃ | isobutyl | isobutyl | 2-CH₃ | O | NH |
| 714 | 5-tetrazolyl | CF₃ | isobutyl | isobutyl | 4-CH₃ | O | NH |
| 715 | 5-tetrazolyl | CF₃ | isobutyl | isobutyl | 2,4-2CH₃ | O | NH |
| 716 | 5-tetrazolyl | CF₃ | isobutyl | isobutyl | 2-F | O | NH |
| 717 | 5-tetrazolyl | CF₃ | isobutyl | isobutyl | 4-F | O | NH |
| 718 | 5-tetrazolyl | CF₃ | isobutyl | isobutyl | 2,4-2F | O | NH |
| 719 | 5-tetrazolyl | CF₃ | isobutyl | isobutyl | 2-F-4-CH₃ | O | NH |
| 720 | 5-tetrazolyl | CF₃ | isobutyl | isobutyl | 2-CH₃ | O | NH |
| 721 | 5-tetrazolyl | CF₃ | isobutyl | isobutyl | 4-CH₃ | O | NH |
| 722 | 5-tetrazolyl | CF₃ | isobutyl | isobutyl | 2,4-2CH₃ | O | NH |
| 723 | 5-tetrazolyl | CF₃ | isobutyl | isobutyl | 2-F | O | NH |
| 724 | 5-tetrazolyl | CF₃ | isobutyl | isobutyl | 4-F | O | NH |
| 725 | 5-tetrazolyl | CF₃ | isobutyl | isobutyl | 2,4-2F | O | NH |
| 726 | 5-tetrazolyl | CF₃ | isobutyl | isobutyl | 2-F-4-CH₃ | O | NH |
| 727 | COOCH₂CH₃ | CF₃ | cyclohexyl | isobutyl | 2-CH₃ | O | NH |
| 728 | COOCH₂CH₃ | CF₃ | cyclohexyl | isobutyl | 4-CH₃ | O | NH |
| 729 | COOCH₂CH₃ | CF₃ | cyclohexyl | isobutyl | 2,4-2CH₃ | O | NH |
| 730 | COOCH₂CH₃ | CF₃ | cyclohexyl | isobutyl | 2-F | O | NH |
| 731 | COOCH₂CH₃ | CF₃ | cyclohexyl | isobutyl | 4-F | O | NH |
| 732 | COOCH₂CH₃ | CF₃ | cyclohexyl | isobutyl | 2,4-2F | O | NH |
| 733 | COOCH₂CH₃ | CF₃ | cyclohexyl | isobutyl | 2-F-4-CH₃ | O | NH |
| 734 | COOH | CF₃ | cyclohexyl | isobutyl | 2-CH₃ | O | NH |
| 735 | COOH | CF₃ | cyclohexyl | isobutyl | 4-CH₃ | O | NH |
| 736 | COOH | CF₃ | cyclohexyl | isobutyl | 2,4-2CH₃ | O | NH |
| 737 | COOH | CF₃ | cyclohexyl | isobutyl | 2-F | O | NH |
| 738 | COOH | CF₃ | cyclohexyl | isobutyl | 4-F | O | NH |
| 739 | COOH | CF₃ | cyclohexyl | isobutyl | 2,4-2F | O | NH |
| 740 | COOH | CF₃ | cyclohexyl | isobutyl | 2-F-4-CH₃ | O | NH |
| 741 | CONHSO₂CH₃ | CF₃ | cyclohexyl | isobutyl | 2-CH₃ | O | NH |
| 742 | CONHSO₂CH₃ | CF₃ | cyclohexyl | isobutyl | 4-CH₃ | O | NH |
| 743 | CONHSO₂CH₃ | CF₃ | cyclohexyl | isobutyl | 2,4-2CH₃ | O | NH |
| 744 | CONHSO₂CH₃ | CF₃ | cyclohexyl | isobutyl | 2-F | O | NH |
| 745 | CONHSO₂CH₃ | CF₃ | cyclohexyl | isobutyl | 4-F | O | NH |
| 746 | CONHSO₂CH₃ | CF₃ | cyclohexyl | isobutyl | 2,4-2F | O | NH |
| 747 | CONHSO₂CH₃ | CF₃ | cyclohexyl | isobutyl | 2-F-4-CH₃ | O | NH |
| 748 | CONHSO₂CF₃ | CF₃ | cyclohexyl | isobutyl | 2-CH₃ | O | NH |
| 749 | CONHSO₂CF₃ | CF₃ | cyclohexyl | isobutyl | 4-CH₃ | O | NH |
| 750 | CONHSO₂CF₃ | CF₃ | cyclohexyl | isobutyl | 2,4-2CH₃ | O | NH |
| 751 | CONHSO₂CF₃ | CF₃ | cyclohexyl | isobutyl | 2-F | O | NH |
| 752 | CONHSO₂CF₃ | CF₃ | cyclohexyl | isobutyl | 4-F | O | NH |
| 753 | CONHSO₂CF₃ | CF₃ | cyclohexyl | isobutyl | 2,4-2F | O | NH |
| 754 | CONHSO₂CF₃ | CF₃ | cyclohexyl | isobutyl | 2-F-4-CH₃ | O | NH |
| 755 | 5-tetrazolyl | CF₃ | cyclohexyl | isobutyl | 2-CH₃ | O | NH |
| 756 | 5-tetrazolyl | CF₃ | cyclohexyl | isobutyl | 4-CH₃ | O | NH |
| 757 | 5-tetrazolyl | CF₃ | cyclohexyl | isobutyl | 2,4-2CH₃ | O | NH |
| 758 | 5-tetrazolyl | CF₃ | cyclohexyl | isobutyl | 2-F | O | NH |
| 759 | 5-tetrazolyl | CF₃ | cyclohexyl | isobutyl | 4-F | O | NH |
| 760 | 5-tetrazolyl | CF₃ | cyclohexyl | isobutyl | 2,4-2F | O | NH |
| 761 | 5-tetrazolyl | CF₃ | cyclohexyl | isobutyl | 2-F-4-CH₃ | O | NH |
| 762 | 5-tetrazolyl | CF₃ | cyclohexyl | isobutyl | 2-CH₃ | O | NH |
| 763 | 5-tetrazolyl | CF₃ | cyclohexyl | isobutyl | 4-CH₃ | O | NH |
| 764 | 5-tetrazolyl | CF₃ | cyclohexyl | isobutyl | 2,4-2CH₃ | O | NH |
| 765 | 5-tetrazolyl | CF₃ | cyclohexyl | isobutyl | 2-F | O | NH |
| 766 | 5-tetrazolyl | CF₃ | cyclohexyl | isobutyl | 4-F | O | NH |
| 767 | 5-tetrazolyl | CF₃ | cyclohexyl | isobutyl | 2,4-2F | O | NH |
| 768 | 5-tetrazolyl | CF₃ | cyclohexyl | isobutyl | 2-F-4-CH₃ | O | NH |
| 769 | COOCH₂CH₃ | CH₃ | n-butyl | n-butyl | 2-CH₃ | O | CH₂ |
| 770 | COOCH₂CH₃ | CH₃ | n-butyl | n-butyl | 4-CH₃ | O | CH₂ |
| 771 | COOCH₂CH₃ | CH₃ | n-butyl | n-butyl | 2,4-2CH₃ | O | CH₂ |
| 772 | COOCH₂CH₃ | CH₃ | n-butyl | n-butyl | 2-F | O | CH₂ |
| 773 | COOCH₂CH₃ | CH₃ | n-butyl | n-butyl | 4-F | O | CH₂ |
| 774 | COOCH₂CH₃ | CH₃ | n-butyl | n-butyl | 2,4-2F | O | CH₂ |
| 775 | COOCH₂CH₃ | CH₃ | n-butyl | n-butyl | 2-F-4-CH₃ | O | CH₂ |
| 776 | COOH | CH₃ | n-butyl | n-butyl | 2-CH₃ | O | CH₂ |
| 777 | COOH | CH₃ | n-butyl | n-butyl | 4-CH₃ | O | CH₂ |
| 778 | COOH | CH₃ | n-butyl | n-butyl | 2,4-2CH₃ | O | CH₂ |
| 779 | COOH | CH₃ | n-butyl | n-butyl | 2-F | O | CH₂ |

TABLE 6-continued

| Compound Number | R² | R¹ | R⁷ | R⁸ | R | Y | X |
|---|---|---|---|---|---|---|---|
| 780 | COOH | CH₃ | n-butyl | n-butyl | 4-F | O | CH₂ |
| 781 | COOH | CH₃ | n-butyl | n-butyl | 2,4-2F | O | CH₂ |
| 782 | COOH | CH₃ | n-butyl | n-butyl | 2-F-4-CH₃ | O | CH₂ |
| 783 | CONHSO₂CH₃ | CH₃ | n-butyl | n-butyl | 2-CH₃ | O | CH₂ |
| 784 | CONHSO₂CH₃ | CH₃ | n-butyl | n-butyl | 4-CH₃ | O | CH₂ |
| 785 | CONHSO₂CH₃ | CH₃ | n-butyl | n-butyl | 2,4-2CH₃ | O | CH₂ |
| 786 | CONHSO₂CH₃ | CH₃ | n-butyl | n-butyl | 2-F | O | CH₂ |
| 787 | CONHSO₂CH₃ | CH₃ | n-butyl | n-butyl | 4-F | O | CH₂ |
| 788 | CONHSO₂CH₃ | CH₃ | n-butyl | n-butyl | 2,4-2F | O | CH₂ |
| 789 | CONHSO₂CH₃ | CH₃ | n-butyl | n-butyl | 2-F-4-CH₃ | O | CH₂ |
| 790 | CONHSO₂CF₃ | CH₃ | n-butyl | n-butyl | 2-CH₃ | O | CH₂ |
| 791 | CONHSO₂CF₃ | CH₃ | n-butyl | n-butyl | 4-CH₃ | O | CH₂ |
| 792 | CONHSO₂CF₃ | CH₃ | n-butyl | n-butyl | 2,4-2CH₃ | O | CH₂ |
| 793 | CONHSO₂CF₃ | CH₃ | n-butyl | n-butyl | 2-F | O | CH₂ |
| 794 | CONHSO₂CF₃ | CH₃ | n-butyl | n-butyl | 4-F | O | CH₂ |
| 795 | CONHSO₂CF₃ | CH₃ | n-butyl | n-butyl | 2,4-2F | O | CH₂ |
| 796 | CONHSO₂CF₃ | CH₃ | n-butyl | n-butyl | 2-F-4-CH₃ | O | CH₂ |
| 797 | 5-tetrazolyl | CH₃ | n-butyl | n-butyl | 2-CH₃ | O | CH₂ |
| 798 | 5-tetrazolyl | CH₃ | n-butyl | n-butyl | 4-CH₃ | O | CH₂ |
| 799 | 5-tetrazolyl | CH₃ | n-butyl | n-butyl | 2,4-2CH₃ | O | CH₂ |
| 800 | 5-tetrazolyl | CH₃ | n-butyl | n-butyl | 2-F | O | CH₂ |
| 801 | 5-tetrazolyl | CH₃ | n-butyl | n-butyl | 4-F | O | CH₂ |
| 802 | 5-tetrazolyl | CH₃ | n-butyl | n-butyl | 2,4-2F | O | CH₂ |
| 803 | 5-tetrazolyl | CH₃ | n-butyl | n-butyl | 2-F-4-CH₃ | O | CH₂ |
| 804 | 5-tetrazolyl | CH₃ | n-butyl | n-butyl | 2-CH₃ | O | CH₂ |
| 805 | 5-tetrazolyl | CH₃ | n-butyl | n-butyl | 4-CH₃ | O | CH₂ |
| 806 | 5-tetrazolyl | CH₃ | n-butyl | n-butyl | 2,4-2CH₃ | O | CH₂ |
| 807 | 5-tetrazolyl | CH₃ | n-butyl | n-butyl | 2-F | O | CH₂ |
| 808 | 5-tetrazolyl | CH₃ | n-butyl | n-butyl | 4-F | O | CH₂ |
| 809 | 5-tetrazolyl | CH₃ | n-butyl | n-butyl | 2,4-2F | O | CH₂ |
| 810 | 5-tetrazolyl | CH₃ | n-butyl | n-butyl | 2-F-4-CH₃ | O | CH₂ |
| 811 | COOCH₂CH₃ | CH₃ | isobutyl | isobutyl | 2-CH₃ | O | CH₂ |
| 812 | COOCH₂CH₃ | CH₃ | isobutyl | isobutyl | 4-CH₃ | O | CH₂ |
| 813 | COOCH₂CH₃ | CH₃ | isobutyl | isobutyl | 2,4-2CH₃ | O | CH₂ |
| 814 | COOCH₂CH₃ | CH₃ | isobutyl | isobutyl | 2-F | O | CH₂ |
| 815 | COOCH₂CH₃ | CH₃ | isobutyl | isobutyl | 4-F | O | CH₂ |
| 816 | COOCH₂CH₃ | CH₃ | isobutyl | isobutyl | 2,4-2F | O | CH₂ |
| 817 | COOCH₂CH₃ | CH₃ | isobutyl | isobutyl | 2-F-4-CH₃ | O | CH₂ |
| 818 | COOH | CH₃ | isobutyl | isobutyl | 2-CH₃ | O | CH₂ |
| 819 | COOH | CH₃ | isobutyl | isobutyl | 4-CH₃ | O | CH₂ |
| 820 | COOH | CH₃ | isobutyl | isobutyl | 2,4-2CH₃ | O | CH₂ |
| 821 | COOH | CH₃ | isobutyl | isobutyl | 2-F | O | CH₂ |
| 822 | COOH | CH₃ | isobutyl | isobutyl | 4-F | O | CH₂ |
| 823 | COOH | CH₃ | isobutyl | isobutyl | 2,4-2F | O | CH₂ |
| 824 | COOH | CH₃ | isobutyl | isobutyl | 2-F-4-CH₃ | O | CH₂ |
| 825 | CONHSO₂CH₃ | CH₃ | isobutyl | isobutyl | 2-CH₃ | O | CH₂ |
| 826 | CONHSO₂CH₃ | CH₃ | isobutyl | isobutyl | 4-CH₃ | O | CH₂ |
| 827 | CONHSO₂CH₃ | CH₃ | isobutyl | isobutyl | 2,4-2CH₃ | O | CH₂ |
| 828 | CONHSO₂CH₃ | CH₃ | isobutyl | isobutyl | 2-F | O | CH₂ |
| 829 | CONHSO₂CH₃ | CH₃ | isobutyl | isobutyl | 4-F | O | CH₂ |
| 830 | CONHSO₂CH₃ | CH₃ | isobutyl | isobutyl | 2,4-2F | O | CH₂ |
| 831 | CONHSO₂CH₃ | CH₃ | isobutyl | isobutyl | 2-F-4-CH₃ | O | CH₂ |
| 832 | CONHSO₂CF₃ | CH₃ | isobutyl | isobutyl | 2-CH₃ | O | CH₂ |
| 833 | CONHSO₂CF₃ | CH₃ | isobutyl | isobutyl | 4-CH₃ | O | CH₂ |
| 834 | CONHSO₂CF₃ | CH₃ | isobutyl | isobutyl | 2,4-2CH₃ | O | CH₂ |
| 835 | CONHSO₂CF₃ | CH₃ | isobutyl | isobutyl | 2-F | O | CH₂ |
| 836 | CONHSO₂CF₃ | CH₃ | isobutyl | isobutyl | 4-F | O | CH₂ |
| 837 | CONHSO₂CF₃ | CH₃ | isobutyl | isobutyl | 2,4-2F | O | CH₂ |
| 838 | CONHSO₂CF₃ | CH₃ | isobutyl | isobutyl | 2-F-4-CH₃ | O | CH₂ |
| 839 | 5-tetrazolyl | CH₃ | isobutyl | isobutyl | 2-CH₃ | O | CH₂ |
| 840 | 5-tetrazolyl | CH₃ | isobutyl | isobutyl | 4-CH₃ | O | CH₂ |
| 841 | 5-tetrazolyl | CH₃ | isobutyl | isobutyl | 2,4-2CH₃ | O | CH₂ |
| 842 | 5-tetrazolyl | CH₃ | isobutyl | isobutyl | 2-F | O | CH₂ |
| 843 | 5-tetrazolyl | CH₃ | isobutyl | isobutyl | 4-F | O | CH₂ |
| 844 | 5-tetrazolyl | CH₃ | isobutyl | isobutyl | 2,4-2F | O | CH₂ |
| 845 | 5-tetrazolyl | CH₃ | isobutyl | isobutyl | 2-F-4-CH₃ | O | CH₂ |
| 846 | 5-tetrazolyl | CH₃ | isobutyl | isobutyl | 2-CH₃ | O | CH₂ |
| 847 | 5-tetrazolyl | CH₃ | isobutyl | isobutyl | 4-CH₃ | O | CH₂ |
| 848 | 5-tetrazolyl | CH₃ | isobutyl | isobutyl | 2,4-2CH₃ | O | CH₂ |
| 849 | 5-tetrazolyl | CH₃ | isobutyl | isobutyl | 2-F | O | CH₂ |
| 850 | 5-tetrazolyl | CH₃ | isobutyl | isobutyl | 4-F | O | CH₂ |
| 851 | 5-tetrazolyl | CH₃ | isobutyl | isobutyl | 2,4-2F | O | CH₂ |
| 852 | 5-tetrazolyl | CH₃ | isobutyl | isobutyl | 2-F-4-CH₃ | O | CH₂ |
| 853 | COOCH₂CH₃ | CH₃ | cyclohexyl | isobutyl | 2-CH₃ | O | CH₂ |
| 854 | COOCH₂CH₃ | CH₃ | cyclohexyl | isobutyl | 4-CH₃ | O | CH₂ |
| 855 | COOCH₂CH₃ | CH₃ | cyclohexyl | isobutyl | 2,4-2CH₃ | O | CH₂ |
| 856 | COOCH₂CH₃ | CH₃ | cyclohexyl | isobutyl | 2-F | O | CH₂ |
| 857 | COOCH₂CH₃ | CH₃ | cyclohexyl | isobutyl | 4-F | O | CH₂ |

TABLE 6-continued

| Compound Number | R² | R¹ | R⁷ | R⁸ | R | Y | X |
|---|---|---|---|---|---|---|---|
| 858 | COOCH₂CH₃ | CH₃ | cyclohexyl | isobutyl | 2,4-2F | O | CH₂ |
| 859 | COOCH₂CH₃ | CH₃ | cyclohexyl | isobutyl | 2-F-4-CH₃ | O | CH₂ |
| 860 | COOH | CH₃ | cyclohexyl | isobutyl | 2-CH₃ | O | CH₂ |
| 861 | COOH | CH₃ | cyclohexyl | isobutyl | 4-CH₃ | O | CH₂ |
| 862 | COOH | CH₃ | cyclohexyl | isobutyl | 2,4-2CH₃ | O | CH₂ |
| 863 | COOH | CH₃ | cyclohexyl | isobutyl | 2-F | O | CH₂ |
| 864 | COOH | CH₃ | cyclohexyl | isobutyl | 4-F | O | CH₂ |
| 865 | COOH | CH₃ | cyclohexyl | isobutyl | 2,4-2F | O | CH₂ |
| 866 | COOH | CH₃ | cyclohexyl | isobutyl | 2-F-4-CH₃ | O | CH₂ |
| 867 | CONHSO₂CH₃ | CH₃ | cyclohexyl | isobutyl | 2-CH₃ | O | CH₂ |
| 868 | CONHSO₂CH₃ | CH₃ | cyclohexyl | isobutyl | 4-CH₃ | O | CH₂ |
| 869 | CONHSO₂CH₃ | CH₃ | cyclohexyl | isobutyl | 2,4-2CH₃ | O | CH₂ |
| 870 | CONHSO₂CH₃ | CH₃ | cyclohexyl | isobutyl | 2-F | O | CH₂ |
| 871 | CONHSO₂CH₃ | CH₃ | cyclohexyl | isobutyl | 4-F | O | CH₂ |
| 872 | CONHSO₂CH₃ | CH₃ | cyclohexyl | isobutyl | 2,4-2F | O | CH₂ |
| 873 | CONHSO₂CH₃ | CH₃ | cyclohexyl | isobutyl | 2-F-4-CH₃ | O | CH₂ |
| 874 | CONHSO₂CF₃ | CH₃ | cyclohexyl | isobutyl | 2-CH₃ | O | CH₂ |
| 875 | CONHSO₂CF₃ | CH₃ | cyclohexyl | isobutyl | 4-CH₃ | O | CH₂ |
| 876 | CONHSO₂CF₃ | CH₃ | cyclohexyl | isobutyl | 2,4-2CH₃ | O | CH₂ |
| 877 | CONHSO₂CF₃ | CH₃ | cyclohexyl | isobutyl | 2-F | O | CH₂ |
| 878 | CONHSO₂CF₃ | CH₃ | cyclohexyl | isobutyl | 4-F | O | CH₂ |
| 879 | CONHSO₂CF₃ | CH₃ | cyclohexyl | isobutyl | 2,4-2F | O | CH₂ |
| 880 | CONHSO₂CF₃ | CH₃ | cyclohexyl | isobutyl | 2-F-4-CH₃ | O | CH₂ |
| 881 | 5-tetrazolyl | CH₃ | cyclohexyl | isobutyl | 2-CH₃ | O | CH₂ |
| 882 | 5-tetrazolyl | CH₃ | cyclohexyl | isobutyl | 4-CH₃ | O | CH₂ |
| 883 | 5-tetrazolyl | CH₃ | cyclohexyl | isobutyl | 2,4-2CH₃ | O | CH₂ |
| 884 | 5-tetrazolyl | CH₃ | cyclohexyl | isobutyl | 2-F | O | CH₂ |
| 885 | 5-tetrazolyl | CH₃ | cyclohexyl | isobutyl | 4-F | O | CH₂ |
| 886 | 5-tetrazolyl | CH₃ | cyclohexyl | isobutyl | 2,4-2F | O | CH₂ |
| 887 | 5-tetrazolyl | CH₃ | cyclohexyl | isobutyl | 2-F-4-CH₃ | O | CH₂ |
| 888 | 5-tetrazolyl | CH₃ | cyclohexyl | isobutyl | 2-CH₃ | O | CH₂ |
| 889 | 5-tetrazolyl | CH₃ | cyclohexyl | isobutyl | 4-CH₃ | O | CH₂ |
| 890 | 5-tetrazolyl | CH₃ | cyclohexyl | isobutyl | 2,4-2CH₃ | O | CH₂ |
| 891 | 5-tetrazolyl | CH₃ | cyclohexyl | isobutyl | 2-F | O | CH₂ |
| 892 | 5-tetrazolyl | CH₃ | cyclohexyl | isobutyl | 4-F | O | CH₂ |
| 893 | 5-tetrazolyl | CH₃ | cyclohexyl | isobutyl | 2,4-2F | O | CH₂ |
| 894 | 5-tetrazolyl | CH₃ | cyclohexyl | isobutyl | 2-F-4-CH₃ | O | CH₂ |
| 895 | COOCH₂CH₃ | CF₃ | n-butyl | n-butyl | 2-CH₃ | O | CH₂ |
| 896 | COOCH₂CH₃ | CF₃ | n-butyl | n-butyl | 4-CH₃ | O | CH₂ |
| 897 | COOCH₂CH₃ | CF₃ | n-butyl | n-butyl | 2,4-2CH₃ | O | CH₂ |
| 898 | COOCH₂CH₃ | CF₃ | n-butyl | n-butyl | 2-F | O | CH₂ |
| 899 | COOCH₂CH₃ | CF₃ | n-butyl | n-butyl | 4-F | O | CH₂ |
| 900 | COOCH₂CH₃ | CF₃ | n-butyl | n-butyl | 2,4-2F | O | CH₂ |
| 901 | COOCH₂CH₃ | CF₃ | n-butyl | n-butyl | 2-F-4-CH₃ | O | CH₂ |
| 902 | COOH | CF₃ | n-butyl | n-butyl | 2-CH₃ | O | CH₂ |
| 903 | COOH | CF₃ | n-butyl | n-butyl | 4-CH₃ | O | CH₂ |
| 904 | COOH | CF₃ | n-butyl | n-butyl | 2,4-2CH₃ | O | CH₂ |
| 905 | COOH | CF₃ | n-butyl | n-butyl | 2-F | O | CH₂ |
| 906 | COOH | CF₃ | n-butyl | n-butyl | 4-F | O | CH₂ |
| 907 | COOH | CF₃ | n-butyl | n-butyl | 2,4-2F | O | CH₂ |
| 908 | COOH | CF₃ | n-butyl | n-butyl | 2-F-4-CH₃ | O | CH₂ |
| 909 | CONHSO₂CH₃ | CF₃ | n-butyl | n-butyl | 2-CH₃ | O | CH₂ |
| 910 | CONHSO₂CH₃ | CF₃ | n-butyl | n-butyl | 4-CH₃ | O | CH₂ |
| 911 | CONHSO₂CH₃ | CF₃ | n-butyl | n-butyl | 2,4-2CH₃ | O | CH₂ |
| 912 | CONHSO₂CH₃ | CF₃ | n-butyl | n-butyl | 2-F | O | CH₂ |
| 913 | CONHSO₂CH₃ | CF₃ | n-butyl | n-butyl | 4-F | O | CH₂ |
| 914 | CONHSO₂CH₃ | CF₃ | n-butyl | n-butyl | 2,4-2F | O | CH₂ |
| 915 | CONHSO₂CH₃ | CF₃ | n-butyl | n-butyl | 2-F-4-CH₃ | O | CH₂ |
| 916 | CONHSO₂CH₃ | CF₃ | n-butyl | n-butyl | 2-CH₃ | O | CH₂ |
| 917 | CONHSO₂CH₃ | CF₃ | n-butyl | n-butyl | 4-CH₃ | O | CH₂ |
| 918 | CONHSO₂CH₃ | CF₃ | n-butyl | n-butyl | 2,4-2CH3 | O | CH₂ |
| 919 | CONHSO₂CH₃ | CF₃ | n-butyl | n-butyl | 2-F | O | CH₂ |
| 920 | CONHSO₂CH₃ | CF₃ | n-butyl | n-butyl | 4-F | O | CH₂ |
| 921 | CONHSO₂CH₃ | CF₃ | n-butyl | n-butyl | 2,4-2F | O | CH₂ |
| 922 | CONHSO₂CH₃ | CF₃ | n-butyl | n-butyl | 2-F-4-CH₃ | O | CH₂ |
| 923 | 5-tetrazolyl | CF₃ | n-butyl | n-butyl | 2-CH₃ | O | CH₂ |
| 924 | 5-tetrazolyl | CF₃ | n-butyl | n-butyl | 4-CH₃ | O | CH₂ |
| 925 | 5-tetrazolyl | CF₃ | n-butyl | n-butyl | 2,4-2CH₃ | O | CH₂ |
| 926 | 5-tetrazolyl | CF₃ | n-butyl | n-butyl | 2-F | O | CH₂ |
| 927 | 5-tetrazolyl | CF₃ | n-butyl | n-butyl | 4-F | O | CH₂ |
| 928 | 5-tetrazolyl | CF₃ | n-butyl | n-butyl | 2,4-2F | O | CH₂ |
| 929 | 5-tetrazolyl | CF₃ | n-butyl | n-butyl | 2-F-4-CH₃ | O | CH₂ |
| 930 | 5-tetrazolyl | CF₃ | n-butyl | n-butyl | 2-CH₃ | O | CH₂ |
| 931 | 5-tetrazolyl | CF₃ | n-butyl | n-butyl | 4-CH₃ | O | CH₂ |
| 932 | 5-tetrazolyl | CF₃ | n-butyl | n-butyl | 2,4-2CH₃ | O | CH₂ |
| 933 | 5-tetrazolyl | CF₃ | n-butyl | n-butyl | 2-F | O | CH₂ |
| 934 | 5-tetrazolyl | CF₃ | n-butyl | n-butyl | 4-F | O | CH₂ |
| 935 | 5-tetrazolyl | CF₃ | n-butyl | n-butyl | 2,4-2F | O | CH₂ |

TABLE 6-continued

| Compound Number | R² | R¹ | R⁷ | R⁸ | R | Y | X |
|---|---|---|---|---|---|---|---|
| 936 | 5-tetrazolyl | CF₃ | n-butyl | n-butyl | 2-F-4-CH₃ | O | CH₂ |
| 937 | COOCH₂CH₃ | CF₃ | isobutyl | isobutyl | 2-CH₃ | O | CH₂ |
| 938 | COOCH₂CH₃ | CF₃ | isobutyl | isobutyl | 4-CH₃ | O | CH₂ |
| 939 | COOCH₂CH₃ | CF₃ | isobutyl | isobutyl | 2,4-2CH₃ | O | CH₂ |
| 940 | COOCH₂CH₃ | CF₃ | isobutyl | isobutyl | 2-F | O | CH₂ |
| 941 | COOCH₂CH₃ | CF₃ | isobutyl | isobutyl | 4-F | O | CH₂ |
| 942 | COOCH₂CH₃ | CF₃ | isobutyl | isobutyl | 2,4-2F | O | CH₂ |
| 943 | COOCH₂CH₃ | CF₃ | isobutyl | isobutyl | 2-F-4-CH₃ | O | CH₂ |
| 944 | COOH | CF₃ | isobutyl | isobutyl | 2-CH₃ | O | CH₂ |
| 945 | COOH | CF₃ | isobutyl | isobutyl | 4-CH₃ | O | CH₂ |
| 946 | COOH | CF₃ | isobutyl | isobutyl | 2,4-2CH₃ | O | CH₂ |
| 947 | COOH | CF₃ | isobutyl | isobutyl | 2-F | O | CH₂ |
| 948 | COOH | CF₃ | isobutyl | isobutyl | 4-F | O | CH₂ |
| 949 | COOH | CF₃ | isobutyl | isobutyl | 2,4-2F | O | CH₂ |
| 950 | COOH | CF₃ | isobutyl | isobutyl | 2-F-4-CH₃ | O | CH₂ |
| 951 | CONHSO₂CH₃ | CF₃ | isobutyl | isobutyl | 2-CH₃ | O | CH₂ |
| 952 | CONHSO₂CH₃ | CF₃ | isobutyl | isobutyl | 4-CH₃ | O | CH₂ |
| 953 | CONHSO₂CH₃ | CF₃ | isobutyl | isobutyl | 2,4-2CH₃ | O | CH₂ |
| 954 | CONHSO₂CH₃ | CF₃ | isobutyl | isobutyl | 2-F | O | CH₂ |
| 955 | CONHSO₂CH₃ | CF₃ | isobutyl | isobutyl | 4-F | O | CH₂ |
| 956 | CONHSO₂CH₃ | CF₃ | isobutyl | isobutyl | 2,4-2F | O | CH₂ |
| 957 | CONHSO₂CH₃ | CF₃ | isobutyl | isobutyl | 2-F-4-CH₃ | O | CH₂ |
| 958 | CONHSO₂CF₃ | CF₃ | isobutyl | isobutyl | 2-CH₃ | O | CH₂ |
| 959 | CONHSO₂CF₃ | CF₃ | isobutyl | isobutyl | 4-CH₃ | O | CH₂ |
| 960 | CONHSO₂CF₃ | CF₃ | isobutyl | isobutyl | 2,4-2CH₃ | O | CH₂ |
| 961 | CONHSO₂CF₃ | CF₃ | isobutyl | isobutyl | 2-F | O | CH₂ |
| 962 | CONHSO₂CF₃ | CF₃ | isobutyl | isobutyl | 4-F | O | CH₂ |
| 963 | CONHSO₂CF₃ | CF₃ | isobutyl | isobutyl | 2,4-2F | O | CH₂ |
| 964 | CONHSO₂CF₃ | CF₃ | isobutyl | isobutyl | 2-F-4-CH₃ | O | CH₂ |
| 965 | 5-tetrazolyl | CF₃ | isobutyl | isobutyl | 2-CH₃ | O | CH₂ |
| 966 | 5-tetrazolyl | CF₃ | isobutyl | isobutyl | 4-CH₃ | O | CH₂ |
| 967 | 5-tetrazolyl | CF₃ | isobutyl | isobutyl | 2,4-2CH₃ | O | CH₂ |
| 968 | 5-tetrazolyl | CF₃ | isobutyl | isobutyl | 2-F | O | CH₂ |
| 969 | 5-tetrazolyl | CF₃ | isobutyl | isobutyl | 4-F | O | CH₂ |
| 970 | 5-tetrazolyl | CF₃ | isobutyl | isobutyl | 2,4-2F | O | CH₂ |
| 971 | 5-tetrazolyl | CF₃ | isobutyl | isobutyl | 2-F-4-CH₃ | O | CH₂ |
| 972 | 5-tetrazolyl | CF₃ | isobutyl | isobutyl | 2-CH₃ | O | CH₂ |
| 973 | 5-tetrazolyl | CF₃ | isobutyl | isobutyl | 4-CH₃ | O | CH₂ |
| 974 | 5-tetrazolyl | CF₃ | isobutyl | isobutyl | 2,4-2CH₃ | O | CH₂ |
| 975 | 5-tetrazolyl | CF₃ | isobutyl | isobutyl | 2-F | O | CH₂ |
| 976 | 5-tetrazolyl | CF₃ | isobutyl | isobutyl | 4-F | O | CH₂ |
| 977 | 5-tetrazolyl | CF₃ | isobutyl | isobutyl | 2,4-2F | O | CH₂ |
| 978 | 5-tetrazolyl | CF₃ | isobutyl | isobutyl | 2-F-4-CH₃ | O | CH₂ |
| 979 | COOCH₂CH₃ | CF₃ | cyclohexyl | isobutyl | 2-CH₃ | O | CH₂ |
| 980 | COOCH₂CH₃ | CF₃ | cyclohexyl | isobutyl | 4-CH₃ | O | CH₂ |
| 981 | COOCH₂CH₃ | CF₃ | cyclohexyl | isobutyl | 2,4-2CH₃ | O | CH₂ |
| 982 | COOCH₂CH₃ | CF₃ | cyclohexyl | isobutyl | 2-F | O | CH₂ |
| 983 | COOCH₂CH₃ | CF₃ | cyclohexyl | isobutyl | 4-F | O | CH₂ |
| 984 | COOCH₂CH₃ | CF₃ | cyclohexyl | isobutyl | 2,4-2F | O | CH₂ |
| 985 | COOCH₂CH₃ | CF₃ | cyclohexyl | isobutyl | 2-F-4-CH₃ | O | CH₂ |
| 986 | COOH | CF₃ | cyclohexyl | isobutyl | 2-CH₃ | O | CH₂ |
| 987 | COOH | CF₃ | cyclohexyl | isobutyl | 4-CH₃ | O | CH₂ |
| 988 | COOH | CF₃ | cyclohexyl | isobutyl | 2,4-2CH₃ | O | CH₂ |
| 989 | COOH | CF₃ | cyclohexyl | isobutyl | 2-F | O | CH₂ |
| 990 | COOH | CF₃ | cyclohexyl | isobutyl | 4-F | O | CH₂ |
| 991 | COOH | CF₃ | cyclohexyl | isobutyl | 2,4-2F | O | CH₂ |
| 992 | COOH | CF₃ | cyclohexyl | isobutyl | 2-F-4-CH₃ | O | CH₂ |
| 993 | CONHSO₂CH₃ | CF₃ | cyclohexyl | isobutyl | 2-CH₃ | O | CH₂ |
| 994 | CONHSO₂CH₃ | CF₃ | cyclohexyl | isobutyl | 4-CH₃ | O | CH₂ |
| 995 | CONHSO₂CH₃ | CF₃ | cyclohexyl | isobutyl | 2,4-2CH₃ | O | CH₂ |
| 996 | CONHSO₂CH₃ | CF₃ | cyclohexyl | isobutyl | 2-F | O | CH₂ |
| 997 | CONHSO₂CH₃ | CF₃ | cyclohexyl | isobutyl | 4-F | O | CH₂ |
| 998 | CONHSO₂CH₃ | CF₃ | cyclohexyl | isobutyl | 2,4-2F | O | CH₂ |
| 999 | CONHSO₂CH₃ | CF₃ | cyclohexyl | isobutyl | 2-F-4-CH₃ | O | CH₂ |
| 1000 | CONHSO₂CF₃ | CF₃ | cyclohexyl | isobutyl | 2-CH₃ | O | CH₂ |
| 1001 | CONHSO₂CF₃ | CF₃ | cyclohexyl | isobutyl | 4-CH₃ | O | CH₂ |
| 1002 | CONHSO₂CF₃ | CF₃ | cyclohexyl | isobutyl | 2,4-2CH₃ | O | CH₂ |
| 1003 | CONHSO₂CF₃ | CF₃ | cyclohexyl | isobutyl | 2-F | O | CH₂ |
| 1004 | CONHSO₂CF₃ | CF₃ | cyclohexyl | isobutyl | 4-F | O | CH₂ |
| 1005 | CONHSO₂CF₃ | CF₃ | cyclohexyl | isobutyl | 2,4-2F | O | CH₂ |
| 1006 | CONHSO₂CF₃ | CF₃ | cyclohexyl | isobutyl | 2-F-4-CH₃ | O | CH₂ |
| 1007 | 5-tetrazolyl | CF₃ | cyclohexyl | isobutyl | 2-CH₃ | O | CH₂ |
| 1008 | 5-tetrazolyl | CF₃ | cyclohexyl | isobutyl | 4-CH₃ | O | CH₂ |
| 1009 | 5-tetrazolyl | CF₃ | cyclohexyl | isobutyl | 2,4-2CH₃ | O | CH₂ |
| 1010 | 5-tetrazolyl | CF₃ | cyclohexyl | isobutyl | 2-F | O | CH₂ |
| 1011 | 5-tetrazolyl | CF₃ | cyclohexyl | isobutyl | 4-F | O | CH₂ |
| 1012 | 5-tetrazolyl | CF₃ | cyclohexyl | isobutyl | 2,4-2F | O | CH₂ |
| 1013 | 5-tetrazolyl | CF₃ | cyclohexyl | isobutyl | 2-F-4-CH₃ | O | CH₂ |

TABLE 6-continued

| Compound Number | $R^2$ | $R^1$ | $R^7$ | $R^8$ | R | Y | X |
|---|---|---|---|---|---|---|---|
| 1014 | 5-tetrazolyl | $CF_3$ | cyclohexyl | isobutyl | 2-$CH_3$ | O | $CH_2$ |
| 1015 | 5-tetrazolyl | $CF_3$ | cyclohexyl | isobutyl | 4-$CH_3$ | O | $CH_2$ |
| 1016 | 5-tetrazolyl | $CF_3$ | cyclohexyl | isobutyl | 2,4-2$CH_3$ | O | $CH_2$ |
| 1017 | 5-tetrazolyl | $CF_3$ | cyclohexyl | isobutyl | 2-F | O | $CH_2$ |
| 1018 | 5-tetrazolyl | $CF_3$ | cyclohexyl | isobutyl | 4-F | O | $CH_2$ |
| 1019 | 5-tetrazolyl | $CF_3$ | cyclohexyl | isobutyl | 2,4-2F | O | $CH_2$ |
| 1020 | 5-tetrazolyl | $CF_3$ | cyclohexyl | isobutyl | 2-F-4$CH_3$ | O | $CH_2$ |
| 1021 | $COOCH_2CH_3$ | $CH_3$ | n-butyl | n-butyl | 2-Cl | O | NH |
| 1022 | $COOCH_2CH_3$ | $CH_3$ | n-butyl | n-butyl | 3-Cl | O | NH |
| 1023 | $COOCH_2CH_3$ | $CH_3$ | n-butyl | n-butyl | 4-Cl | O | NH |
| 1024 | $COOCH_2CH_3$ | $CH_3$ | n-butyl | n-butyl | 3-$CF_3$4-Cl | O | NH |
| 1025 | $COOCH_2CH_3$ | $CH_3$ | n-butyl | n-butyl | H | S | NH |
| 1026 | $COOCH_2CH_3$ | $CH_3$ | n-butyl | n-butyl | 3-$CH_3$ | O | NH |
| 1027 | COOH | $CH_3$ | n-butyl | n-butyl | 2-Cl | O | NH |
| 1028 | COOH | $CH_3$ | n-butyl | n-butyl | 3-Cl | O | NH |
| 1029 | COOH | $CH_3$ | n-butyl | n-butyl | 4-Cl | O | NH |
| 1030 | COOH | $CH_3$ | n-butyl | n-butyl | 3-$CF_3$4-Cl | O | NH |
| 1031 | COOH | $CH_3$ | n-butyl | n-butyl | H | S | NH |
| 1032 | COOH | $CH_3$ | n-butyl | n-butyl | 3-$CH_3$ | O | NH |

The formula I compound of the invention can be prepared according to the following methods:

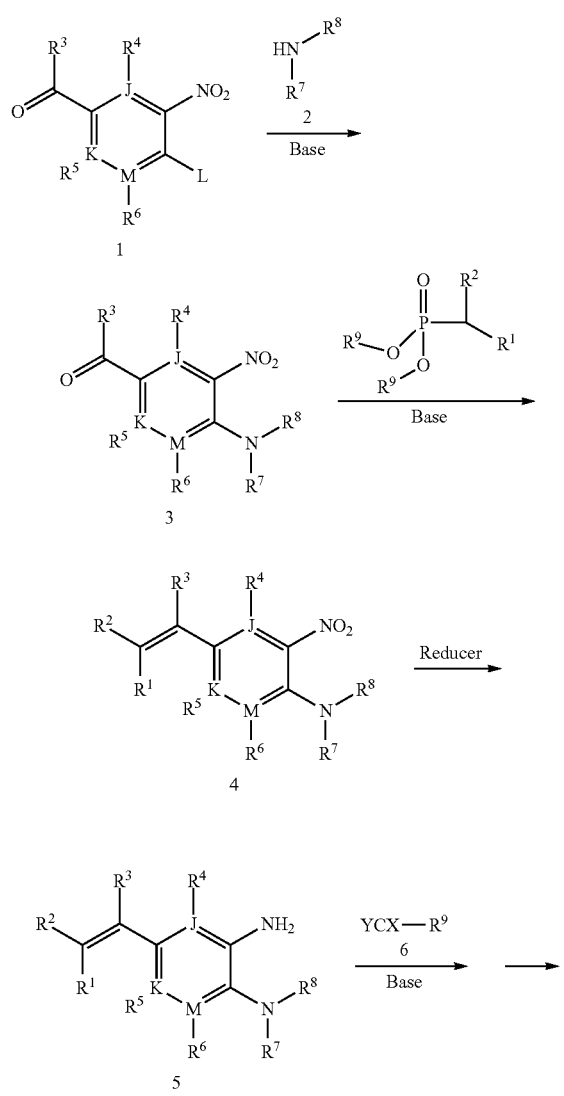

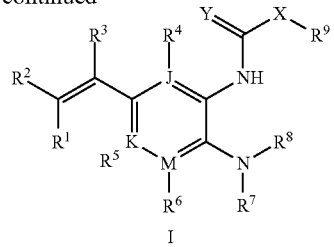

In the above reaction formula, the commercial halo nitroaromatic ketone compound 1 reacts with the substituted amino compound 2 to form the substituted amino nitroaromatic ketone compound 3 under the alkaline condition. Compound 3 reacts with wittingene reagent to form aromatic ethylene compound 4 under the alkaline condition. Compound 4 is reduced to amino compound 5 under the condition of reducing agent. Compound 5 reacts with compound 6 (isocyanate, isothiocyanate and chloroformate) to form formula I compound.

In the scheme:

L is selected from halogen, where L=F, Cl, Br and I; the definitions of the other groups are the same as before.

Base is selected from KOH, NaOH, $Na_2CO_3$, $K_2CO_3$, $NaHCO_3$, $Et_3N$, pyridine, MeONa, EtONa, NaH, potassium tert-butoxide or sodium tert-butoxide and so on.

The reaction is carried out in a suitable solvent, solvent is selected from THF, MeCN, PhMe, Xylene, Benzene, DMF, DMSO, acetone or methyl ethyl ketone and so on.

The reaction temperature may be between room temperature and the boiling point of the solvent, usually from 20 to 100° C.

The reaction time is from 30 minutes to 20 hours, usually from 1 to 10 hours.

The invention includes a formulation prepared by using the compound contained in the formula I as an active ingredient and other preparations. The preparation method of the formulation is as follows: dissolving the compound of the invention into a water-soluble organic solvent, a non-ionic surfactant, a water-soluble lipid, various cyclodextrins, a fatty acid, a fatty acid ester, a phospholipid or their combined solvents to prepare a preparation solution; adding normal saline to get 1-20% carbohydrates. The organic solvent includes one or a combination of polyethylene glycol (PEG), ethanol, propylene glycol and the like.

The compound shown in formula I of the present invention, its stereoisomer, cis-trans isomer, tautomer and pharmaceutically acceptable salt thereof, or a combination thereof, in the preparation of an inhibitor for inhibiting the activity of IDO-1 enzyme.

The compound shown in formula I of the present invention, its stereoisomer, cis-trans isomer, tautomer and pharmaceutically acceptable salt thereof, or a combination thereof, in the preparation of an anti-cancer drug, a viral infectious agent, a depressant, an organ transplant rejection agent or an autoimmune enhancer.

The cancer referred to is colon cancer, liver cancer, lymphoma, lung cancer, esophageal cancer, breast cancer, central nervous system tumor, melanoma, ovarian cancer, cervical cancer, renal cancer, leukemia, prostate cancer, pancreatic cancer or gastric cancer.

A pharmaceutical composition, any one or more compounds of formula I, its stereoisomer, cis-trans isomer, tautomer, pharmaceutically acceptable salts thereof and pharmaceutically acceptable carriers or diluents.

The compound of the present invention can be used as an active ingredient of an antitumor drug, and can be used alone or in combination with other antitumor drugs. The combination therapy referred to herein includes the use of at least one compound of the invention and a reactive derivative thereof in combination with one or more other anti-tumor agents to increase overall efficacy. The dose and time of administration in combination should be determined according to the most reasonable therapeutic effect obtained under different conditions.

The pharmaceutical agents contemplated include an effective dose of a compound of formula I. By "effective amount" herein is meant the amount of the compound required to produce a therapeutic effect for the subject being treated. The effective dose or dose can be varied by an experienced person depending on the recommendations of the situation. For example, the type of tumor treated is different, the usage of the drug is different; whether it is shared with other treatment methods such as other anti-tumor drugs, the dosage can be changed. Any application formulation form that can be made. If some of them have a basic or acidic compound and can form a non-toxic acid or salt, the form of the salt of the compound can be used. The carboxylic acid compound may form a usable salt with an alkali metal or an alkaline earth metal.

The compounds encompassed by the formula I in the invention are generally soluble in organic solvents, water-soluble solvents, organic solvents or a mixed solvent of a water-soluble solvent and water. The water-soluble solvent is preferably alcohol, polyethylene glycol, N-methyl-2-pyrrolidinone, DMA, DMF, DMSO, acetonitrile and their combination. The alcohol is preferably methanol, ethanol, isopropanol, glycerol or ethylene glycol. The compound of the present invention can be formulated into a preparation by mixing with usual formulation carriers. The compound is dissolved in a water-soluble organic solvent, an aprotic solvent, a water-soluble lipid, a cyclodextrin, a fatty acid, a phospholipid or a mixed solvent of these solvents to prepare a drug solution; and then adding physiological saline to obtain 1-20% carbohydrates, such as an aqueous solution of glucose. The formulations thus prepared are stable and are used in animals and clinical trials.

The product drug prepared by using the compound of the formula I as an active ingredient can be administered by oral or parenteral route, or can be administered by a drug pump in vivo and other methods. The non-intestinal route refers to subcutaneous intradermal, intramuscular, intravenous, intraarterial, intraatrial, synovial, sternal, intrathecal, traumatic site, intracranial injection or drip technology and so on. Professional person uses a conventional method to mix and mix and finally become the desired pharmaceutical dosage form. It may be a tablet, a capsule, an emulsion, a powder, a small needle for intravenous administration, a large infusion, a lyophilized powder, a dropping pill, a milk suspension, an aqueous suspension solution, an aqueous solution, a colloid, a colloidal solution, a sustained release preparation, a nano preparation or other forms of the dosage form are for animal or clinical use.

The compound of formula I of the invention is useful for the treatment or amelioration of cancer drugs for a certain tissue or organ. The cancers referred to include, but are not limited to, colon cancer, liver cancer, lymphoma, lung cancer, esophageal cancer, breast cancer, central nervous system tumor, melanoma, ovarian cancer, renal cancer, leukemia, prostate cancer or pancreatic cancer.

The invention has the advantages of having IDO-1 enzyme inhibitory activity and is expected to provide a novel therapeutic method and scheme for the related diseases caused by the IDO enzyme.

THE DETAILED DESCRIPTION OF THE INVENTION

The following examples are provided to assist in a comprehensive understanding of the claims and their equivalents, and are not intended to limit the present invention.

Example 1

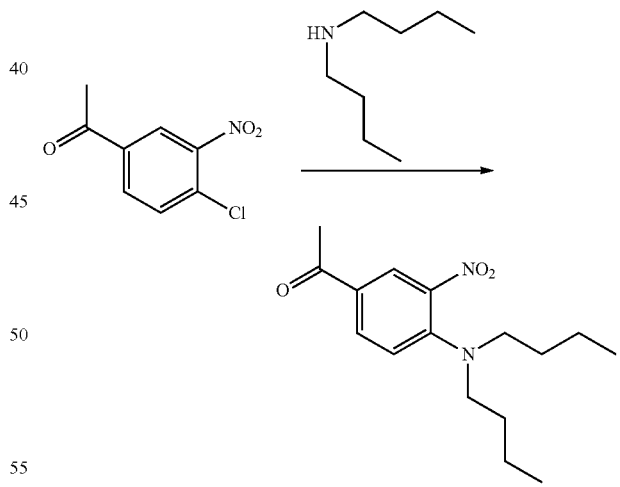

To a 250 mL flask, 10.0 g of 3'-nitro-4'-chlorocetophenone and 100 mL of di-n-butylamine were added, and the mixture was heated at 100° C. for 20 hours. After reaction was completed by TLC monitoring, the reaction mixture was evaporated to dryness, and the residue was dissolved in ethyl acetate (300 mL) and washed with water (100 mL×3), and the organic phase was dried over anhydrous sodium sulfate for 12 hr. The solvent was removed in vacuo. purification of residues by silica gel column chromatography (eluents are ethyl acetate and petroleum ether (boiling range 60-90° C.), the volume ratio is 1:6)) to obtain the compound 1-(4-(dibutylamino)-3-nitrophenyl)ethan-1-one, 11.3 g yellow solid.

$^1$H-NMR (300 MHz, CDCl$_3$) δ (ppm): 0.89 (t, J=7.5 Hz, 6H), 1.23-1.35 (m, 4H), 1.52-1.62 (m, 4H), 2.51 (s, 3H), 3.23 (t, J=7.2 Hz, 4H), 7.08 (dd, J=14.4, 3.9 Hz, 1H), 7.96 (dd, J=9.0, 2.1 Hz, 1H), 8.31 (dd, J=2.1 Hz, 1H).

Example 2

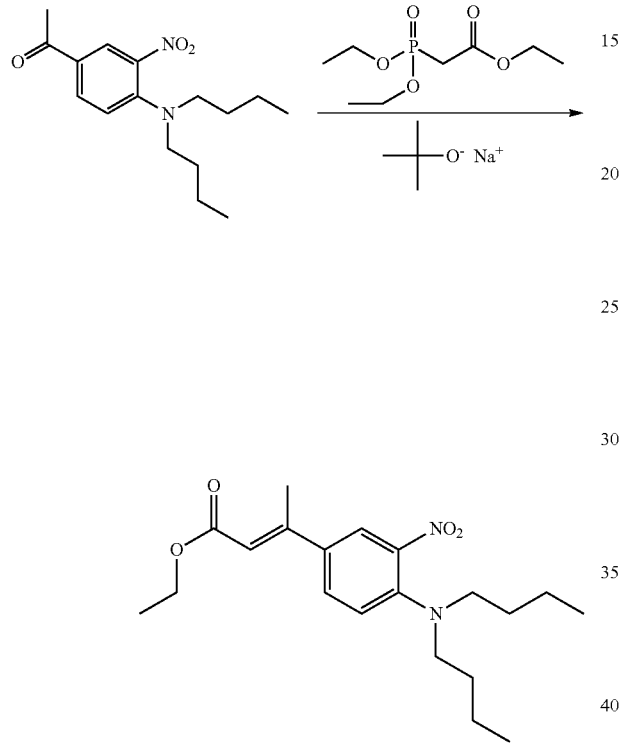

To a 250 mL flask, 9.9 g of sodium t-butoxide and 150 mL of tetrahydrofuran were added, and 23.0 g of ethyl 2-(diethoxyphosphoryl)acetate was added dropwise with stirring at a temperature of 0 to 5° C. After the dropwise addition completely, the mixture was stirred at room temperature for 0.5 hour, and the compound 1-(4-(dibutylamino)-3-nitrophenyl)ethan-1-one dissolved in 50 mL of tetrahydrofuran was added dropwise with stirring at a temperature of 20-30° C. After the dropwise addition completely, the mixture was stirred at room temperature for 12 hours. After reaction was completed by TLC monitoring, the reaction mixture was washed with a saturated aqueous solution of ammonium chloride (100 mL×3), and the organic phase was dried over anhydrous sodium sulfate for 12 hours, the solvent was removed in vacuo. Purification of residues by silica gel column chromatography (eluents are ethyl acetate and petroleum ether (boiling range 60-90° C.), volume ratio 1:10) to obtain the compound ethyl (E)-3-(4-(dibutylamino)-3-nitrophenyl)but-2-enoate, 6.3 g yellow solid.

$^1$H-NMR (300 MHz, CDCl$_3$) δ (ppm): 0.87 (t, J=7.5 Hz, 6H), 1.17-1.34 (m, 7H), 1.48-1.62 (m, 4H), 2.51 (s, 3H), 3.16 (t, J=7.2 Hz, 4H), 4.18 (q, J=7.2 Hz, 2H), 6.14 (d, J=1.2 Hz, 1H), 7.53-7.54 (m, 2H), 7.87 (d, J=2.1 Hz, 1H).

Example 3

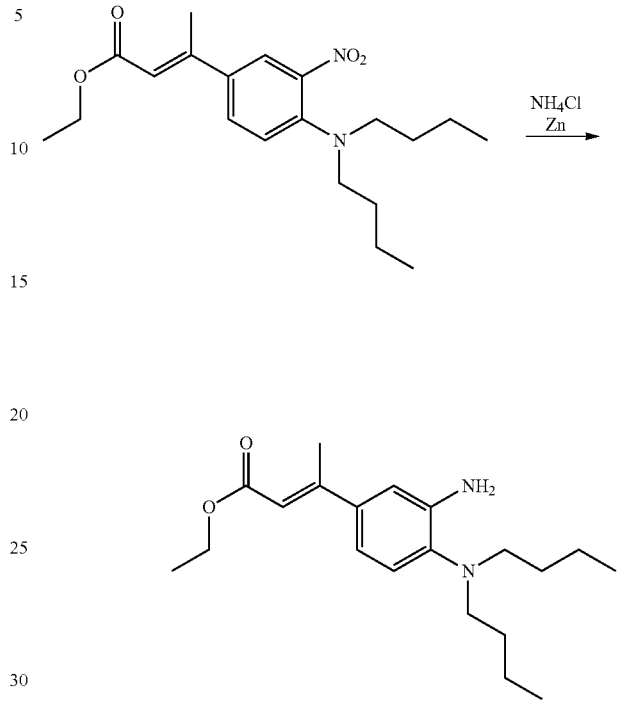

To a 250 mL flask, 2.7 g of compound ethyl (E)-3-(4-(dibutylamino)-3-nitrophenyl)but-2-enoate, 4.0 g of ammonium chloride, zinc powder 4.9 g, 100 mL of ethanol and 20 mL of water were added, the mixture was stirred at room temperature for 2 hours. After reaction was completed by TLC monitoring, the reaction mixture was filtered, and the solvent of filtrate was removed in vacuo. Purification of residues by silica gel column chromatography (eluent ethyl acetate and petroleum ether (boiling range: 60-90° C.), volume ratio: 1:10) to obtain the compound ethyl (E)-3-(3-amino-4-(dibutylamino)phenyl)but-2-enoate, 0.3 g reddish brown viscous liquid.

$^1$H-NMR (300 MHz, CDCl$_3$) δ (ppm): 0.87 (t, J=6.9 Hz, 6H), 1.10 (t, J=6.9 Hz, 3H), 1.23-1.30 (m, 4H), 1.33-1.43 (m, 4H), 2.16 (d, J=1.5 Hz, 3H), 2.86 (t, J=7.5 Mz, 4H), 4.03 (q, J=6.9 Hz, 2H), 6.08 (d, J=0.9 Hz, 1H), 6.56-6.60 (m, 2H), 6.96 (d, J=7.5 Hz, 1H).

Example 4

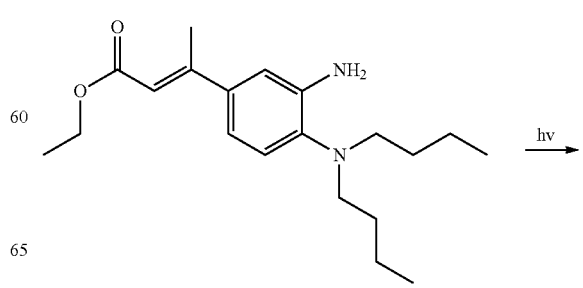

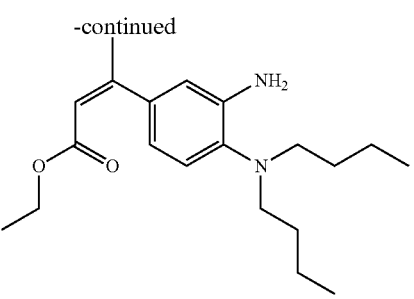

To a 100 mL flask, 0.3 g of compound ethyl (E)-3-(3-amino-4-(dibutylamino)phenyl)but-2-enoate and acetonitrile 50 mL were added, irradiated with UV light (wavelength: 365 nM) for 48 hours, the solvent was removed in vacuo. Purification of residues by silica gel column chromatography (eluents are ethyl acetate and petroleum ether (boiling range 60-90° C.), volume ratio 1:10) to obtain the compound ethyl (Z)-3-(3-amino-4-(dibutylamino)phenyl)but-2-enoate, 0.11 g reddish brown viscous liquid.

$^1$H-NMR (300 MHz, CDCl$_3$) δ (ppm): 0.87 (t, J=−6.9 Hz, 6H), 1.09 (t, J=6.9 Hz, 3H), 1.22-1.30 (m, 4H), 1.33-1.42 (m, 4H), 2.15 (d, J=1.5 Hz, 3H), 2.86 (t, J=7.5 Mz, 4H), 4.01 (q, J=6.9 Hz, 2H), 5.82 (d, J=0.9 Hz, 1H), 6.56-6.60 (m, 2H), 6.97 (d, J=7.5 Hz, 1H).

Example 5

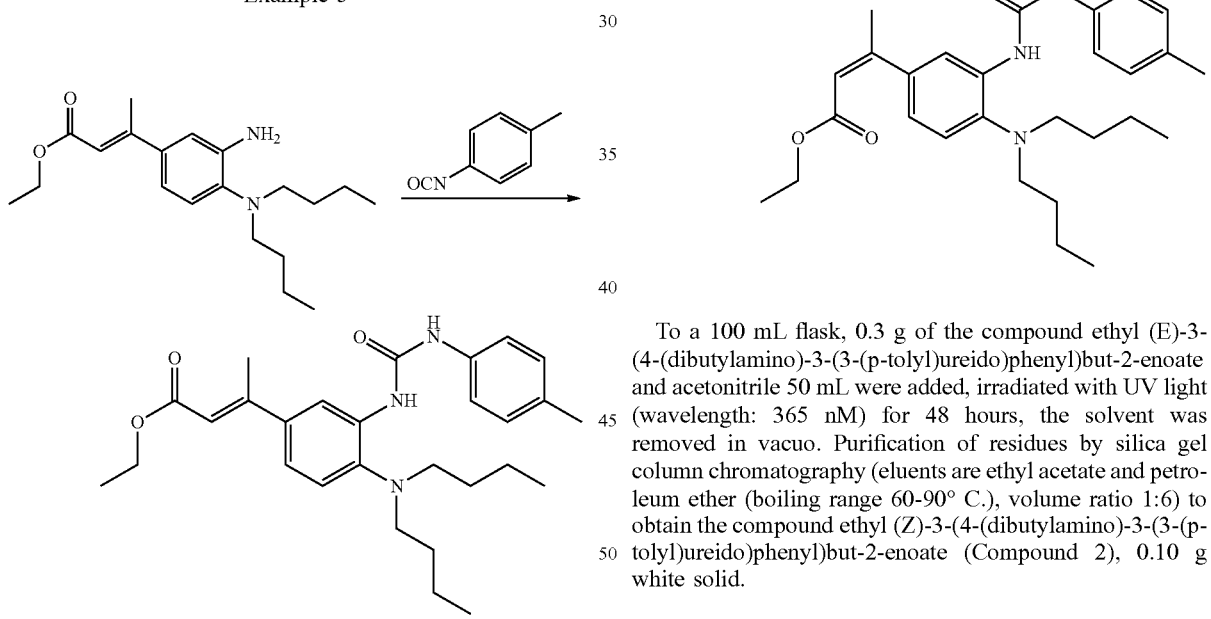

To a 100 mL flask, 0.4 g of the compound ethyl (E)-3-(3-amino-4-(dibutylamino)phenyl)but-2-enoate, 0.16 g of p-toluene isocyanate and 30 mL of tetrahydrofuran were added. The mixture was stirred at room temperature for 8 hours. After reaction was completed by TLC monitoring, the solvent was removed in vacuo. Purification of residues by silica gel column chromatography (eluents are ethyl acetate and petroleum ether (boiling range: 60-90° C.), volume ratio: 1:5) to obtain the compound ethyl (E)-3-(4-(dibutylamino)-3-(3-(p-tolyl)ureido)phenyl)but-2-enoate (Compound 518), 0.12 g white solid.

$^1$H-NMR (300 MHz, CDCl$_3$) δ (ppm): 0.81 (t, J=6.9 Hz, 6H), 1.12-1.16 (m, 81), 1.30 (t, J=6.9 Hz, 3H), 2.35 (s, 3H), 2.72 (t, J=6.9 Hz, 4H), 4.18 (q, J=6.9 Hz, 2H), 6.18 (s, 1H), 6.45 (s, 1H), 7.08-7.26 (m, 5H), 8.22 (s, 1H), 8.45 (s, 1H).

Example 6

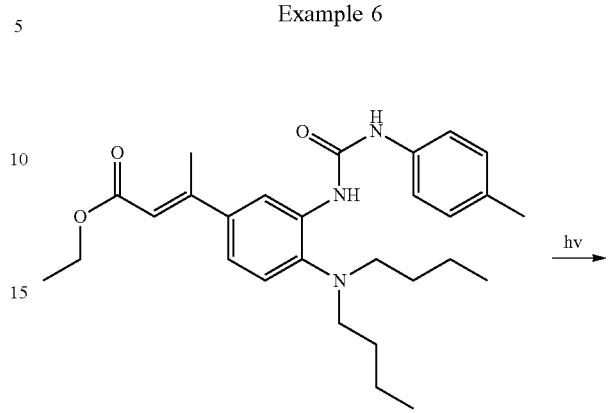

To a 100 mL flask, 0.3 g of the compound ethyl (E)-3-(4-(dibutylamino)-3-(3-(p-tolyl)ureido)phenyl)but-2-enoate and acetonitrile 50 mL were added, irradiated with UV light (wavelength: 365 nM) for 48 hours, the solvent was removed in vacuo. Purification of residues by silica gel column chromatography (eluents are ethyl acetate and petroleum ether (boiling range 60-90° C.), volume ratio 1:6) to obtain the compound ethyl (Z)-3-(4-(dibutylamino)-3-(3-(p-tolyl)ureido)phenyl)but-2-enoate (Compound 2), 0.10 g white solid.

Example 7

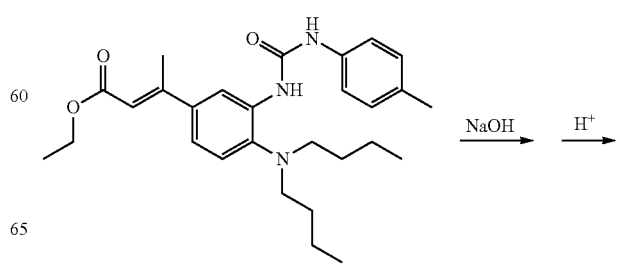

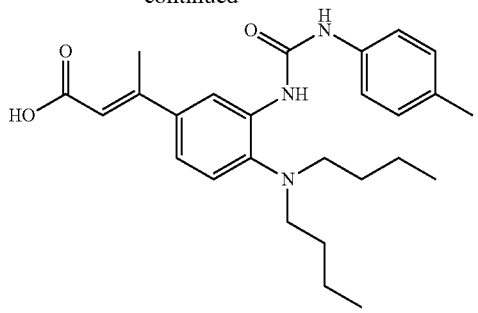

To a 100 mL flask, 100 g of compound ethyl (E)-3-(4-(dibutylamino)-3-(3-(p-tolyl)ureido) phenyl)but-2-enoate, ethanol 50 mL and 3.0 g of sodium hydroxide were added. The mixture was stirred at room temperature for 12 hours. After reaction was completed by TLC monitoring, the solvent was removed in vacuo, and the residue was dissolved in ethyl acetate (300 mL) and water (100 mL), and the mixture was adjusted to pH=3 with concentrated hydrochloric acid, and the organic phase was dried over anhydrous sodium sulfate for 12 hours, the solvent was removed in vacuo. Purification of residues by silica gel column chromatography (eluents are ethyl acetate and petroleum ether (boiling range 60-90° C.) in a volume ratio of 1:2) to obtain the compound (E)-3-(4-(dibutylamino)-3-(3-(p-tolyl)ureido) phenyl)but-2-enoic acid (Compound 525), 0.11 g white solid.

$^1$H-NMR (300 MHz, CDCl$_3$) δ (ppm): 0.81 (t. J=6.9 Hz, 6H), 1.13-1.17 (m, 8H), 2.35 (s, 31-H), 2.73 (t, J=6.9 Hz, 4H), 6.17 (s, 1H), 6.46 (s, 1H), 7.07-7.25 (m, 5H), 8.23 (s, 1H), 8.46 (s, 1H), 12.05 (s, 1H). MS (ESI), m/z (%): 438.32 [M+H]$^+$.

Example 8

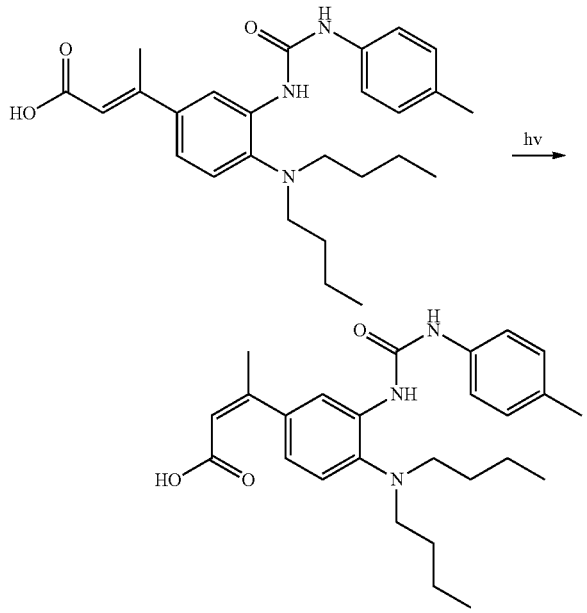

To a 100 mL flask, 0.3 g of compound (E)-3-(4-(dibutylamino)-3-(3-(p-tolyl)ureido)phenyl)but-2-enoic acid and 50 mL of acetonitrile were added, irradiated with UV light (wavelength: 365 nM) for 48 hours, the solvent was removed in vacuo. Purification of residues by silica gel column chromatography (eluents are ethyl acetate and petroleum ether (boiling range 60-90° C.), volume ratio 1:2) to obtain compound (Z)-3-(4-(dibutylamino)-3-(3-(p-tolyl)ureido)phenyl)but-2-enoic acid (Compound 9), 0.16 g white solid.

$^1$H-NMR (300 MHz, DMSO-d$_6$) δ (ppm): 0.85 (t, J=6.9 Hz, 6H), 1.19-1.31 (m, 8H), 2.26 (s, 3H), 2.50 (s, 3H), 2.83-2.88 (m, 4H), 5.81 (s, 1H), 7.03-7.12 (m, 3H), 7.33-7.37 (m, 2H), 8.04 (s, 1H), 8.82-8.36 (m, 1H), 8.36 (s, 1H), 9.35 (s, 1H). MS (ESI), m/z (%): 438.32 [M+H]$^+$.

Example 9

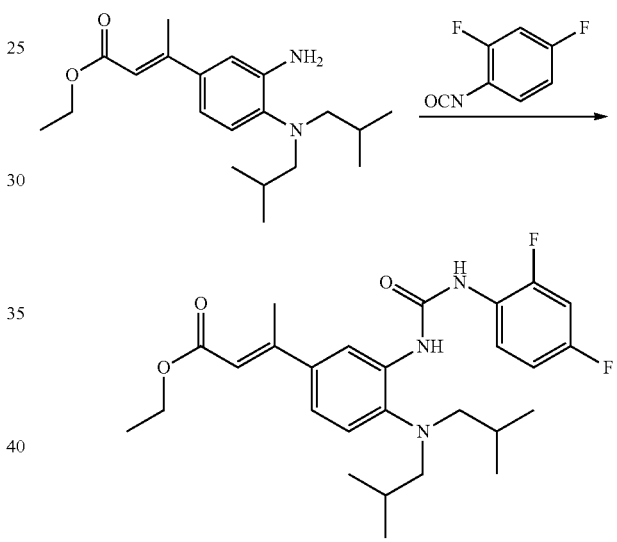

To a 100 mL flask, 0.5 g of the compound ethyl (E)-3-(3-amino-4-(diisobutylamino)phenyl)but-2-enoate (preparation method is the same as in Example 1, Example 2 and Example 3), 3 g of 2,4-difluorophenyl isocyanate and 30 mL of tetrahydrofuran were added. The mixture was stirred at room temperature for 4 hours. After reaction was completed by TLC monitoring, the solvent was removed in vacuo. Purification of residues by silica gel column chromatography (eluents are ethyl acetate and petroleum ether (boiling range: 60-90° C.), volume ratio: 1:5) to obtain the compound ethyl (E)-3-(3-(3-(2,4-difluorophenyl)ureido)-4-(diisobutylamino)phenyl) but-2-enoate (Compound 564), 0.16 g white solid.

$^1$H-NMR (600 MHz, DMSO-d$_6$) δ (ppm): 0.83 (d, J=6.0 Hz, 12H), 1.24 (t, J=6.0 Hz, 3H), 1.69-1.72 (m, 2H), 2.49 (s, 3H), 2.79 (d, J=12.0 Hz, 4H), 4.13 (q, J=6.0 Hz, 2H), 6.09 (s, 1H), 7.03-7.05 (m, 1H), 7.19-7.23 (m, 2H), 7.29-7.31 (t, J=6 Hz, 1H), 7.98-8.01 (m, 1H), 8.05 (d, J=6.0 Hz, 1H), 8.09 (s, 1H), 9.33 (s, 1H). MS (ESI), m/z (%): 488.32[M+H]$^+$.

Example 10

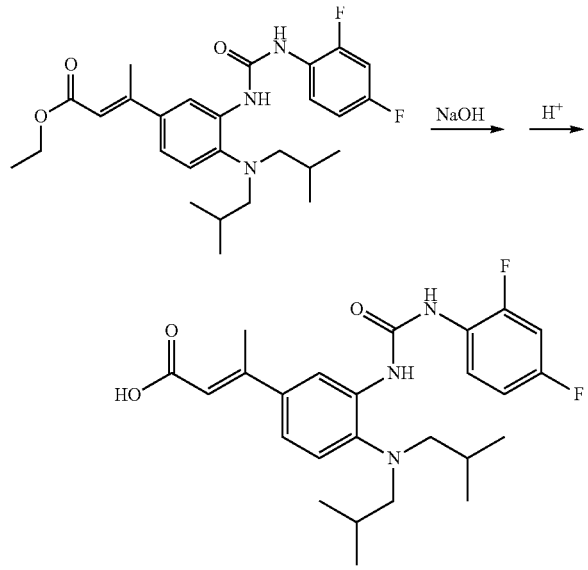

To a 100 mL flask, 0.3 g of the compound ethyl (E)-3-(3-(3-(2,4-difluorophenyl)ureido)-4-(diisobutylamino)phenyl) but-2-enoate, ethanol 50 mL and sodium hydroxide 3.0 g were added. The mixture was stirred at room temperature for 12 hours. After reaction was completed by TLC monitoring, the solvent was removed in vacuo, and the residue was dissolved in ethyl acetate (300 mL) and water (100 mL), and the mixture was adjusted to pH=3 with concentrated hydrochloric acid, and the organic phase was dried over anhydrous sodium sulfate for 12 hours, the solvent was removed in vacuo. Purification of residues by silica gel column chromatography (eluents are ethyl acetate and petroleum ether (boiling range 60-90° C.), volume ratio 1:2) to obtain the compound (E)-3-(3-(3-(2,4-difluorophenyl)ureido)-4-(diisobutylamino)phenyl)but-2-enoic acid (Compound 571), 0.15 g white solid.

$^1$H-NMR (600 MHz, DMSO-$d_6$) δ (ppm): 9.31 (s, 1H), 8.08 (s, 1H), 8.05 (d, J=6.0 Hz, 1H), 7.98-8.03 (m, 1H), 7.29-7.31 (t, J=6 Hz, 1H), 7.19-7.24 (m, 2H), 7.01-7.06 (m, 1H), 6.05 (s, 1H), 2.86-2.90 (m, 4H), 2.48 (s, 3H), 1.69-1.72 (m, 2H), 0.82 (d, J=6.0 Hz, 12H). MS (ESI), m/z (%): 460.27[M+H]$^+$.

Example 11

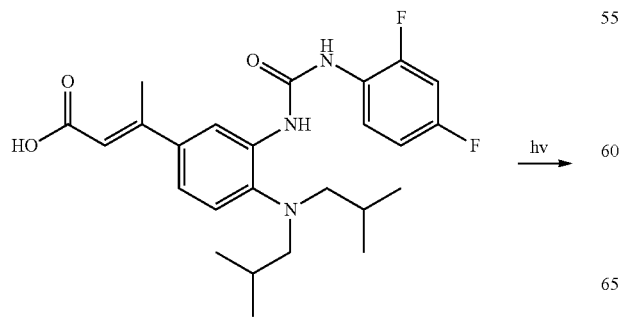

To a 100 mL flask, 0.1 g of compound (E)-3-(3-(3-(2,4-difluorophenyl)ureido)-4-(diisobutylamino)phenyl)but-2-enoic acid and 50 mL of acetonitrile, irradiated with UV light (wavelength: 365 nM) for 48 hours, the solvent was removed in vacuo. Purification of residues by silica gel column chromatography (eluents are ethyl acetate and petroleum ether (boiling range 60-90° C.), volume ratio 1:2) to obtain the compound (Z)-3-(3-(3-(2,4-difluorophenyl)ureido)-4-(diisobutylamino)phenyl)but-2-enoic acid (Compound 55), 0.03 g white solid.

$^1$H-NMR (600 MHz, DMSO-$d_6$) δ 11.88 (s, 1H), 9.28 (s, 1H), 8.05 (s, 1H), 7.94 (td, J=9.1, 6.5 Hz, 1H), 7.78 (d, J=1.7 Hz, 1H), 7.34-7.24 (m, 1H), 7.13 (d, J=8.3 Hz, 1H), 7.04 (t, J=8.0 Hz, 1H), 6.87 (dd, J=8.2, 1.6 Hz, 1H), 5.84 (s, 1H), 2.70 (d, J=6.8 Hz, 4H), 2.09 (s, 3H), 1.71-1.66 (m, 2H), 0.85 (d, J=6.0 Hz, 12H). MS (ESI), m/z (%): 460.28[M+H]$^+$.

Partial Compound Nuclear Magnetic Resonance Data:

Compound 13

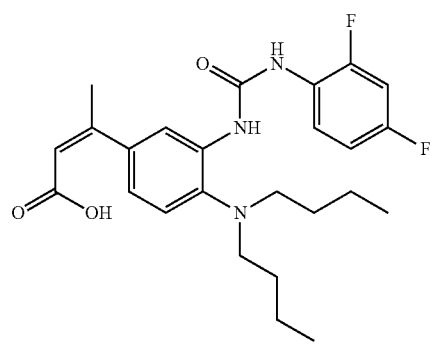

$^1$H-NMR (600 MHz, DMSO-$d_6$) δ (ppm): 0.85 (t, J=6.9 Hz, 6H), 1.45-1.17 (m, 8H), 2.50 (s, 3H), 2.87 (m, 4H), 5.86 (s, 1H), 6.85-7.32 (m, 4H), 8.05-8.00 (m, 1H), 8.25-8.32 (m, 1H), 8.66 (s, 1H), 9.40 (s, 1H). MS (ESI), m/z (%): 460.29 [M+H]$^+$. White solid.

Compound 14

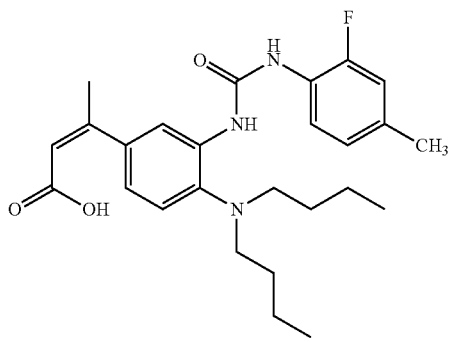

¹H-NMR (600 MHz, DMSO-d₆) δ (ppm): 0.85 (t, J=6.0 Hz, 6H), 1.17-1.37 (m, 8H), 2.27 (s, 3H), 2.50 (s, 3H), 2.86-2.90 (m, 4H), 5.85 (s, 1H), 6.83 (d, J=0.6 Hz, 1H), 6.95 (d, J=0.6 Hz, 1H), 7.06 (d, J=1.2 Hz, 1H), 7.16 (dd, J=4.2, 1.2 Hz, 1H), 7.88-7.94 (m, 1H), 8.33 (s, 1H), 8.63 (s, 1H), 9.28 (s, 1H). MS (ESI), m/z (%): 456.32[M+H]⁺. White solid.

Compound 56

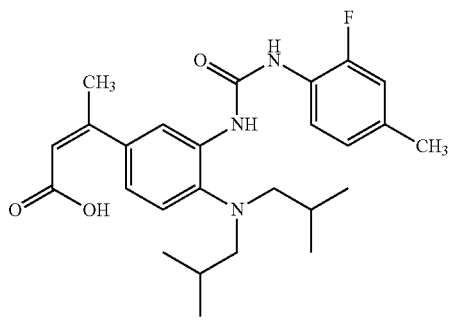

¹H-NMR (300 MHz, DMSO-d₆) δ (ppm): 9.28 (s, 1H), 8.63 (s, 1H), 8.33 (s, 1H), 7.88-7.94 (m, 1H), 7.16 (dd, J=4.2, 1.2 Hz, 1H), 7.06 (d, J=1.2 Hz, 1H), 6.95 (d, J=0.6 Hz, 1H), 6.83 (d, J=0.6 Hz, 1H), 5.85 (s, 1H), 2.86-2.90 (m, 4H), 2.48 (s, 3H), 2.10 (s, 3H), 1.63-1.71 (m, 2H), 0.82 (d, J=6.0 Hz, 12H). MS (ESI), m/z (%): 456.29[M+H]⁺. White solid.

Compound 51

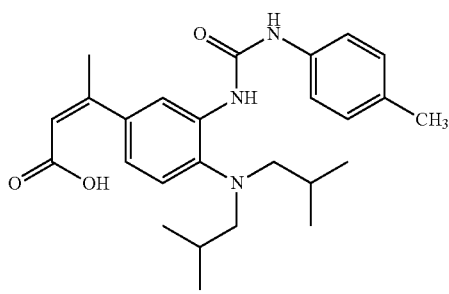

¹H-NMR (600 MHz, DMSO-d₆) δ 12.21 (s, 1H), 9.22 (s, 1H), 8.06 (s, 1H), 8.00 (s, 1H), 7.86 (t, J=8.5 Hz, 1H), 7.45 (d, J=15.8 Hz, 1H), 7.28 (d, J=9.6 Hz, 1H), 7.16 (d, J=8.4 Hz, 1H), 7.05 (d, J=12.2 Hz, 1H), 6.92 (d, J=8.0 Hz, 1H), 5.89 (s, 1H), 2.80 (d, J=6.9 Hz, 4H), 2.45 (d, J=0.7 Hz, 3H), 2.21 (s, 3H), 1.71 (dt, J=13.3, 6.7 Hz, 2H), 0.82 (d, J=6.6 Hz, 12H). MS (ESI), m/z (%): 438.30[M+H]⁺. White solid.

Compound 396

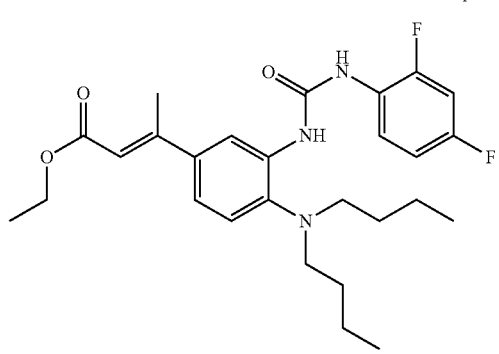

¹H-NMR (300 MHz, DMSO-d₆) δ (ppm): 0.85 (t, J=−6.9 Hz, 6H), 1.27-1.30 (m, 11H), 2.53 (s, 3H), 2.87-2.89 (m, 4H), 4.13 (q, J=6.9 Hz, 2H), 6.08 (s, 1H), 7.13-7.17 (m, 2H), 7.50 (d, J=9.3 Hz, 1H), 7.70 (d, J=9.3 Hz, 1H), 8.01 (s, 1H), 8.35 (s, 1H), 8.39 (s, 1H), 9.88 (s, 1H). MS (ESI), m/z (%): 488.55[M+H]⁺. White solid.

Compound 55

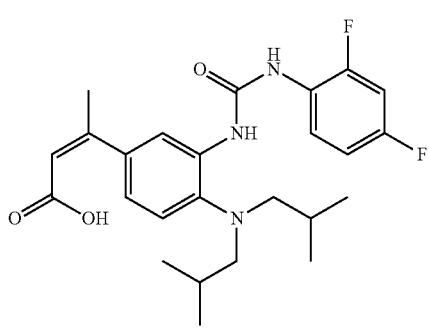

¹H-NMR (600 MHz, DMSO-d₆) δ 11.88 (s, OH), 9.28 (s, OH), 8.05 (s, 1H), 7.94 (td, J=9.1, 6.5 Hz, 1H), 7.78 (d, J=1.7 Hz, 1H), 7.34-7.24 (m, 1H), 7.13 (d, J=8.3 Hz, 1H), 7.04 (t, J=8.0 Hz, 1H), 6.87 (dd, J=8.2, 1.6 Hz, 1H), 5.84 (s, 1H), 2.70 (d, J=6.8 Hz, 4H), 2.09 (s, 3H), 1.71-1.66 (m, 2H), 0.85 (t, J=8.0 Hz, 12H). MS (ESI), m/z (%): 460.28[M+H]⁺. White solid.

Compound 397

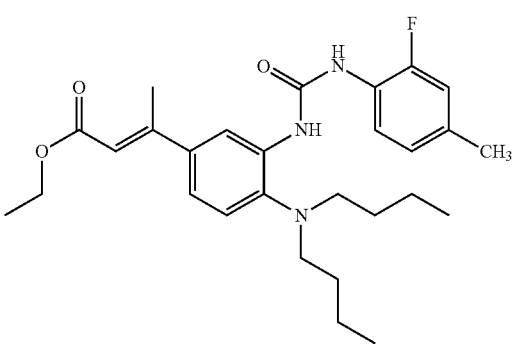

¹H-NMR (300 MHz, DMSO-d₆) δ (ppm): 0.84 (t, J=6.9 Hz, 6H), 1.20-1.30 (m, 11H), 2.30 (s, 3H), 2.52 (s, 3H), 2.86-2.88 (m, 4H), 4.12 (q, J=6.9 Hz, 2H), 6.07 (s, 1H), 6.87-6.96 (m, 3H), 7.09 (s, 1H), 7.95-8.01 (m, 1H), 8.35 (s, 1H), 8.61 (s, 1H), 9.21 (s, 1H). MS (ESI), m/z (%): 484.36[M+H]$^+$. White solid.

3H), 2.79 (d, J=12.0 Hz, 4H), 4.13 (q, J=6.0 Hz, 2H), 6.09 (s, 1H), 7.03-7.05 (m, 1H), 7.19-7.23 (m, 2H), 7.29-7.31 (t, =6 Hz, 1H), 7.98-8.01 (m, 1H), 8.05 (d, J=6.0 Hz, 1H), 8.09 (s, 1H), 9.33 (s, 1H). MS (ESI), m/z (%): 488.32[M+H]$^+$. White solid.

Compound 403

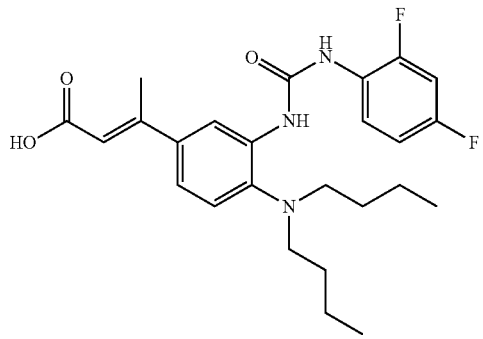

$^1$H-NMR (300 MHz, DMSO-d$_6$) δ (ppm): 0.85 (t, J=6.9 Hz, 6H), 1.19-1.34 (m, 8H), 2.49 (s, 3H), 2.86-2.91 (m, 4H), 6.05 (s, 1H), 6.91 (t, J=8.7 Hz, 3H), 7.00-7.12 (m, 3H), 8.10-8.19 (m, 1H), 8.32 (s, 1H), 8.26 (s, 1H), 8.63 (s, 1H), 9.32 (s, 1H). MS (ESI), m/z (%): 460.29[M+H]$^+$. White solid.

Compound 571

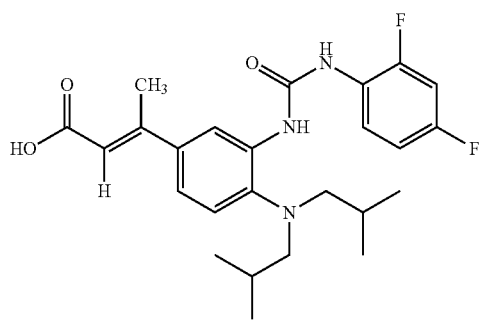

$^1$H-NMR (600 MHz, DMSO-d$_6$) δ (ppm): 9.31 (s, 1H), 8.08 (s, 1H), 8.05 (d, J=6.0 Hz, 1H), 7.98-8.03 (m, 1H), 7.29-7.31 (t, J=6 Hz, 1H), 7.19-7.24 (m, 2H), 7.01-7.06 (m, 1H), 6.05 (s, 1H), 2.86-2.90 (m, 4H), 2.48 (s, 3H), 1.69-1.72 (m, 2H), 0.82 (d, J=6.0 Hz, 12H). MS (ESI), m/z (%): 460.27[M+H]$^+$. White solid.

Compound 404

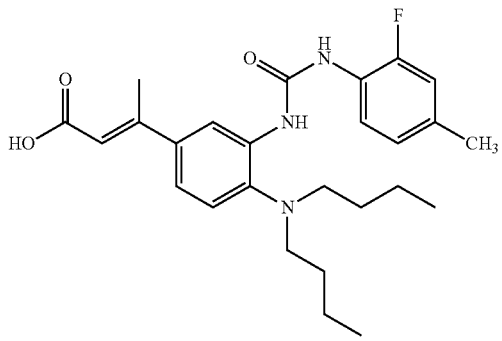

$^1$H-NMR (300 MHz, DMSO-d$_6$) δ (ppm): 0.85 (t, J=6.9 Hz, 6H), 1.20-1.30 (m, 8H), 1.80 (s, 3H), 2.43 (s, 3H), 2.84-2.89 (m, 4H), 6.05 (s, 1H), 6.86-6.94 (m, 2H), 7.03-7.11 (m, 2H), 7.95-8.00 (m, 1H), 8.29 (s, 1H), 8.59 (s, 1H), 9.19 (s, 1H). MS (ESI), m/z (%): 456.32 [M+H]$^+$. White solid.

Compound 572

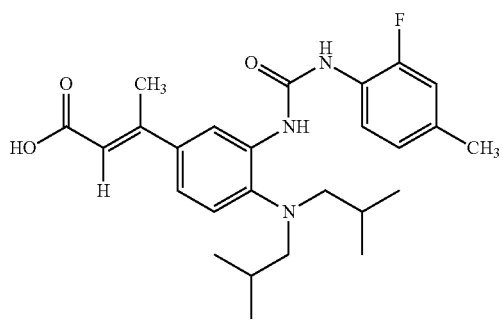

$^1$H-NMR (600 MHz, DMSO-d$_6$) δ (ppm): 12.11 (s, 1H), 9.23 (s, 1H), 8.07 (s, 1H), 8.02 (s, 1-), 7.86 (t, J=8.5 Hz, 1H), 7.19 (s, 2H), 7.06 (d, J=12.2 Hz, 1H), 6.95 (d, J=8.2 Hz, 1H), 6.06 (d, J=1.1 Hz, 1H), 2.77 (d, J=6.9 Hz, 4H), 2.46 (d, J=0.7 Hz, 3H), 2.27 (s, 3H), 1.70 (dt, J=13.4, 6.7 Hz, 2H), 0.83 (d, J=6.6 Hz, 12H). MS (ESI), m/z (%): 456.30[M+H]$^+$. White solid.

Compound 564

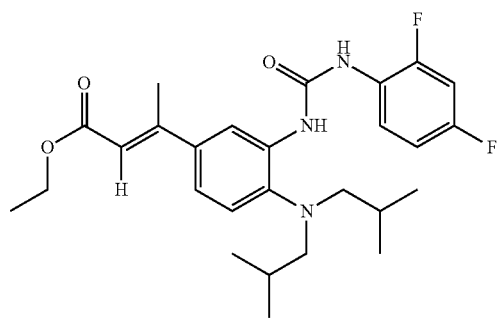

$^1$H-NMR (600 MHz, DMSO-d$_6$) δ (ppm): 0.83 (d, J=6.0 Hz, 12H), 1.24 (t, J=6.0 Hz, 3H), 1.69-1.72 (m, 2H), 2.49 (s, Compound 772

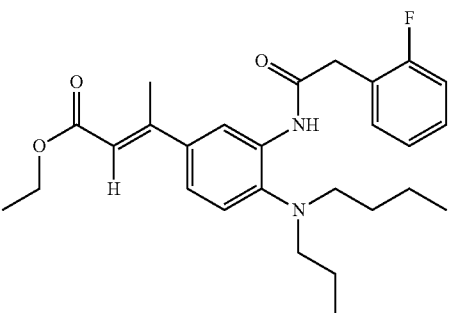

¹H-NMR (600 MHz, DMSO-d₆) δ (ppm): 0.80 (t, J=6.0 Hz, 6H), 1.14-1.25 (m, 11H), 2.48 (s, 3H), 2.73 (t, J=6.0 Hz, 4H), 3.83 (s, 2H), 4.13 (q, J=6.0 Hz, 2H), 6.08 (s, 1H), 7.22-7.25 (m, 4H), 7.37-7.40 (m, 1H), 7.46-7.48 (m, 1H), 8.40 (s, 1H), 8.90 (s, 1H). MS (ESI), m/z (%): 469.34 [M+H]⁺. White solid.

¹H-NMR (400 MHz, DMSO-d₆) δ 8.59 (s, 1H), 8.07 (d, J=1.9 Hz, 1H), 7.74 (s, 1H), 7.28 (d, J=8.0 Hz, 1H), 7.13 (dt, J=8.5, 5.3 Hz, 2H), 6.98 (s, 1H), 6.93 (d, J 8.4 Hz, 1H), 6.00 (s, 1H), 2.64 (d, J=6.9 Hz, 4H), 2.42 (s, 3H), 2.21 (s, 3H), 2.15 (s, 3H), 1.60 (dd, J=13.0, 6.4 Hz, 2H), 0.78 (d, J=6.6 Hz, 12H). MS (ESI), m/z (%): 452.32 [M+H]⁺. White solid.

Compound 779

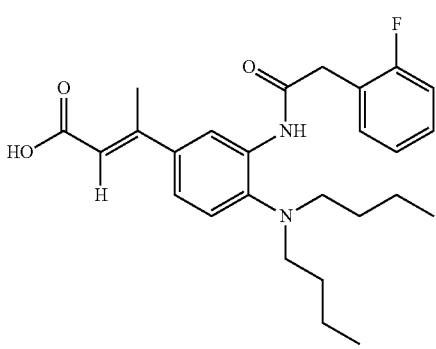

Compound 821

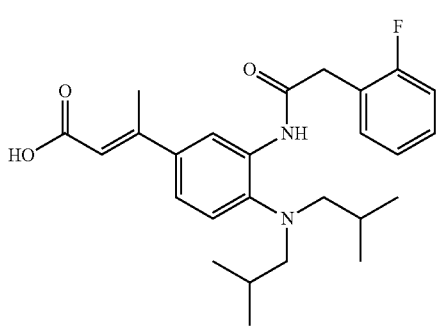

¹H-NMR (600 MHz, DMSO-d₆) δ (ppm): 0.80 (t, J=6.0 Hz, 6H), 1.13-1.23 (m, 8H), 2.45 (s, 3H), 2.71 (t, J=6.0 Hz, 4H), 3.83 (s, 2H), 6.05 (s, 1H), 7.22-7.27 (m, 4H), 7.37-7.40 (m, 1H), 7.46-7.48 (m, 1H), 8.39 (s, 1H), 8.89 (s, 1H), 12.18 (s, 1H). MS (ESI), m/z (%): 441.15 [M+H]⁺. White solid.

¹H-NMR (500 MHz, DMSO-d₆) δ 12.17 (s, 1H), 8.80 (d, J=15.8 Hz, 1H), 8.33 (s, 1H), 7.43 (t, J=7.4 l-Hz, 1H), 7.36 (dd, J=13.4, 6.2 Hz, 1H), 7.28 (s, 2H), 7.20 (dd, J=12.6, 5.3 Hz, 2H), 6.05 (s, 1H), 3.85-3.77 (m, 2H), 2.61 (t, J=12.7 Hz, 4H), 2.45 (s, 3H), 1.62 (dt, J=12.0, 6.0 Hz, 2H), 0.79 (d, J=6.6 Hz, 12H). MS (ESI), m/z (%): 441.27 [M+H]⁺. White solid.

Compound 818

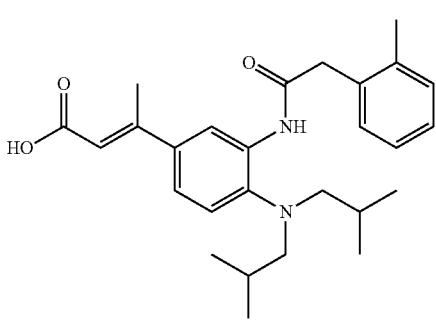

Compound 822

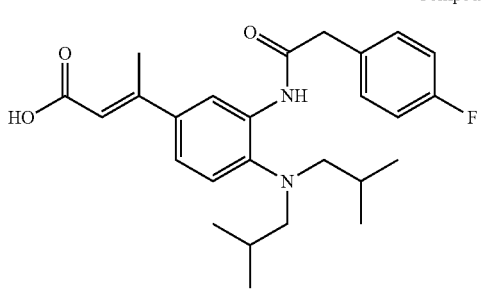

¹H-NMR (400 MHz, DMSO-d₆) δ 12.13 (s, 1H), 8.44 (s, 1H), 8.36 (s, 1H), 7.27-7.12 (m, 6H), 6.00 (s, 1H), 3.74 (s, 2H), 2.50 (s, 2H), 2.48 (s, 2H), 2.41 (s, 3H), 2.22 (s, 31-), 1.51 (dt, J=13.1, 6.4 Hz, 2H), 0.69 (d, J=6.5 Hz, 12H). MS (ESI), m/z (%): 437.31 [M+H]⁺. White solid.

¹H-NMR (600 MHz, DMSO-d₆) δ 12.16 (s, 1H), 8.72 (d, J=21.6 Hz, 1H), 8.30 (s, 1H), 7.38 (s, 2H), 7.31-7.13 (m, 4H), 6.04 (s, 1H), 3.74 (d, J=18.0 Hz, 2H), 2.59 (t, J=13.6 Hz, 4H), 2.45 (s, 3H), 1.59 (d, J=5.8 Hz, 2H), 0.77 (d, J=5.9 Hz, 12H). MS (ESI), m/z (%): 441.27 [M+H]⁺. White solid.

Compound 820

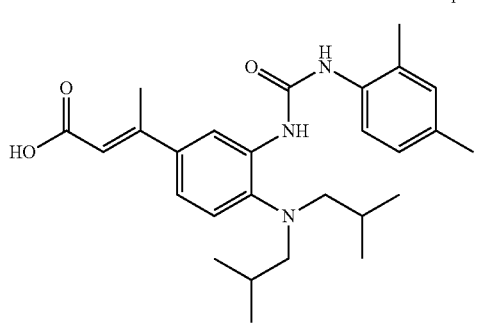

Compound 861

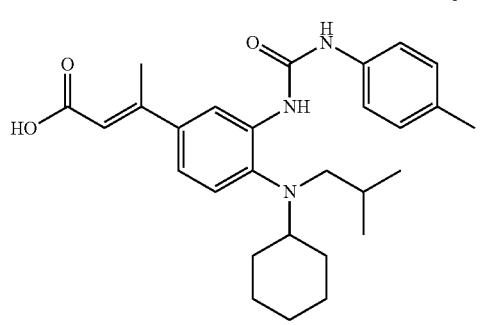

¹H-NMR (400 MHz, DMSO-d₆) δ 12.12 (s, 1H), 9.42 (s, 1H), 8.20 (d, J=2.1 Hz, 1H), 7.86 (s, 1H), 7.33 (d, J=8.4 Hz, 2H), 7.13 (dt, J=8.4, 5.3 Hz, 2H), 7.06 (d, J=8.3 Hz, 2H), 6.03 (d, J=1.2 Hz, 11H), 2.77 (d, J=5.3 Hz, 2H), 2.53 (t, J=10.7 Hz, 1H), 2.44 (d, J=1.0 Hz, 3H), 2.21 (s, 3H), 1.89-1.79 (m, 2H), 1.64 (d, J=11.7 Hz, 2H), 1.46 (d, J=10.7 Hz, 1H), 1.31 (ddd, J=22.4, 14.4, 7.9 Hz, 2H), 1.14 (ddd, J=30.5, 21.7, 12.0 Hz, 4H), 0.78 (d, J=6.6 Hz, 6H). MS (ESI), m/z (%): 464.33 [M+H]⁺. White solid.

Compound 1021

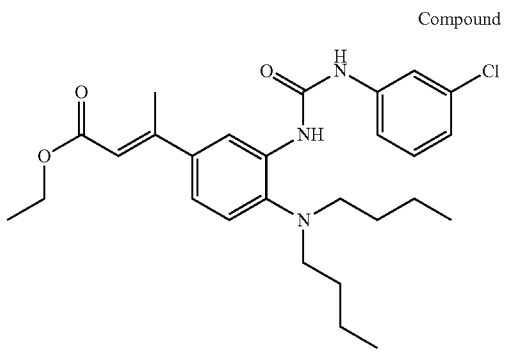

¹H-NMR (300 MHz, DMSO-d₆) δ (ppm): 0.86 (t, J=6.9 Hz, 61H), 1.19-1.37 (m, 11H), 2.53 (s, 3H), 2.89 (t, J=6.6 Hz, 4H), 4.14 (q, J=6.9 Hz, 2H), 6.09 (d, J=1.2 Hz, 1H), 6.90-6.94 (m, 1H), 7.07-7.15 (m, 2H), 7.19-7.28 (m, 2H), 7.72 (d, J=1.8 Hz, 1H), 8.33 (s, 1H), 8.37 (d, J=1.5 Hz, 1H), 9.57 (s, 1H). MS (ESI), m/z (%): 487.30[M+H]⁻. White solid.

Compound 1022

Compound 1022: R² is an ethyl ester group, and the olefinic bond is trans, and the specific structure is as follows:

¹H-NMR (300 MHz, DMSO-d₆) δ (ppm): 0.85 (t, J=6.9 Hz, 6H), 1.25-1.35 (m, 11H), 2.50 (s, 3H), 2.89 (m, 4H), 4.09-4.16 (m, 2H), 6.06 (s, 1H), 6.98-7.03 (m, 3H), 7.22-7.27 (m, 1H), 7.35-7.37 (m, 1H), 8.00 (d, J=8.1 Hz, 1H), 8.26 (s, 1H), 8.68 (s, 1H), 8.96 (s, 1H). MS (ESI), m/z (%): 487.29[M+H]⁺. White solid.

Compound 1023

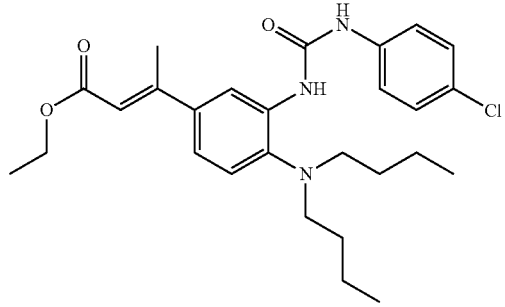

¹H-NMR (300 MHz, DMSO-d₆) δ (ppm): 0.85 (t, J=6.9 Hz, 6H), 1.18-1.33 (m, 11H), 2.53 (s, 3H), 2.86-2.92 (m, 4H), 4.13 (q, J=6.9 Hz, 2H), 7.07-7.15 (m, 2H), 7.23 (d, J=-9.0 Hz, 2H), 7.50 (d, J=9.0 Hz, 2H), 8.32 (s, 1H), 8.38 (s, 1H), 9.53 (s, 1H). MS (ESI), m/z (%): 487.29[M+H]⁺. White solid.

Compound 1024

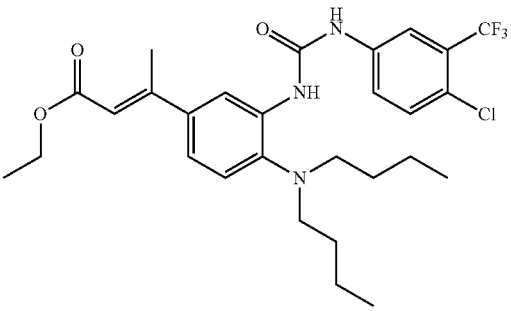

Compound 1024: R² is an ethyl ester group, and the olefinic bond is trans, and the specific structure is as follows:

¹H-NMR (300 MHz, DMSO-d₆) δ (ppm): 0.85 (t, J=6.9 Hz, 6H), 1.18-1.32 (m, 11H), 2.51 (s, 3H), 2.87-2.89 (m, 4H), 4.12 (q, J=6.9 Hz, 2H), 6.07 (s, 1H), 6.91-6.93 (m, 1H), 7.07-7.17 (m, 311), 8.12-8.14 (m, 1H), 8.33 (s, 1H), 8.36 (s, 1H), 9.31 (s, 1H). MS (ESI), m/z (%): 555.34[M+H]⁺. White solid.

Compound 1025

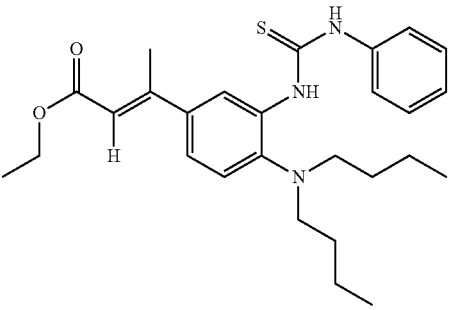

$R^2$ is an ethyl ester group, and the olefinic bond is trans, and the specific structure is as follows:

$^1$H-NMR (600 MHz, DMSO-d$_6$) δ (ppm): 0.79 (t, J=6.0 Hz, 6H), 1.15 (q, J=6.0 Hz, 4H), 1.23-1.27 (m, 7H), 2.50 (s, 3H), 2.82 (t, J=6.0 Hz, 4H), 3.83 (s, 2H), 4.14 (q, J=6.0, 2H), 6.08 (s, 1H), 7.16 (d, J=12 Hz, 1H), 7.22 (t, J=12 Hz, 1H), 7.34 (d, J=6.0 Hz, 1H), 7.39 (dd, J=12.0, 6.0 Hz, 2H), 7.48 (d, J=6.0 Hz, 2H), 8.45 (s, 1H), 8.97 (s, 1H), 10.37 (s, 1H). MS (ESI), m/z (%): 468.31 [M+H]$^+$. White solid.

Compound 1026

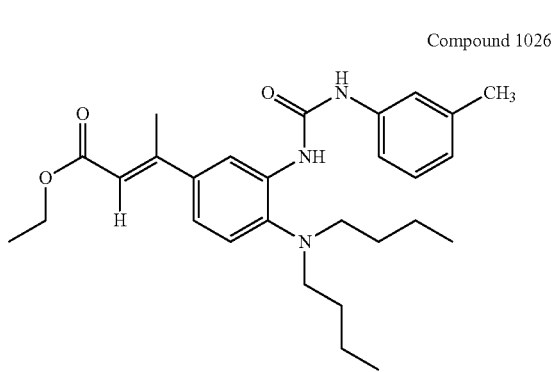 [SMILES: CCCCN(CCCC)c1ccc(/C(C)=C/C(=O)OCC)cc1NC(=O)Nc1cccc(C)c1]

$R^2$ is an ethyl ester group, and the olefinic bond is trans, and the specific structure is as follows:

$^1$H-NMR (600 MHz, DMSO-d$_6$) δ (ppm): 0.81 (t, J=6.0 Hz, 6H), 1.21-1.29 (m, 11H), 2.29 (s, 3H), 2.51 (s, 3H), 2.90 (t, J=6.0 Hz, 4I-), 4.15 (q, J=6.0 Hz, 4H), 6.11 (s, 1H), 6.80 (d, J=6.0 Hz, 1H), 7.15-7.25 (m, 4H), 7.36 (s, 1H), 8.35 (s, 1H), 8.39 (d, J=6.0 Hz 1H), 9.49 (s, 1H). MS (ESI), m/z (%): 466.36[M+H]$^+$. White solid.

Compound 1027

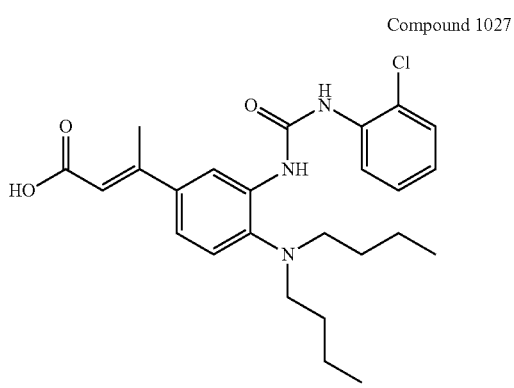 [SMILES: CCCCN(CCCC)c1ccc(/C(C)=C/C(=O)O)cc1NC(=O)Nc1ccccc1Cl]

$^1$H-NMR (600 MHz, DMSO-d$_6$) δ (ppm): 0.83 (t, J=6.0 Hz, 6H), 1.13-1.33 (m, 8H), 2.50 (s, 3H), 2.86-2.92 (m, 4H), 6.10 (s, 1H), 7.07-7.09 (m, 1H), 7.13-7.22 (m, 1H), 7.29-7.32 (m, 2H), 7.47 (d, J=12 Hz, 1H), 7.97 (s, 1H), 8.21 (s, 1H), 8.75 (s, 1H), 9.18 (s, 1H). MS (ESI), m/z (%): 459.27 [M+H]$^+$. White solid.

Compound 1028

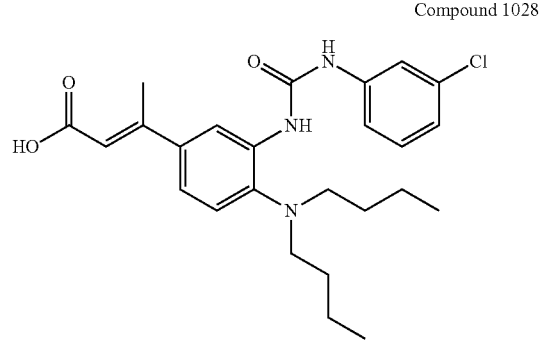 [SMILES: CCCCN(CCCC)c1ccc(/C(C)=C/C(=O)O)cc1NC(=O)Nc1cccc(Cl)c1]

$^1$H-NMR (600 MHz, DMSO-d$_6$) δ (ppm): 0.85 (t, J=6.0 Hz, 6H), 1.21-1.31 (m, 8H), 2.50 (s, 3H), 2.92 (m, 4H), 4.09-4.16 (m, 2H), 6.10 (s, 1H), 7.02-7.03 (m, 1H), 7.27-7.33 (m, 3H), 7.76 (m, 1H), 8.01 (d, J=7.8 Hz, 1H), 8.32 (s, 1H), 8.47 (s, 1H), 9.84 (s, 1H). MS (ESI), m/z (%): 459.29 [M+H]$^+$. White solid.

Compound 1030

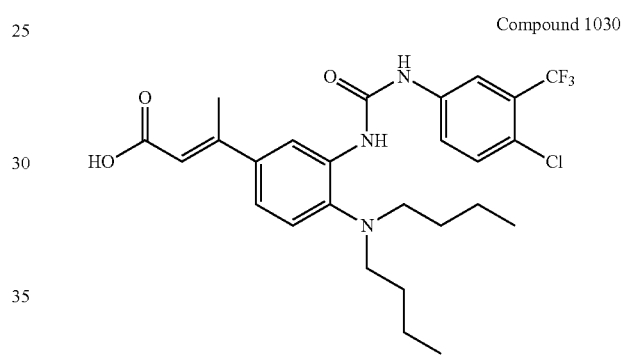

$^1$H-NMR (300 MHz, DMSO-d$_6$) δ (ppm): 0.85 (t, J=6.9 Hz, 6H), 1.24-1.30 (m, 8H), 2.56 (s, 3H), 2.87-2.90 (m, 4H), 6.05 (s, 1H), 7.12-7.16 (m, 2H), 7.46-7.50 (m, 1H), 7.71 (d, J=8.1 Hz, 1H), 8.35-8.38 (m, 2H), 9.85 (s, 1H). MS (ESI), m/z (%): 527.29[M+H]$^+$. White solid.

Compound 1031

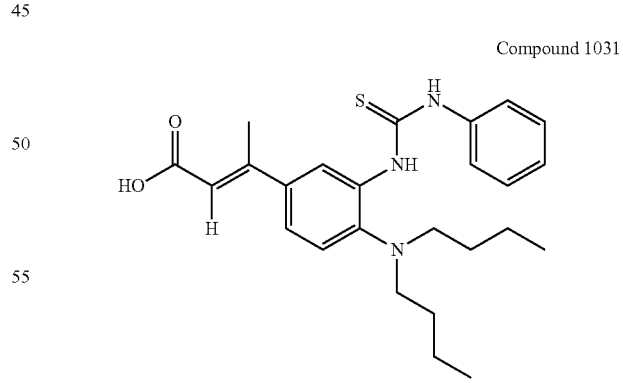

The olefinic bond is trans, Y is S substituted, and R is hydrogen. The specific structure is as follows:

$^1$H-NMR (600 MHz, DMSO-d$_6$) δ (ppm): 0.80 (t, J=6.0 Hz, 6H), 1.16 (q, J=6.0 Hz, 4H), 1.22-1.28 (m, 4H), 2.51 (s, 3H), 2.80 (t, J=6.0 Hz, 4H), 3.85 (s, 2H), 6.09 (s, —1H), 7.17 (d, J=12 Hz, 1H), 7.23 (t, J=12 Hz, 1H), 7.33 (d, J=6.0 Hz, 1H), 7.39 (dd, J=12.0, 6.0 Hz, 2H), 7.47 (d, J=6.0 Hz, 2H), 8.46 (s, 1H), 8.97 (s, 1H), 8.97 (s, 1H), 10.37 (s, 1H), 12.03 (s, 1H). MS (ESI), m/z (%): 440.27[M+H]⁺. White solid.

7.13 (dd, J=8.3, 1.8 Hz, 1H), 6.67 (s, 1H), 5.65 (s, 1H), 2.63 (d, J=7.2 Hz, 4H), 2.46 (s, 2H), 1.75 (dd, J=13.4, 6.7 Hz, 2H), 0.91 (d, J=6.5 Hz, 12H). MS (ESI), m/z (%): 473.23 [M+H]⁺. White solid.

Compound 1033

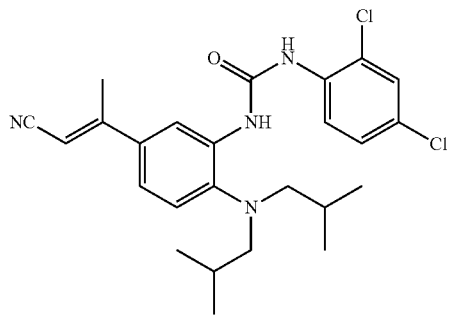

¹H-NMR (600 MHz, CDCl₃) δ (ppm): 8.37 (d, J=1.8 Hz, 1H), 8.13 (s, 1H), 7.60 (d, J=2.4 Hz, 1H), 7.38 (d, J=8.7 Hz, 1H), 7.27 (dd, J=9.5, 3.1 Hz, 1H), 7.18 (d, J=8.4 Hz, 1H), 7.12 (dd, J=8.3, 2.0 Hz, 1H), 6.48 (s, 1H), 5.64 (s, 1H), 2.62 (d, J=7.2 Hz, 4H), 2.46 (s, 3H), 1.73 (dp, J=13.4, 6.7 Hz, 2H), 0.90 (d, J=6.6 Hz, 12H). MS (ESI), m/z (%): 474.31 [M+H]⁺. White solid.

Compound 1036

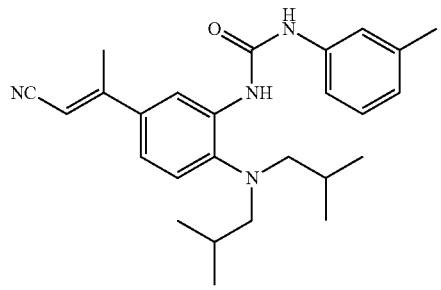

¹H-NMR (600 MHz, CDCl₃) δ (ppm): 8.43 (s, 1H), 8.03 (s, 1H), 7.29-7.17 (m, 2H), 7.14 (d, J=8.5 Hz, 2H), 7.09 (d, J=8.3 Hz, 1H), 6.97 (d, J=7.5 Hz, 1H), 6.40 (s, 1H), 5.64 (s, 1H), 2.57 (d, J=7.2 Hz, 4H), 2.46 (s, 3H), 2.35 (s, 3H), 1.68 (m, 2H), 0.83 (d, J=6.6 Hz, 12H). MS (ESI), m/z (%): 419.35[M+H]⁺. White solid.

Compound 1034

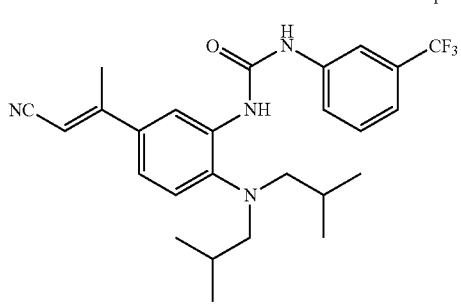

¹H-NMR (600 MHz, CDCl₃) δ (ppm): 8.39 (d, J=1.8 Hz, 1H), 8.15 (s, 1H), 7.66 (d, J=9.8 Hz, 2H), 7.46 (t, J=7.8 Hz, 1H), 7.36 (d, J=7.7 Hz, 1H), 7.19 (d, J=8.3 Hz, 1H), 7.12 (dd, J=8.3, 2.0 Hz, 1H), 6.54 (s, 1H), 5.65 (s, 1H), 2.62 (d, J=7.2 Hz, 4H), 2.46 (s, 3H), 1.83-1.65 (m, 2H), 0.90 (d, J=6.6 Hz, 12H). MS (ESI), m/z (%): 473.29[M+H]⁺. White solid.

Compound 1037

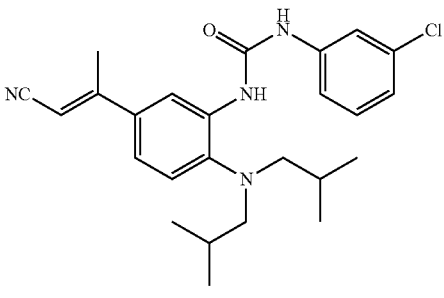

¹H-NMR (600 MHz, CDCl₃) δ (ppm): 8.39 (d, J=1.8 Hz, 1H), 8.12 (s, 1H), 7.46 (s, 1H), 7.27 (d, J=5.6 Hz, 2H), 7.17 (d, J=8.3 Hz, 1H), 7.11 (d, J=7.8 Hz, 2H), 6.41 (s, 1H), 5.64 (s, 1H), 2.60 (d, J=7.2 Hz, 4H), 2.46 (s, 3H), 1.72 (m, 2H), 0.88 (d, J=6.6 Hz, 12H). MS (ESI), m/z (%): 440.27[M+H]⁺. White solid.

Compound 1035

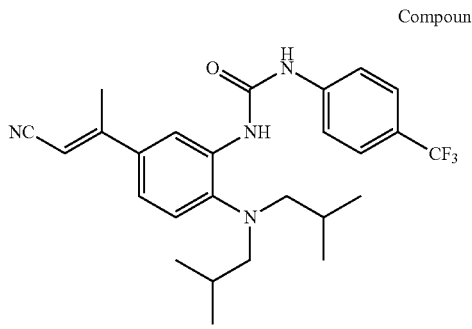

¹H-NMR (600 MHz, CDCl₃) δ (ppm): 8.38 (d, J=1.7 Hz, 1H), 8.17 (s, 1H), 7.66-7.48 (m, 4H), 7.19 (d, J 8.4 Hz, 1H), Compound 1038

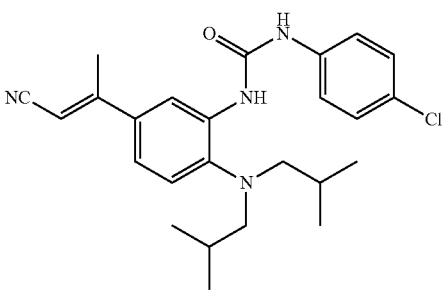

¹H-NMR (600 MHz, CDCl₃) δ (ppm): 8.39 (s, 1H), 8.09 (s, 1H), 7.32 (dd, J=25.8, 8.0 Hz, 4H), 7.17 (d, J=8.3 Hz, 1H), 7.11 (d, J=8.3 Hz, 1H), 6.40 (s, 1H), 5.64 (s, 1H), 2.59

(d, J=6.9 Hz, 4H), 2.46 (s, 3H), 1.81-1.64 (m, 2H), 0.88 (d, J=6.3 Hz, 12H). MS (ESI), m/z (%): 440.27[M+H]⁺. White solid.

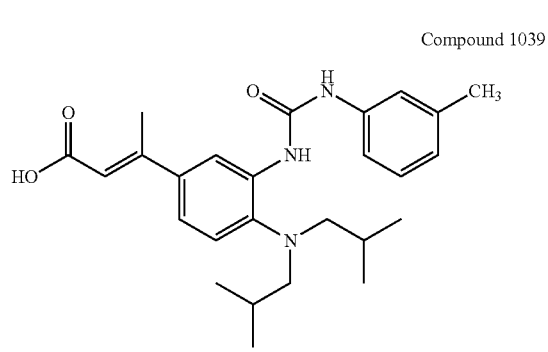 [SMILES: C/C(=C\C(=O)O)c1ccc(N(CC(C)C)CC(C)C)c(NC(=O)Nc2cccc(C)c2)c1]

Compound 1039

¹H-NMR (600 MHz, DMSO-d₆) δ (ppm): 12.13 (s, 1H), 9.42 (s, 1H), 8.16 (d, J=1.9 Hz, 1H), 7.80 (s, 1H), 7.35 (s, 1H), 7.21 (ddd, J=22.3, 20.0, 7.9 Hz, 4H), 6.80 (d, J=7.4 Hz, 1H), 6.07 (s, 1H), 2.74 (d, J=6.9 Hz, 4H), 2.48 (s, 3H), 2.29 (s, 3H), 1.68 m, 2H), 0.90-0.78 (m, 12H). MS (ESI), m/z (%): 438.30[M+H]⁺. White solid.

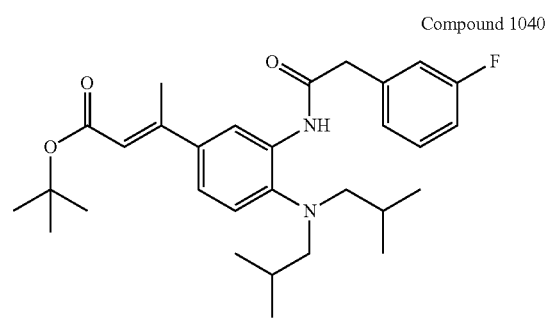 [SMILES: C/C(=C\C(=O)OC(C)(C)C)c1ccc(N(CC(C)C)CC(C)C)c(NC(=O)Cc2cccc(F)c2)c1]

Compound 1040

¹H-NMR (400 MHz, DMSO-d₆) δ 8.66 (s, 1H), 8.24 (s, 1H), 7.33 (dd, J=8.3, 5.7 Hz, 2H), 7.24-7.18 (m, 2H), 7.13 (t, J=8.9 Hz, 2H), 5.91 (d, J=1.1 Hz, 1H), 3.71 (s, 2H), 2.54 (t, J=10.5 Hz, 4H), 2.39 (d, J=0.9 Hz, 3H), 1.55 (dt, J=13.2, 6.4 Hz, 2H), 1.42 (s, 9H), 0.73 (t, J=6.6 Hz, 12H). MS (ESI), m/z (%): 497.39 [M+H]⁺. White solid.

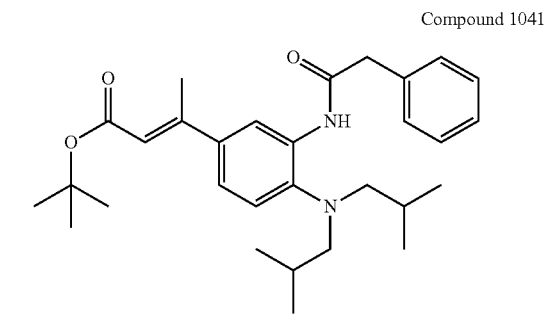 [SMILES: C/C(=C\C(=O)OC(C)(C)C)c1ccc(N(CC(C)C)CC(C)C)c(NC(=O)Cc2ccccc2)c1]

Compound 1041

¹H-NMR (600 MHz, DMSO-d₆) δ 8.71 (d, J=34.7 Hz, 1H), 8.31 (s, 1H), 7.38-7.31 (m, 4H), 7.28 (t, J=6.4 Hz, 2H), 7.24 (d, J=8.3 Hz, 2H), 5.95 (d, J=1.2 Hz, 1H), 3.73 (d, J=22.4 Hz, 2H), 2.64-2.53 (m, 4H), 2.43 (d, J=1.0 Hz, 3H), 1.58 (dt, J=13.3, 6.5 Hz, 2H), 1.46 (s, 9H), 0.76 (d, J=6.6 Hz, 12H). MS (ESI), m/z (%): 479.37 [M+H]⁺. White solid.

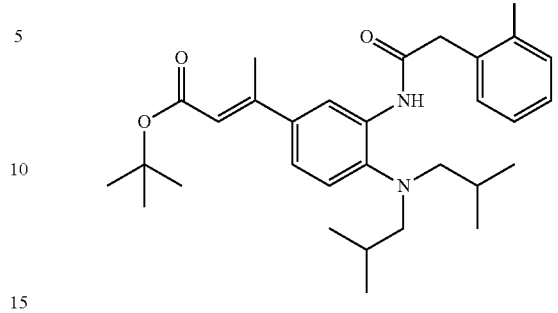

Compound 1042

¹H-NMR (600 MHz, DMSO-d₆) 8.79 (d, J=17.0 Hz, 1H), 8.30 (s, 1H), 7.43 (t, J=7.5 Hz, 1H), 7.35 (dd, J=13.8, 7.1 Hz, 1H), 7.27 (s, 2H), 7.20 (dd, J=12.8, 5.9 Hz, 2H), 5.95 (d, J=1.2 Hz, 1H), 3.78 (d, J=25.1 Hz, 2H), 2.59 (dd, J=35.8, 6.6 Hz, 4H), 2.44 (d, J=1.1 Hz, 3H), 1.65-1.56 (nm, 2H), 1.46 (s, 9H), 0.80 (t, J=6.2 Hz, 12H). MS (ESI), m/z (%): 497.39 [M+H]⁺. White solid.

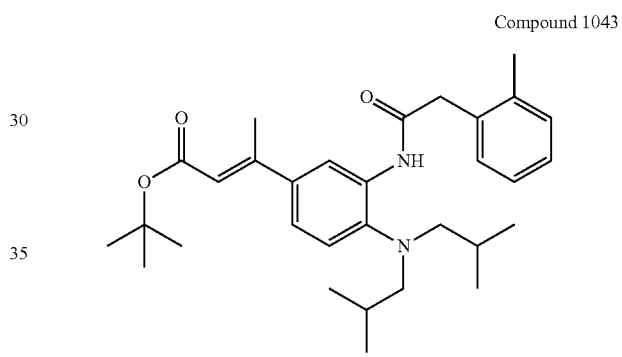

Compound 1043

¹H-NMR (600 MHz, DMSO-d₆) δ 8.48 (s, 1H), 8.38 (s, 1H), 7.32-7.08 (m, 6H), 5.96 (s, 1H), 3.76 (d, J=21.2 Hz, 2H), 2.53 (t, J=9.0 Hz, 4H), 2.44 (s, 3H), 2.25 (d, J=12.5 Hz, 3H), 1.56 (td, J=13.1, 6.5 Hz, 2H), 1.46 (s, 9H), 0.73 (d, J=6.6 Hz, 12H). MS (ESI), m/z (%): 493.41 [M+H]⁺. White solid.

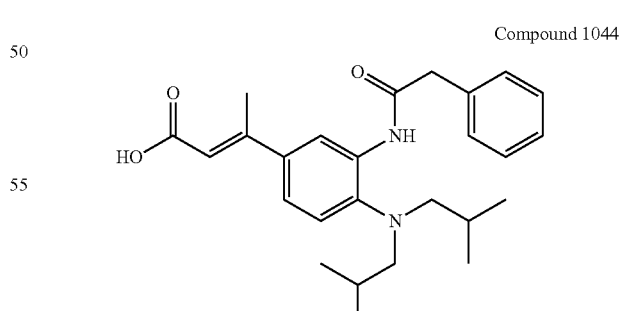

Compound 1044

¹H-NMR (600 MHz, DMSO-d₆) δ 12.14 (s, 1H), 8.71 (d, J=28.8 Hz, 1H), 8.33 (s, 1H), 7.39-7.18 (m, 7H), 6.04 (s, 1H), 3.73 (d, J=19.9 Hz, 2H), 2.56 (dd, J=29.0, 6.8 Hz, 4H), 2.45 (s, 3H), 1.67-1.48 (m, 2H), 0.77 (t, J=9.6 Hz, 12H). MS (ESI), m/z (%): 423.28 [M+H]⁺. White solid.

Compound 1045

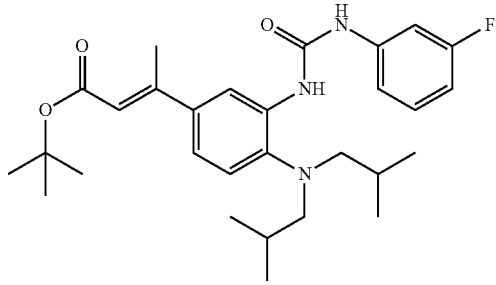

¹H-NMR (400 MHz, DMSO-d₆) δ 9.69 (s, 1H), 8.06 (d, J=1.7 Hz, 1H), 7.82 (s, 1H), 7.48 (d, J=12.0 Hz, 1H), 7.28 (dd, J=15.2, 8.1 Hz, 1H), 7.15 (ddd, J=16.2, 14.1, 8.2 Hz, 3H), 6.80-6.72 (m, 1H), 5.94 (s, 1H), 2.69 (t, J=10.2 Hz, 4H), 2.42 (s, 3H), 1.64 (dt, J=13.2, 6.5 Hz, 2H), 1.43 (s, 9H), 0.80 (d, J=6.6 Hz, 12H). MS (ESI), m/z (%): 498.37 [M+H]⁺. White solid.

Compound 1046

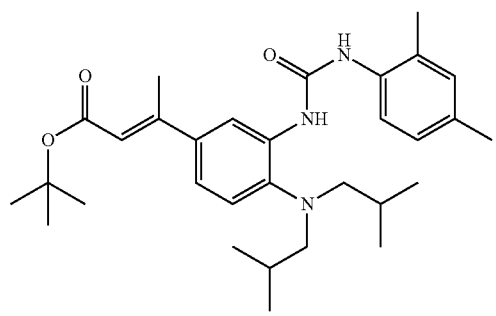

¹H-NMR (400 MHz, DMSO-d₆) δ 8.57 (d, J=22.5 Hz, 1H), 8.06 (d, J=2.0 Hz, 1H), 7.72 (d, J=18.3 Hz, 1H), 7.31 (dd, J=28.4, 9.0 Hz, 1H), 7.12 (dt, J=8.4, 5.3 Hz, 2H), 6.98 (s, 1H), 6.93 (d, J=8.1 Hz, 1H), 5.92 (d, J=1.2 Hz, 1H), 2.70-2.56 (m, 4H), 2.43-2.34 (m, 3H), 2.20 (d, J=8.3 Hz, 3H), 2.16 (d, J=8.7 Hz, 3H), 1.60 (td, J=13.2, 6.5 Hz, 2H), 1.47-1.33 (m, 9H), 0.85-0.71 (m, 12H). MS (ESI), m/z (%): 508.41 [M+H]⁺. White solid.

Compound 1047

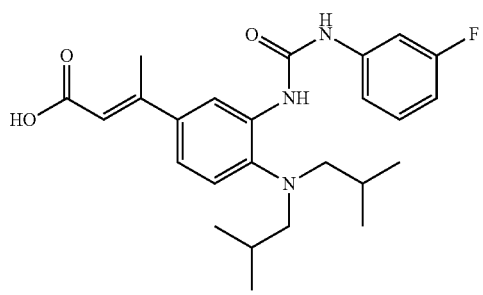

¹H-NMR (400 MHz, DMSO-d₆) δ 9.72 (s, 1H), 8.08 (d, J=2.0 Hz, 1H), 7.84 (s, 1H), 7.49 (d, J=12.0 Hz, 1H), 7.29-7.24 (m, 1H), 7.21-7.15 (m, 2H), 7.11 (d, J=7.9 Hz, 1H), 6.77-6.72 (m, 1H), 6.03 (d, J=1.1 Hz, 1H), 2.71 (d, J=6.9 Hz, 4H), 2.43 (s, 3H), 1.64 (dd, J=11.9, 5.4 Hz, 2H), 0.81 (t, J=6.2 Hz, 12H). MS (ESI), m/z (%): 442.29 [M+H]⁺. White solid.

Compound 1048

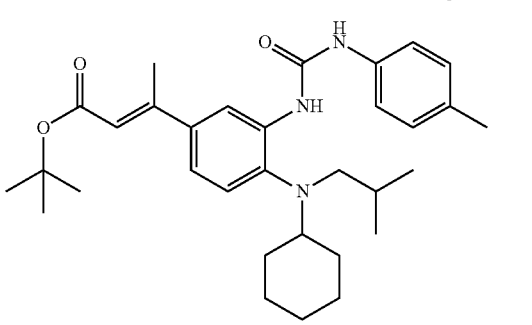

¹H-NMR (500 MHz, DMSO-d₆) δ 9.45 (s, 1H), 8.22 (d, J=2.2 Hz, 1H), 7.91 (s, 1H), 7.36 (dd, J=10.7, 5.5 Hz, 2H), 7.19 (d, J=8.4 Hz, 1H), 7.15 (dd, J=8.3, 2.2 Hz, 1H), 7.10 (d, J=8.3 Hz, 2H), 5.99 (d, J=1.2 Hz, 1H), 2.81 (d, J=5.0 Hz, 2H), 2.58 (dd, =23.5, 11.8 Hz, 1H), 2.47 (d, J=1.0 Hz, 3H), 2.25 (s, 3H), 1.87 (d, J=11.1 Hz, 2H), 1.69 (d, J=12.5 Hz, 2H), 1.51 (d, J=8.4 Hz, 1H), 1.48 (s, 9H), 1.33 (ddd, J=25.1, 12.5, 5.5 Hz, 2H), 1.29-1.21 (m, 4H), 0.83 (d, J=6.6 Hz, 6H). MS (ESI), m/z (%): 520.40 [M+H]⁺. White solid.

Compound 1049

¹H-NMR (500 MHz, DMSO-d₆) δ 8.89 (s, 2H), 8.04 (td, J=9.1, 6.3 Hz, 1H), 7.68 (d, J=2.2 Hz, 1H), 7.36-7.19 (m, 2H), 7.02 (dd, J=11.4, 4.8 Hz, 1H), 6.87 (d, J=8.5 Hz, 1H), 5.95 (s, 1H), 3.19 (q, J=7.1 Hz, 2H), 2.43 (s, 3H), 1.44 (s, 9H), 1.22 (dd, J=9.1, 5.1 Hz, 3H). MS (ESI), m/z (%): 432.22 [M+H]⁺. White solid.

Compound 1050

¹H-NMR (600 MHz, DMSO-d₆) δ 9.40 (s, 1H), 8.71 (s, 11H), 8.53 (s, 1H), 8.20-8.07 (m, 1H), 7.46 (dd, J=15.3, 8.8 Hz, 1H), 7.27 (s, 1H), 7.08-6.96 (m, 2H), 6.05 (s, 1H), 3.28 (d, J=57.3 Hz, 2H), 2.50 (s, 3H), 1.48 (s, 9H), 1.04 (t, J=6.9 Hz, 3H) MS (ESI), m/z (%): 432.23 [M+H]⁺. White solid.

Compound 1051

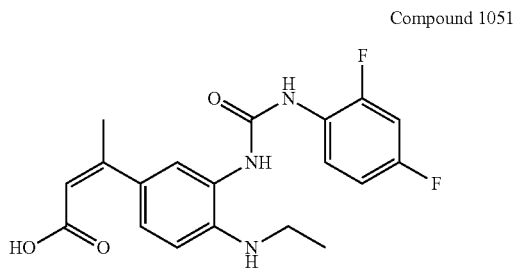 [SMILES: CCNc1ccc(/C(C)=C\C(=O)O)cc1NC(=O)Nc1ccc(F)cc1F]

¹H-NMR (600 MHz, DMSO-d₆) δ 11.88 (s, 1H), 8.63 (s, 1H), 8.21-8.03 (m, 2H), 7.61 (s, 1H), 7.38-7.22 (m, 2H), 7.00 (dt, J=10.3, 5.5 Hz, 1H), 6.66 (d, J=8.6 Hz, 1H), 6.01 (s, 1H), 3.14 (t, J=12.4 Hz, 2H), 2.46 (s, 3H), 1.22 (t, J=7.1 Hz, 3H). MS (ESI), m/z (%): 376.16 [M+H]⁺. White solid.

Compound 1052

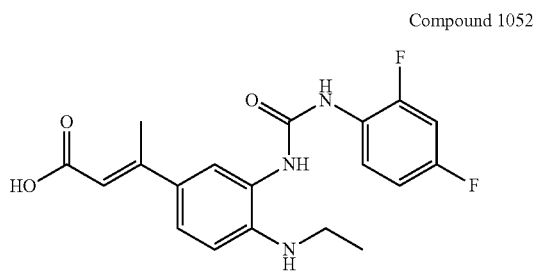 [SMILES: CCNc1ccc(/C(C)=C/C(=O)O)cc1NC(=O)Nc1ccc(F)cc1F]

¹H-NMR (600 MHz, DMSO-d₆) δ 12.26 (s, 1H), 9.40 (s, 1H), 8.72 (s, 1H), 8.57 (s, 1H), 8.21-8.10 (m, 1H), 7.54 (d, J=16.3 Hz, 1H), 7.46 (dd, J=15.6, 7.7 Hz, 1H), 7.25-7.17 (m, 1H), 7.01 (ddd, J=22.5, 16.5, 9.2 Hz, 2H), 6.14 (s, 1H), 3.93 (s, 1H), 3.23 (s, 1H), 2.53-2.51 (m, 3H), 1.05 (t, J=7.1 Hz, 3H). MS (ESI), m/z (%): 376.16 [M+H]⁺. White solid.

Compound 1053

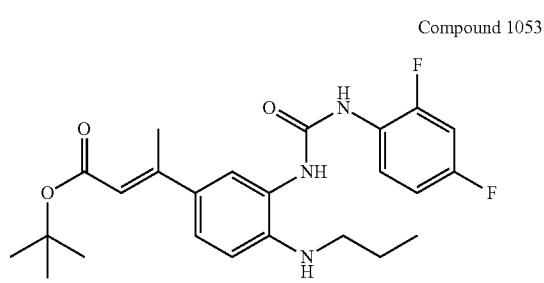 [SMILES: CCCNc1ccc(/C(C)=C/C(=O)OC(C)(C)C)cc1NC(=O)Nc1ccc(F)cc1F]

¹H-NMR (400 MHz, DMSO-d₆) δ 9.37 (s, 1H), 8.66 (s, 1H), 8.49 (d, J=1.6 Hz, 1H), 8.11 (dd, J=9.2, 3.1 Hz, 1H), 7.50 (s, 1H), 7.40 (dd, J=9.0, 2.7 Hz, 1H), 7.23 (d, J=1.4 Hz, 1H), 7.03 (d, J=9.1 Hz, 1H), 6.95 (d, J=7.7 Hz, 1H), 6.00 (d, J=1.2 Hz, 1H), 3.81 (s, 2H), 3.04 (s, 2H), 2.46 (s, 3H), 1.44 (s, 9H), 0.79 (t, J=7.4 Hz, 3H). MS (ESI), m/z (%): 446.23 [M+H]⁺. White solid.

Compound 1054

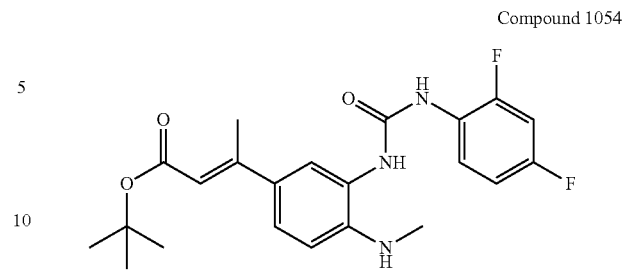

¹H-NMR (400 MHz, DMSO-d₆) δ 9.33 (s, 1H), 8.72 (s, 1H), 8.47 (d, J=2.0 Hz, 1H), 8.12 (td, J=9.3, 6.1 Hz, 1H), 7.69 (s, 1H), 7.27 (s, 1H), 7.03 (d, J=9.2 Hz, 1H), 6.95 (d, J=9.0 Hz, 1H), 6.00 (d, J=1.2 Hz, 1H), 3.07 (s, 3H), 2.45 (d, J=1.1 Hz, 3H), 1.44 (s, 9H). MS (ESI), m/z (%): 418.22 [M+H]⁺. White solid.

Compound 1055

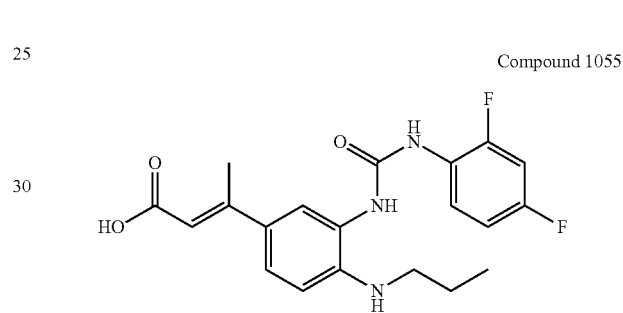

¹H-NMR (600 MHz, DMSO-d₆) δ 12.63-11.42 (m, 1H), 9.24 (s, 1H), 8.83-8.55 (m, 2H), 8.36-8.14 (m, 1H), 7.98 (s, 1H), 7.25 (dd, J=33.2, 25.4 Hz, 2H), 6.88-6.81 (m, 2H), 6.21 (s, 1H), 4.02 (s, 1H), 3.20 (s, 1H), 2.65-2.59 (m, 3H), 1.64 (s, 2H), 0.92 (dd, J=14.9, 7.4 Hz, 3H). MS (ESI), m/z (%): 390.21 [M+H]⁺. White solid.

Compound 1056

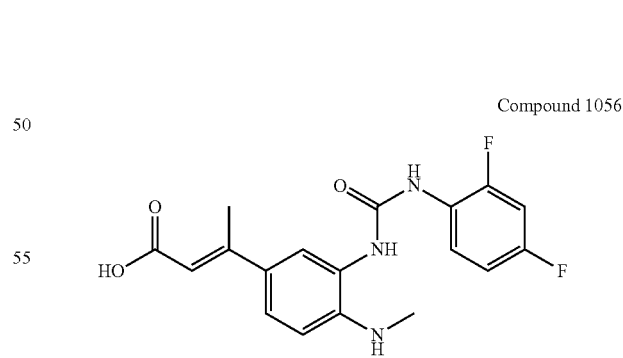

¹H-NMR (600 MHz, DMSO-d₆) δ 9.17-9.02 (m, 1H), 8.70 (d, J=46.5 Hz, 2H), 8.22 (dd, J=15.1, 9.1 Hz, 1H), 7.96 (s, 1H), 7.30 (s, 2H), 6.86-6.80 (m, 2H), 6.21 (s, 1H), 3.27 (d, J=5.4 Hz, 3H), 2.58 (s, 3H). MS (ESI), m/z (%): 362.26 [M+H]⁺. White solid.

Compound 1057

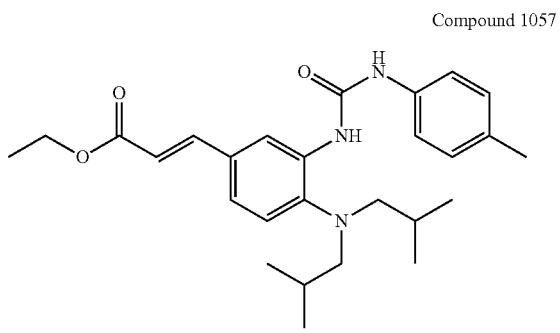 [SMILES: CCOC(=O)/C=C/c1ccc(N(CC(C)C)CC(C)C)c(NC(=O)Nc2ccc(C)cc2)c1]

¹H-NMR (400 MHz, CDCl₃) δ 8.45 (s, 1H), 7.96 (s, 1H), 7.63 (d, J=16.0 Hz, 1H), 7.21 (s, 1H), 7.14 (s, 1H), 7.11 (s, 3H), 6.41 (d, J=16.0 Hz, 1H), 4.22 (q, J=7.1 Hz, 2H), 2.53 (d, J=7.2 Hz, 4H), 2.32 (s, 3H), 1.65 (dt, J=13.5, 6.7 Hz, 2H), 1.31 (t, J=7.1 Hz, 3H), 0.79 (d, J=6.6 Hz, 12H). MS(ESI), m/z (%): 452.34 [M+H]⁺. White solid.

Compound 1058

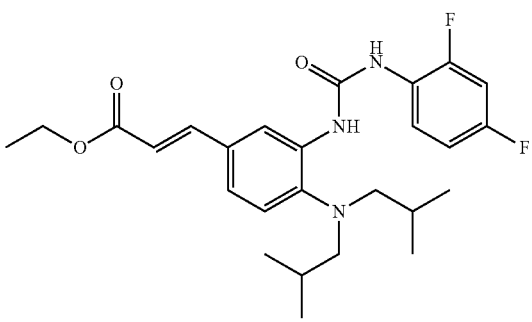

¹H-NMR (400 MHz, CDCl₃) δ 8.41 (s, 1H), 8.18 (s, 1H), 7.99 (td, J=9.2, 6.0 Hz, 1H), 7.63 (d, J=16.0 Hz, 1H), 7.14 (s, 2H), 6.90-6.81 (m, 2H), 6.39 (s, 1H), 4.23 (q, J=7.1 Hz, 2H), 2.59 (d, J=7.3 Hz, 4H), 1.72 (dt, J=13.5, 6.8 Hz, 2H), 1.31 (t, J=7.1 Hz, 3H), 0.88 (d, J=6.6 Hz, 12H). MS(ESI), m/z (%): 474.33 [M+H]⁺. White solid.

Compound 1059

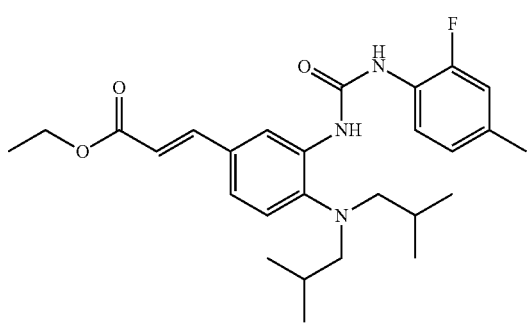

¹H-NMR (400 MHz, CDCl₃) δ 8.43 (s, 1H), 8.14 (s, 1H), 7.86 (t, J=8.4 Hz, 1H), 7.63 (d, J=16.0 Hz, 1H), 7.13 (s, 2H), 6.91 (dd, J=13.5, 10.4 Hz, 2H), 6.42 (d, J=16.0 Hz, 1H), 4.22 (q, J=7.1 Hz, 2H), 2.58 (d, J=7.2 Hz, 4H), 2.30 (s, 3H), 1.71 (dt, J=13.5, 6.8 Hz, 2H), 1.31 (t, J=7.1 Hz, 3H), 0.87 (d, J=6.6 Hz, 12H). MS(ESI), m/z (%): 470.31 [M+H]⁺. White solid.

Compound 1060

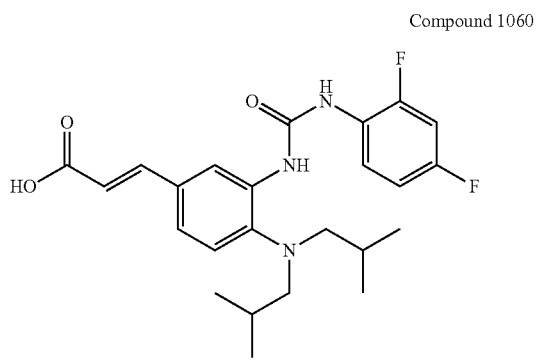 [SMILES: CC(C)CN(CC(C)C)c1ccc(/C=C/C(=O)O)cc1NC(=O)Nc1ccc(F)cc1F]

¹H-NMR (600 MHz, DMSO-d₆) δ 12.28 (s, 1H), 9.33 (s, 1H), 8.05 (d, J=15.7 Hz, 3H), 7.49 (d, J=15.8 Hz, 1H), 7.30 (d, J=8.3 Hz, 2H), 7.20 (s, 1H), 7.05 (s, 1H), 6.34-6.26 (m, 1H), 2.81 (d, J=6.3 Hz, 4H), 1.77-1.65 (m, 2H), 0.83 (d, J=6.1 Hz, 12H). MS(ESI), m/z (%): 446.23 [M+H]⁺. White solid.

Compound 1061

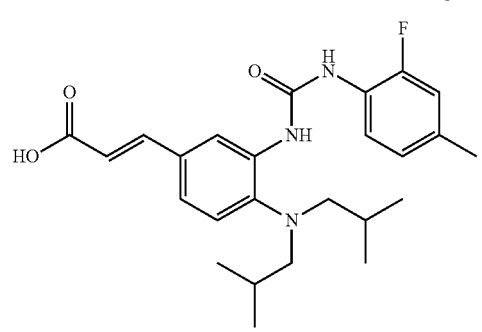

¹H-NMR (600 MHz, DMSO-d₆) δ 12.30 (s, 1H), 9.22 (s, 1H), 8.06 (s, 1H), 8.01 (s, 11H), 7.88 (t, J=8.5 Hz, 1H), 7.47 (d, J=15.8 Hz, 1H), 7.28 (d, J=9.6 Hz, 1H), 7.18 (d, J=8.4 Hz, 1H), 7.07 (d, J=12.2 Hz, 1H), 6.95 (d, J=8.0 Hz, 1H), 6.30 (d, J=15.9 Hz, 1H), 2.80 (d, J=6.9 Hz, 4H), 2.27 (s, 3H), 1.71 (dt, J=13.3, 6.7 Hz, 2H), 0.82 (d, J=6.6 Hz, 12H). MS(ESI), m/z (%): 442.25 [M+H]⁺. White solid.

Compound 1062

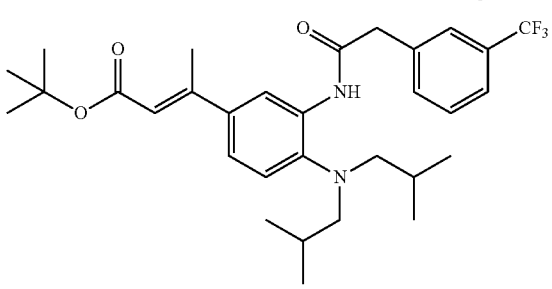

¹H-NMR (600 MHz, DMSO-d₆) δ 8.81 (s, 1H), 8.24 (s, 1H), 7.73 (s, 1H), 7.66 (s, 1H), 7.59 (s, 1H), 7.56 (s, 1H), 7.51 (s, 11H), 7.26 (d, J=2.1 Hz, 1H), 7.24 (s, 1H), 5.97 (s, 1H), 3.91 (s, 2H), 2.61 (d, J=7.1 Hz, 4H), 2.44 (s, 3H), 1.60 (dd, J=13.4, 6.7 Hz, 2H), 1.46 (s, 9H), 0.77 (d, J=6.6 Hz, 12H). MS(ESI), m/z (%): 547.38 [M+H]⁺. White solid.

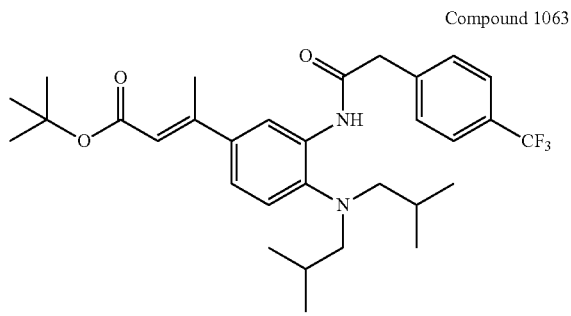 [SMILES: C/C(=C\C(=O)OC(C)(C)C)c1ccc(N(CC(C)C)CC(C)C)c(NC(=O)Cc2ccc(C(F)(F)F)cc2)c1]

Compound 1063

¹H-NMR (600 MHz, DMSO-d₆) δ 8.77 (s, 1H), 8.24 (s, 1H), 7.73 (d, J=1.5 Hz, 1H), 7.66 (s, 2H), 7.51 (d, J=2.7 Hz, 1H), 7.42 (s, 2H), 5.95 (s, 1H), 3.89 (s, 2H), 2.60 (d, J=7.1 Hz, 4H), 2.44 (s, 3H), 1.59 (dd, J=13.3, 6.6 Hz, 2H), 1.46 (s, 9H), 0.76 (d, J=6.6 Hz, 12H). MS(ESI), m/z (%): 547.38 [M+H]⁺. White solid.

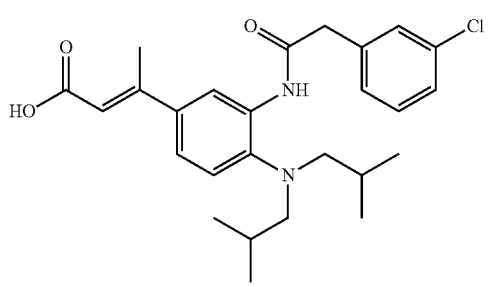

Compound 1064

¹H-NMR (600 MHz, DMSO-d₆) δ 12.04 (s, 1H), 8.73 (s, 1H), 8.27 (s, 1H), 7.44 (s, 1H), 7.38 (s, 1H), 7.36 (s, 1H), 7.27 (d, J=1.9 Hz, 1H), 7.25 (s, 1H), 6.04 (s, 1H), 3.79 (s, 2H), 2.61 (d, J=7.1 Hz, 4H), 2.45 (s, 3H), 1.60 (dd, J=12.4, 5.8 Hz, 2H), 0.77 (d, J=6.6 Hz, 12H). MS(ESI), m/z (%): 457.26 [M+H]⁺. White solid.

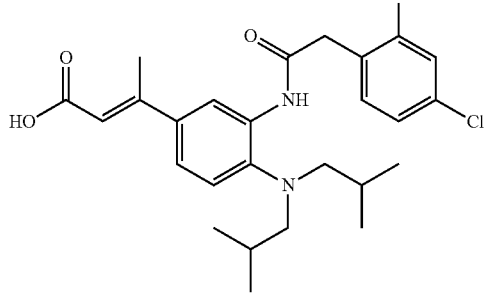

Compound 1065

¹H-NMR (600 MHz, DMSO-d₆) δ 12.06 (s, 1H), 8.73 (s, 1H), 8.33 (s, 1H), 7.64 (s, 1H), 7.52 (d, J=8.5 Hz, 1H), 7.46 (s, 1H), 7.28 (s, 2H), 6.04 (s, 1H), 3.92 (s, 2H), 2.64 (d, J=7.1 Hz, 4H), 2.45 (s, 3H), 1.64-1.61 (m, 2H), 0.81 (d, J=6.6 Hz, 12H). MS(ESI), m/z (%): 491.22 [M+H]⁺. White solid.

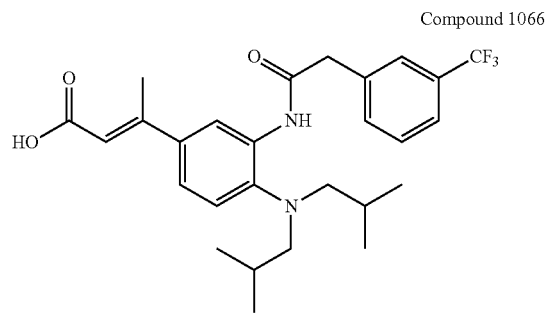 [SMILES: C/C(=C\C(=O)O)c1ccc(N(CC(C)C)CC(C)C)c(NC(=O)Cc2cccc(C(F)(F)F)c2)c1]

Compound 1066

¹H-NMR (600 MHz, DMSO-d₆) δ 12.02 (s, 1H), 8.80 (s, 1H), 8.23 (s, 1H), 7.73 (d, J=3.1 Hz, 1H), 7.68-7.66 (m, 1H), 7.27 (d, J=2.0 Hz, 1H), 7.25 (s, 1H), 7.21 (d, J=8.3 Hz, 1H), 6.93 (d, J=6.7 Hz, 1H), 6.04 (s, 1H), 3.90 (s, 2H), 2.62 (d, J=7.0 Hz, 4H), 2.45 (s, 3H), 1.59 (d, J=4.2 Hz, 2H), 0.76 (d, J=6.6 Hz, 12H). MS(ESI), m/z (%): 491.21 [M+H]⁺. White solid.

Test Method and Results of Inhibition Rate of IDO1 Enzyme in Hela Cells:

Human cervical cancer cell line Hela (obtained from Chinese academy of sciences cell bank) was cultured in logarithmic growth phase and counted after routine digestion. RPMI 1640 complete medium (Corning, USA, containing 10% FBS) was used to adjust the concentration to Ix 10⁵/ml, inoculated into 96-well plates, 100 ul/well, incubated for 24 hours.

Stimulant solution configuration: Human recombinant IFN-γ(Shanghai Sangon Biotech) was subpacked according to the instructions, the concentration was adjusted twice as high as the final concentration by RPMI1640 complete medium, that is 100 ng/ml.

Compounds solution configuration: DMSO was used to dissolve the drug, and then RPMI 1640 was used to dilute the drug to twice the detection concentration.

The old culture medium were discarded from 96-well plates, and added 100 ul stimulation solution and 100 ul compounds solution to each hole; set up interferon growth control group, each group had three multiple holes; incubated 48 hours.

180 uL medium from 96-well plate were collected and mixed with 45 μL of 30% (W/V) trichloroacetic acid. Plate was centrifuged for 5 min at 8000 rpm. The supernatant was added with fresh 4-dimethylaminobenzaldehyde (2%, W/V). After full shock, measured at 480 nm using a ElISA reader.

TABLE 7

Inhibition rate of compounds on IDO1 activity enzyme in Hela cells

| Compound Number | Inhibition rate (%) | |
| --- | --- | --- |
|  | 10 μmol | 100 nmol |
| Compound 9 | 100 | 100 |
| Compound 13 | 100 | 100 |
| Compound 14 | 100 | 100 |
| Compound 396 | 100 | 69.2 |
| Compound 397 | 100 | 75.5 |
| Compound 403 | 100 | 76.4 |
| Compound 404 | 100 | 73.2 |
| Compound 518 | 100 | 76.8 |
| Compound 525 | 100 | 75.1 |
| Compound 564 | 100 | 72.2 |
| Compound 772 | 100 | 74.2 |
| Compound 779 | 100 | 77.1 |

TABLE 7-continued

Inhibition rate of compounds on IDO1 activity enzyme in Hela cells

| Compound Number | Inhibition rate (%) | |
|---|---|---|
| | 10 μmol | 100 nmol |
| Compound 1021 | 100 | 42.1 |
| Compound 1022 | 53.7 | 21.2 |
| Compound 1023 | 100 | 35.1 |
| Compound 1024 | 58.2 | 29.5 |
| Compound 1025 | 68.8 | 24.6 |
| Compound 1026 | 54.3 | 21.0 |
| Compound 1027 | 100 | 71.1 |
| Compound 1028 | 100 | 41.5 |
| Compound 1030 | 100 | 23.8 |
| Compound 1031 | 72.7 | 29.6 |

The compounds described in the above table have certain inhibitory effects, Compounds 9, 13 and 14 can inhibit IDO-1 activity 100% at 100 nmol concentration.

TABLE 8

IC$_{50}$ Value (nmol/L) of compounds on IDO1 enzyme activity in Hela cells

| Compound Number | Inhibition rate IC$_{50}$ (nmol/L) |
|---|---|
| Compound 13 | 3.69 |
| Compound 14 | 0.18 |
| Compound 51 | 3.69 |
| Compound 55 | 0.09 |
| Compound 56 | 0.13 |
| Compound 525 | 1.36 |
| Compound 530 | 8.26 |
| INCB024360 | 3.78 |
| IN-4 | 1.56 |

As shown in the table above, the IC$_{50}$ of the compounds is lower than 100 nmol/L, and the activities of the compounds 525, 13, 14, 56, 55 and 51 can reach or exceed those of the positive control drugs INCB024360 and IN-4, indicating that these compounds have good IDO1 enzyme inhibitory activities.

As shown in Table 7 and Table 8 above, these compounds have potential therapeutic effects on colorectal cancer, pancreatic cancer, breast cancer, prostate cancer, lung cancer, ovarian cancer, cervical cancer, renal cancer, head and neck cancer, lymphoma, leukemia or melanoma with high expression of IDO1. It has potential therapeutic effects on other diseases such as viral infection, depression, organ transplant rejection or autoimmunity caused by high expression of IDO1.

INCB024360 control sample was purchased from Beijing Innochem Technology Co., Ltd. with batch number WG0292821-160526001. IN-4 was purchased from Medchem Express Biotechnology Company, USA, with batch number Lot #19346.

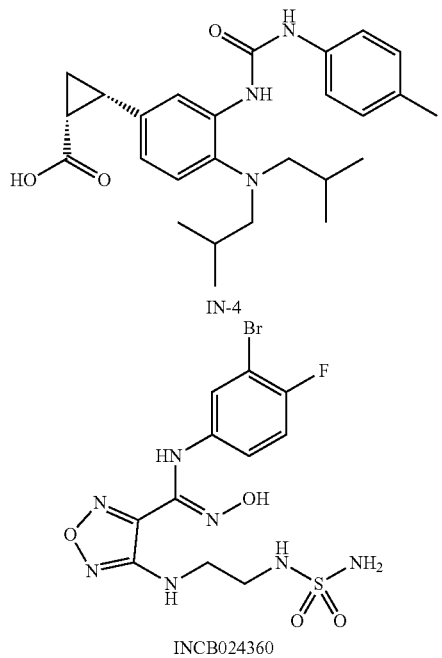

Pharmacokinetic Test and Results of Compound 55:

12 Male Sprague-Dawley rats were grouped random. The final concentration of compound 55 was 1.5 mg/ml. The drug was dissolved in a solvent system of 10% DMSO, 10% hydrogenated castor oil and 90% normal saline (compounds were dissolved by DMSO, hydrogenated castor oil and saline in turn by vortex or ultrasound), and the drug solution was given orally (30 mg/kg). The rats were fasted overnight but had free access to water, feeding resumed 4 hours after administration. Blood samples (0.3-0.4 mL) were collected into heparinized tubes by Retinal vein plexus at 0, 0.17, 0.33, 0.67, 1, 2, 4, 7, 10 and 24 hours after administration orally. Tubes were anticoagulated with heparin sodium (5% heparin sodium solution filled EP tube, poured out, dried). 100 uL plasma was obtained by centrifugation (10000 rpm, 3 min) and stored at −20° C. before analysis.

TABLE 9

Oral pharmacokinetic data of compound 55

| Testing Compound | Unit | Compound 55 |
|---|---|---|
| Dosage | mg/kg | 30 mg/kg |
| AUC | ng · h/mL | 43655.98 |
| T1/2 | h | 5.0 |
| Cmax | ng/mL | 16760.13 |

The results showed that compound 55 had good pharmacokinetic parameters.

Pharmacodynamics of Some Compounds In Vivo (Intraperitoneal Injection):

The anti-colon cancer CT26 activity of these compounds was tested in vivo. 1×10$^6$ CT26 cells were inoculated subcutaneously in the right axillary of BALB/c mice by cell suspension inoculation. When the growth of tumors were clearly observed, 42 moderately tumor size animals were selected and randomly divided into test group, solvent control group and positive drug group, with 6 animals in each group. The positive drug group was given 1-methyl-D-tryptophan 300 mg/kg daily by oral, and the INCB024360 group was given compound INCB024360 50 mg/kg daily by intraperitoneal injection. The compound groups were intraperitoneally injected with 50 mg/kg of the compound every day, while the solvent control group was given the same dosage with the same volume of mixed solvent. The weight of the mice and the length and short diameter of the transplanted tumors were measured three times a week during the administration. The tumor volume (VT), relative volume (RVT) and tumor proliferation rate (T/C %) were calculated. After two weeks of administration, nude mice bearing tumors in each experimental group were executed by neck-lifting method. Solid tumour tissues were completely dissected. The weight of tumors in each experimental group was measured and the growth inhibition rate (%) was calculated.

TABLE 10

Statistical table of tumor weight and inhibition rate of tumor weight

| Group | Number of animals (n) | Tumor weight (mg) | Inhibition rate (%) |
|---|---|---|---|
| Vehicle | 6 | 3368.00 ± 557.96 | 0.0 |
| 1-MT | 6 | 2509.17 ± 352.16 | 25.5 |
| INCB024360 | 6 | 3026.17 ± 409.75 | 10.23 |
| Compound 14 | 6 | 2727.33 ± 404.42 | 19.02 |
| Compound 55 | 6 | 2121.17 ± 343.15 | 37.02 |

At the end of the experiment, the I-MT activity of the positive drug was better than that of INCB024360, and compound 55 was equivalent to that of 1-MT, which was better than that of INCB024360.

Pharmacodynamic of Some Compounds In Vivo (Oral Administration):

The anti-colon cancer CT26 activity of these compounds was tested in vivo. 1×10$^6$ CT26 cells were inoculated subcutaneously in the right axillary of BALB/c mice by cell suspension inoculation. When the growth of tumors were clearly observed, 56 moderately tumor size animals were selected and randomly divided into test group, solvent control group and positive drug group, with 8 animals in each group. In the positive drug group, INCB024360 was given 50 mg/kg each time, compound 14 was given 50 mg/kg each time, compound 55 low dose group, compound 55 middle dose group and compound 55 high dose group were given 20 mg/kg, 50 mg/kg and 100 mg/kg respectively, compound 55 intraperitoneal injection group was given 50 mg/kg each time. The solvent control group was given the same volume of mixed solvents by oral. The above groups were administered twice a day. The weight of the mice and the length and short diameter of the transplanted tumors were measured three times a week during the administration. The tumor volume (VT), relative volume (RVT) and tumor proliferation rate (T/C %) were calculated. After two weeks of administration, nude mice bearing tumors in each experimental group were executed by neck-lifting method. Solid tumour tissues were completely dissected. The weight of tumors in each experimental group was measured and the growth inhibition rate (%) was calculated.

TABLE 11

Statistical table of tumor weight and inhibition rate of tumor weight

| Group | Dose (mg/kg) | Number of animals (n) | Tumor weight (mg) | Inhibition rate (%) |
|---|---|---|---|---|
| Solvent control | — | 8 | 1267.13 ± 331.64 | |
| INCB024360 | 50 | 8 | 840.63 ± 144.34 | 33.66 |
| Compound 55 | 20 | 8 | 1109.75 ± 191.47 | 12.42 |
| Compound 55 | 50 | 8 | 924.25 ± 150.35 | 27.06 |
| Compound 55 | 100 | 8 | 847.00 ± 305.01 | 33.16 |
| Compound 14 | 50 | 8 | 793.38 ± 246.34 | 37.39 |
| Compound 55 (IP) | 50 | 8 | 824.00 ± 161.64 | 34.97 |

At the end of the experiment, the activity of compound 55, high dose group and compound 14 was similar to that of positive drug INCB024360.

Combining with the previous intraperitoneal injection in vivo pharmacodynamics experiments, compound 55 has better pharmacodynamics than INCB024360 under the condition of single administration per day, and is equivalent to INCB024360 under the condition of twice administration per day. The T1/2 data of INCB024360 reported in the literature were 2.3 hours and that of compound 55 was 5.0 hours. Combining animal pharmacodynamics experiment and pharmacokinetics experiment data, compound 55 has better pharmacokinetic properties than INCB024360, and can achieve considerable pharmacodynamics with fewer times of administration.

We claim:

1. A vinylarene derivative having formula I, its stereoisomer, cis-trans isomer, tautomer and pharmaceutically acceptable salt thereof where formula I includes:

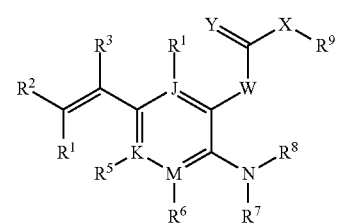

and wherein

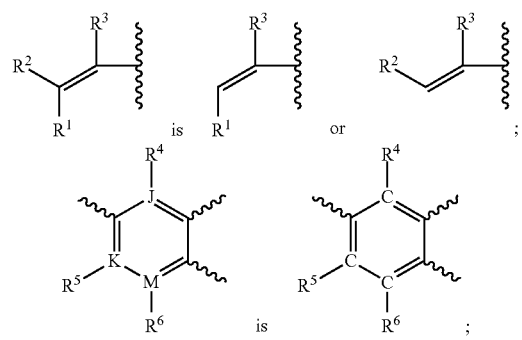

W is NH;
X is NH or CH$_2$;
Y is O;
J is C;

K is C;
M is C;
R$^1$ and R$^2$ is selected from COOH,

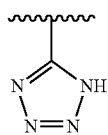

or COOCH$_2$CH$_3$;
R$^3$ is selected from CH$_3$;
R$^4$ is selected from H;
R$^5$ is selected from H;
R$^6$ is selected from H;

R$^7$ and R$^8$ are the same or different and selected from n-butyl or isobutyl;
R$^9$ is selected from 2-methylphenyl, 3-methylphenyl, 4-methylphenyl, 2,4-dimethylphenyl, 2,4-difluorophenyl, 2-fluoro-4-methylphenyl, 3-trifluoromethyl-4-chlorophenyl, phenyl, 2-chlorophenyl, 3-chlorophenyl, 4-chlorophenyl, 2,4-dichlorophenyl, 2-fluorophenyl, 4-fluorophenyl, 3-fluorophenyl or 5-methylisoxazolyl.

2. A treatment method comprising administering to a subject with a cancer selected from colon cancer, pancreatic cancer, breast cancer, prostate cancer, lung cancer, ovarian cancer, cervical cancer, kidney cancer, head and neck cancer, lymphoma, leukemia or melanoma an effective amount of the vinylarene derivative described in claim 1.

3. A pharmaceutical composition comprising an effective amount of the compound of claim 1 and a pharmaceutically acceptable carrier or diluent.

* * * * *